US010035849B2

(12) United States Patent
Kelley et al.

(10) Patent No.: US 10,035,849 B2
(45) Date of Patent: Jul. 31, 2018

(54) METHODS AND COMPOSITIONS FOR TARGETING POLYUBIQUITIN

(71) Applicant: GENENTECH, INC., South San Francisco, CA (US)

(72) Inventors: Robert F. Kelley, San Bruno, CA (US); Marissa Matsumoto, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/153,644

(22) Filed: May 12, 2016

(65) Prior Publication Data

US 2016/0355577 A1   Dec. 8, 2016

Related U.S. Application Data

(60) Division of application No. 14/732,243, filed on Jun. 5, 2015, now Pat. No. 9,365,642, which is a continuation of application No. 13/361,093, filed on Jan. 30, 2012, now Pat. No. 9,081,015, which is a division of application No. 12/355,531, filed on Jan. 16, 2009, now Pat. No. 8,133,488.

(60) Provisional application No. 61/127,862, filed on May 16, 2008, provisional application No. 61/011,577, filed on Jan. 18, 2008.

(51) Int. Cl.
A61K 39/395 (2006.01)
C07K 16/18 (2006.01)
G01N 33/68 (2006.01)
C07K 14/47 (2006.01)

(52) U.S. Cl.
CPC .............. *C07K 16/18* (2013.01); *C07K 14/47* (2013.01); *G01N 33/68* (2013.01); *C07K 2317/14* (2013.01); *C07K 2317/21* (2013.01); *C07K 2317/24* (2013.01); *C07K 2317/31* (2013.01); *C07K 2317/35* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/92* (2013.01); *G01N 2333/47* (2013.01); *G01N 2440/36* (2013.01)

(58) Field of Classification Search
None
See application file for complete search history.

(56) References Cited

U.S. PATENT DOCUMENTS

| 7,763,245 B2 | 7/2010 | Gordon et al. |
| 7,985,840 B2 | 7/2011 | Fuh et al. |
| 8,133,488 B2 | 3/2012 | Kelley et al. |
| 8,603,475 B2 | 12/2013 | Gordon et al. |
| 9,081,015 B2 | 7/2015 | Kelley et al. |
| 9,365,642 B2 | 5/2016 | Kelley et al. |
| 2005/0106667 A1 | 5/2005 | Fellouse et al. |
| 2007/0166778 A1 | 7/2007 | Rain et al. |
| 2007/0218069 A1 | 9/2007 | Gordon et al. |
| 2007/0218079 A1 | 9/2007 | Patzel |
| 2009/0191209 A1 | 7/2009 | Kelley et al. |
| 2010/0267050 A1 | 10/2010 | Gordon et al. |
| 2011/0256133 A1 | 10/2011 | Dixit et al. |
| 2013/0058955 A1 | 3/2013 | Kelley et al. |

FOREIGN PATENT DOCUMENTS

| JP | 07238096 | 9/1995 |
| WO | WO 2004/003019 A2 | 1/2004 |
| WO | WO 2007/025216 A2 | 3/2007 |
| WO | WO 2007/120334 A2 | 10/2007 |
| WO | WO 2008/121813 A2 | 10/2008 |
| WO | WO 2009/126350 A2 | 10/2009 |
| WO | WO 2011/130499 A1 | 10/2011 |

OTHER PUBLICATIONS

Dillman J. Clinical Oncology vol. 12 p. 1497 (1994) (Year: 1994).*
Li et al Expert Opin. Biol. Ther. vol. 7 p. 319 (2007) (Year: 2007).*
Christiansen et al, Molecular Therapeutics col. 3 p. 1493 (2004) (Year: 2004).*
Strome et al., The Oncologist, 2007; 12:1084-95 (Year: 2007).*
Brand et al., Anticancer Res. 2006; 26:463-70 (Year: 2006).*
"Product information sheet for BIOMOL catalogue No. PW8805" pp. 1-2 (Jan. 25, 2004).
Alves-Rodrigues et al., "Ubiquitin, cellular inclusions and their role in neurodegeneration" Trends in Neurosciences 21(12): 516-520 (1998).
Beckman et al., "On ubiquitin ligases and cancer" Hum. Mutat. 25:507-512 (2005).
Beckmann et al., "The ubiquitin-modifying enzyme A20 is required for termination of toll-like receptors responses" Nature Immunol. 5(10): 1052-1060 (Oct. 2004).
Bodine et al., "Identification of ubiquitin ligases required for skeletal muscle atrophy" Science 294(5547): 1704-1708 (Nov. 23, 2011).
Boone, D. L. et al., "The ubiquitin-modifying enzyme A20 Is required for termination of toll-like receptor responses" Nature Immunol. 5(10): 1052-1060 (Oct. 2004).
Brorson, "Mutational analysis of avidity and fine specificity of anti-levan antibodies" J Immunol (added article title info, 163:6694-6701 (Dec. 1999).
Brummel e al., "Probing the combining site of an anti-carbohydrate antibody by saturation-mutagenesis: role of heavy-chain CDR3 residues" Biochemistry 32(4): 1180-1187 (Feb. 1993).
Burks, E., et al., "In vitro scanning saturation mutagenesis of an antibody binding pocket" Proc. Natl. Acad. Sci. 94:412-417 (1997).
Cammarata et al., Ubiquitin-reactive neurites in cerebral cortex of subjects with Huntington's chorea: a pathological correlate of dementia? Neuroscience Letters 156(1-2):96-98 (1993).
Campbell, A. Monoclonal Antibody Technology "1" The Netherlands: Elsevier Science Publishers B.V. 1-32 (1984).
Carrion-Vazquez et al., "The mechanical stability of ubiquitin is linkage dependent" Nat Struct Biol. (Epub Aug. 17, 2003) 10(9):738-743 (Sep. 2003).

(Continued)

Primary Examiner — Sheela J. Huff
(74) Attorney, Agent, or Firm — McNeill Baur PLLC

(57) ABSTRACT

Anti-K63-linked polyubiquitin monoclonal antibodies, and methods for using the antibodies, are provided.

23 Claims, 25 Drawing Sheets

(56) References Cited

OTHER PUBLICATIONS

Casset. F. et al., "A peptide mimetic of an anti-CD4 monoclonal antibody by rational design" Biochem. & Biophys. Res. Comm. 307:198-205 (2003).
Chau et al., A multiubiquitin chain is confined to specific lysine in a targeted short-lived protein Science 243(4898):1576-1583 (Mar. 24, 1989).
Chen et al., "Structural basis for scaffolding-mediated assembly and maturation of dsDNA virus" Proc Natl Acad Sci U S A. 108(4):1355-60 (Jan. 2011).
Chen, Y. et al., "Selection and analysis of an optimized anti-VEGF antibody: crystal structrure of an affinity-matured Fab in complex with antigen" J. Mol. Biol. 293:865-881 (1999).
Chung et al., "The role of ubiquitin-proteasomal pathway in Parkinson's disease and other neurodegenerative disorders" Trends in Neurosciences 24(11 Suppl):S7-14 (Nov. 2001).
Ciechanover, "The ubiquitin-proteasome pathway: on protein death and cell life" EMBO Journal 17(24):7151-7160 (1998).
Clark, L. A. et al., "Affinity enhancement of an in vivo matured therapeutic antibody using structure-based computational design" Prot. Sci. 15:949-960 (2006).
Coleman, P.M., "Effects of amino acid sequence changes on antibody-antigen interactions" Res Immunol 145:33-36 (1994).
Cook, W. J. et al., "Structure of diubiquitin conjugate and a model for interaction with ubiquitin conjugating enzyme (E2)" Journal of Biological Chemistry 267(23):16467-16471 (Aug. 15, 1992).
International Search Report and Written Opinion for International Patent Application No. PCT/US2009/031310, dated Oct. 21, 2009, 22 pages.
International Search Report and Written Opinion for International Patent Application No. PCT/US2011/032468, dated Jun. 3, 2011, 15 pages.
International Search Report for PCT/US/2006/062115, dated May 29, 2008, 7 pages.
Crosas, B. et al., "ubiquitin chans are remodeled at the proteasome by opposing ubuiquitin ligases and deubiquitinating activities" Cell 127:1401-1413 (Dec. 29, 2006).
De Pascalis et al., "Grafting of "abbreviated" complementarity-determining regions containing specificity-determining residues essential for ligand contact to engineer a less immunogenic humanized monoclonal antibody" J. Immunol. 169:3076-3084 (2002).
Deng et al., "Activation of the IkappaB kinase complex by TRAF6 requires a dimeric ubiquitin-conjugating enzyme complex and a unique polyubiquitin chain" Cell 103(2):351-361 (Oct. 13, 2000).
Dufner et al., "Harnessing phage and ribosome display for antibody optimisation" Trends in Biotechnology 24(11):523-529 (2006).
Fellouse et al., "High-throughput generation of synthetic antibodies from highly functional minimalist phage-displayed libraries" J Mol Biol. 373(4):924-40 (Nov. 2007).
Finley et al., "Inhibition of proteolysis and cell cycle progression in a multibiquitination-deficient yeast mutant" Mol Cell Biol. 14(8):5501-5509 (Aug. 1994).
Flick et al., "Proteolysis-independent regulation of the transcription factor Met4 by a single Lys 48-linked ubiquitin chain" Nat Cell Biol. (epub Jun. 20, 2004) 6(7):634-641 (Jul. 2004).
Fujimuro and Yokosawa, "Production of antipolyubiquitin monoclonal antibodies and their use for characterization and isolation of polyubiquitinated proteins" Methods of Enzymology 399:75-86 (Dec. 15, 2005).
Fujimuro et al., "Production and characterization of monoclonal antibodies specific to multi-ubiquitin chains of polyubiquitinated proteins" FEBS Letters 349(2):173-180 (1994).
Gallop et al., "Applications of combinatorial technologies to drug discoveries. 1. background and peptide combinatorial libraries" J Med Chem 37(9):1233-1251 (1994).
Garnett et al., "UBE2S elongates ubiquitin chains on APC/C substrates to promote mitotic exit" Nat Cell Biol. 11(11):1363-9 (2009).
Ghosh and Karin, "Missing pieces in the NF-kappaB puzzle" Cell 109(Suppl.):S81-S96 (Apr. 2006).
Gorman et al., "Transient Production of Proteins Using an Adenovirus Transformed Cell Line" DNA Prot. Eng. Tech. 2(1):3-10 (1990).
Guterman and Glickman, "Deubiquitinating enzymes are IN/(trinsic to proteasome function)" Curr Protein Pept Sci. 5(3):201-544 (2004).
Hashizume et al., "The RING heterodimer BRCA1-BARD1 is a ubiquitin ligase inactivated by a breast cancer-derived mutation" J Biol Chem. 276(18):14537-14540 (May 4, 2001).
Hicke and Dunn, "Regulation of membrane protein transport by ubiquitin and ubiquitin-binding proteins" Annu Rev Cell Dev Biol. (epub Jun. 20, 2003) 19:141-172 (2003).
Hicke, L., "Protein regulation by monoubiquitin" Nature Reviews Mol. Cell Biol. 2:195-201 (Mar. 2001).
Hoege et al., "RAD6-dependent DNA repari is linked to modication of PCNA by ubiquitin and SUMO" Nature 419(6903)135-141 (Sep. 12, 2002).
Hofmann and Pickart, "In vitro assempaly and recognition of Lys-63 polyubiquitin chains" J Biol Chem. 276(30): 27936-27943 (Jul. 27, 2001).
Hofmann and Pickart, "Noncanonical MMS2-encoded ubiquitin-conjugatting enzyme functions in assembly of novel polyubiquitin chains for DNA repair" Cell 96(5):645-653 (Mar. 5, 1999).
Holm, et al., "Functional mapping and single chain construction of the anti-cytokeratin 8 monoclonal antibody TSI" Molucular Immunology 44:1075-1084 (2007).
Holmberg et al., "Spinocerebellar ataxia type 7 (SCA7): a neurodegenerative disorder with neuronal intranuclear inclusions" Hum Mol Genet. 7(5):913-918 (1998).
Jang et al., "The structural basis for DNA binding by an anti-DNA autoantibody," Mol. Immunol., 35(18): 1207-17 (Dec. 1998).
Jin et al., "Mechanism of ubiquitin-chain formation by the human anaphase-promoting complex," Cell 133(4): 653-65 (May 2008).
Johnson, "Ubiquitin branches out" Nat Cell Biol. 4(12):E295-E298 (Dec. 2002).
Kalchman et al., "Huntingtin is ubiquitinated and interacts with a specific ubiquitin-conjugating enzyme" J Biol Chem., 271(32):19385-19394 (Aug. 9, 1996).
Kim, H. T. et al., "Certain pairs of ubiquitin-conjugating enzymes (E2s) and ubiquitin-protein ligases (E3s) synthesize nondegradable forked ubiquitin chains containing all possible isopeptide linkages" Journal of Biological Chemistry 282(24):17375-17386 (Jun. 15, 2007).
Kirkpatrick, D. S. et al., "Quantitative analysis of in vitro ubiquitinated cyclin B1 reveals complex chain topology" Nature Cell Biol. 8(7):700-710 (Jul. 2006).
Kishino et al., "UBE3A/E6-AP mutations cause Angelman syndrome" Nat Genet. 15(1):70-73 (Jan. 1997).
Kobayashi, H., et al., "Tryptophan H33 plays an important role in pyrimidin (6-4) pyrimidone photoproduct binding by a high-affinity antibody" Protein Engineering 12(10):879-884 (1999).
Kumar, Sanjeev, et al., "Molecular cloning and expression of the fabs of human autoantibodies in *Escherichia coli*" J. Bio. Chem. 275(45):35129-35136 (2000).
Kunkel, "Rapid and Efficient Site-Specific Mutagenesis Without Phenotypic Selection" Proc. Natl. Acad. Sci.:488-492 (Jan. 1985).
Kuzuhara et al., "Lewy bodies are ubiquitinated. A light and electron microscopic immunocytochemical study" Acta Neuropathology (Berl) 75(4):345-353 (1988).
Lam et al., "Inhibition of the ubiquitin-proteasome system in Alzheimer's disease" Proc Natl Acad Sci USA 97(18):9902-9906 (Aug. 29, 2000).
Lamminmaki et al., JBC, vol. 276, pp. 336687-336694 (2001).
Lee et al., "High-affinity human antibodies from phage-displayed synthetic Fab libraries with a single framework scaffold" J. Mol. Biol. 340(5):1073-1093 (2004).
Leigh et al., "New aspects of the pathology of neurodegenerative disorders as revealed by ubiquitin antibodies" Acta Neuropathol. 79(1)61-72 (1989).
Leroy et al., "The ubiquitin pathway in Parkinson's disease" Nature 395(6701):451-452 (Oct. 1, 1998).

(56) References Cited

OTHER PUBLICATIONS

Lim et al., "Parkin mediates nonclassical, proteasomal-independent ubiquitination of synphilin-1:implicaitons for Lewy body formation" J Neurosci. 25(8):2002-2009 (Feb. 23, 2005).
MacCallum et al., "Antibody-antigen Interactions: Contact Analysis and Binding Site Topography" J. Mol.Biol. 262:732-745 (1996).
Majetschak et al., "Extracellular ubiquitin inhibits the TNF-alpha response to endotoxin in peripheral blood mononuclear cells and regulates endotoxin hyporesponsive in critical illness" Blood 101(5):1882-1890 (Mar. 1, 2003).
Matsumoto et al., "K11-linked polyubiquitination in cell cycle control revealed by a K11 linkage-specific antibody" Mol Cell 39(3):477-84 (Aug. 2010).
McNaught et al., "Failure of the ubiquitin-proteasome system in Parkinson's diseease" Nat Rev Neurosci. 2(8):589-594 (Aug. 2001).
Mitch and Goldberg, "Mechanisms of muscle wasting. The role of the ubiquitin-proteasome pathway" N. Engl J Med. 335(25):1897-1905 (Dec. 19, 1996).
Mori et al., "Ubiquitin is a component of paired helical filaments in Alzheimer's disease" Science 235(4796):1641-1644 (Mar. 27, 1987).
Naze et al., "Mutation analysis and association studies of the ubiquitin carboxy-terminal hydrolase L1 gene in Huntington's disease" Neuroscience Letters 328(1):1-4 (2002).
Nemes, Z. et al., "Cross-linking of ubiquitin, HSP27, parking and α-synuclein by /147-gluamyl-ϵ-lysine bonds in Alzheimer's nurofibrillary tangles" FASEB J. 18(10):1135-7 (May 2004).
Newton, K. et al., "Ubiquitin chain editing revealed by polyubiquitin linkage-specific antibodies" Cell 134:668-678 (Aug. 22, 2008).
Padlan et al., PNAS, vol. 86, pp. 5938-5942 (1989).
Palombella et al., "The ubiquitin-proteasome pathway is required for processing the NF-kappa B1 precursor protein and the activation of NF-kappa B" Cell 78(5):773-785 (Sep. 9, 1994).
Peng et al., "A proteomics approach to understanding protein ubiquitination" Nat Biotechnol. 21(8):921-926 (Aug. 2003).
Pickart and Fushman, "Polyubiquitin chains: polymeric protein signals" Curr Opin Chem Biol. (epub Oct. 28, 2004) 8(6):610-616 (Dec. 2004).
Pickart, "Mechanisms underlying ubquitination" Annu Rev Biochem. 70:503-533 (2001).
Pickart, "Ubiquitin enters the new millennium" Mol Cell. 8(3):499-504 (Sep. 2011).
Rich et al., A Global Benchmark Study Using Affinity-Based Biosensors, Anal. Biochem., vol. 386, pp. 194-216 (2009).
Rudikoff, et al., "Single amino acid substitution altering antigen-binding specificity" Proc. Natl. Acad. Sci. USA 79:1979-1983 (1982).
Salghetti et al., "Destruction fo Myc by ubiquitin-mediated proteolysis: cancer-associated and transforming mutations stabilize Myc" EMBO Journal 18(3):717-726 (1999).
Seibenhener et al., "Sequestosome 1/p62 is a polyubiquitin chain binding protein involved in ubiquitin proteasome degradation" Mol Cell Biol. 24(18):8055-8068 (Sep. 2004).
Shimura et al., "Familial Parkinson disease gene product, parkin, is a ubiquitin-protein ligase" Nat Genet. 25(3):302-305 (Jul. 2000).
Smith-Gill, S., et al., "Contributions of immunoglobulin heavy and light chains to antibody specificity for lysozyme and two haptens" J. immunol. 139:4135-4144 (1987).
Song, Mi-Kyung, et al., "Light chain of natural antibody plays a dominant role in protein antigen binding" Biochem Biophys Res. Comm 268:390-394 (2000).
Spataro et al., "The ubiquitin-proteasome pathway in cancer" Br J Cancer 77(3):448-455 (1998).
Spence et al., "A ubiquitin mutant with specific defects in DNA repair and multiubiquitination" Mol Cell Biol. 15(3):1265-1273 (Mar. 1995).

Spence et al., "Cell cycle-regulated modification of the ribosome by variant multiubiquitin chain" Cell 102(1):67-76 (Jul. 7, 2000).
Staub et al., "Regulation of stability and function of the epithelial Na+ channel (ENaC) by ubiquitination" EMBO Journal 16(21):6325-6336 (1997).
Stelter and Ulrich, "Control of spontaneous and damage-induced mutagenesis by SUMO and ubiquitin combination" Nature 425(6954):188-191 (Sep. 11, 2003).
Sun and Chen, "The novel functions of ubiquitination in signaling" Curr Opin Cell Biol. 16(2):119-126 (2004).
Takada et al., "Serum concentrations of free ubiquitin and multiubiquitin chains" Clin Chem. 43(7):1188-1195 (1997).
Tan, J. et al., "Lysine 63-linked ubiquitination promotes the formation and autophagic clearance of protein inclusions associated with neurodegenerative diseases" Human Mol Genetics 17(3):431-439 (Mar. 2008).
Tenno et al., "Structural basis for distinct roles of Lys63- and Lys48-linked polyubiquitin chains" Genes Cells 9(10):865-875 (2004).
Treier et al., "Ubiquitin-dependent c-Jun degradation in vivo is mediated by the delta domain" Cell 78(5):787-798 (Sep. 9, 1994).
Ulrich, "Degradation or maintenance: actions of the ubiquitin system on eukaryotic chromatin" Eukaryotic Cell 1(1):1-10 (Feb. 2002).
Vajdos et al., "Comprehensive functional maps of the antigen-binding site of an anti-ErbB2 antibody obtained with shotgun scanning mutagenesis" J. Mol. Biol. 320:415-428 (2002).
Vardan et al., "Structural properties of polyubiquitin chains in solution," J. Mol. Biol., 324: 637-647 (2002).
Ward et al., "Binding Activities of a Repertoire of Single Immunoglobulin Variable Domains Secreted from *Escherichia coli*" Nature 341:544-546 (Oct. 12, 1989).
Ward et al., "Degradation of CFTR by the ubiquitin-proteasome pathway" Cell 83(1):121-127 (Oct. 6, 1995).
Wertz et al., "De-ubiquitination and ubiquitin ligase domains of A20 downregulate NF-kappaB signalling" Nature 430:694-699 (Aug. 5, 2004).
Wilkinson, "Ubiquitination and deubiquitination: targeting of proteins for degradation by the proteasome" Semin Cell Dev Biol. 11(3):141-148 (2000).
Williamson et al., "Identification of physiological E2 module for the human anaphase-promoting complex" Proc Natl Acad Sci USA. 106(43)1 8213-8 (Oct. 2009).
Wong et al., "Drug discovery in the ubiquitin regulatory pathway" Drug Discov Today 8(16):746-754 (Aug. 2003).
Wu et al., "Humanization of a Murine Monoclonal Antibody of Simultaneous Optimization of Framework and CDR Residues" J. Mol. Biol. 294:151-162 (1999).
Yamin and Miller, "The interleukin-1 receptor-associated kinase is degraded by proteasomes following its phosphorylation" Journal of Biological Chemistry 272(34):21540-21547 (Aug. 22, 1997).
Yedidia et al., "Proteasome and ubiquitin are involved in the turnover of the wild-type prion protein" EMBO Journal 20(19):5383-5391 (2001).
Zhang et al., "Parkin functions as an E2-dependent ubiquitin-protein ligase and promotes the degradation of the synaptic vesicle-associated protein, CDCrel-1" Proc Natl Acad Sci USA. 94(24):13354-13359 (Nov. 21, 2000).
File history for U.S. Appl. No. 12/355,531, filed Jan. 16, 2009.
File history for U.S. Appl. No. 11/611,058, filed Dec. 14, 2006.
File history for U.S. Appl. No. 12/766,772, filed Apr. 23, 2010.
File history for U.S. Appl. No. 13/086,941, filed Apr. 14, 2011.
File history for U.S. Appl. No. 13/567,919, filed Aug. 6, 2012.
File history for U.S. Appl. No. 13/361,093, filed Jan. 30, 2012.
File history for U.S. Appl. No. 14/079,727, filed Nov. 14, 2013.
File history for U.S. Appl. No. 14/627,597, filed Feb. 20, 2015.
File history for U.S. Appl. No. 14/732,243, filed Jun. 5, 2015.
File history for U.S. Appl. No. 15/071,422, filed Mar. 16, 2016.

\* cited by examiner

1   MET GLN ILE PHE VAL LYS THR LEU THR GLY LYS THR ILE THR
15  LEU GLU VAL GLU PRO SER ASP THR ILE GLU ASN VAL LYS ALA
29  LYS ILE GLN ASP LYS GLU GLY ILE PRO PRO ASP GLN GLN ARG
43  LEU ILE PHE ALA GLY LYS GLN LEU GLU ASP GLY ARG THR LEU
57  SER ASP TYR ASN ILE GLN LYS GLU SER THR LEU HIS LEU VAL
71  LEU ARG LEU ARG GLY GLY
FIG. 1A
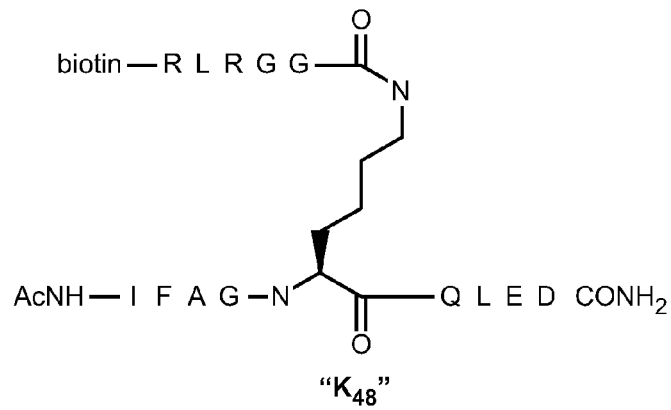
"K$_{48}$"
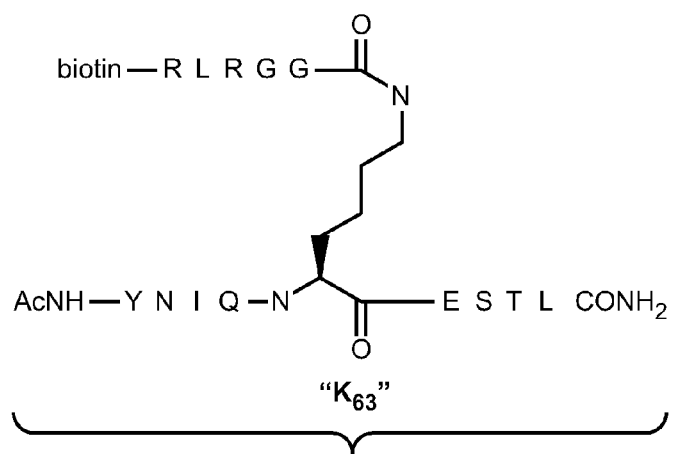
"K$_{63}$"
FIG. 1B

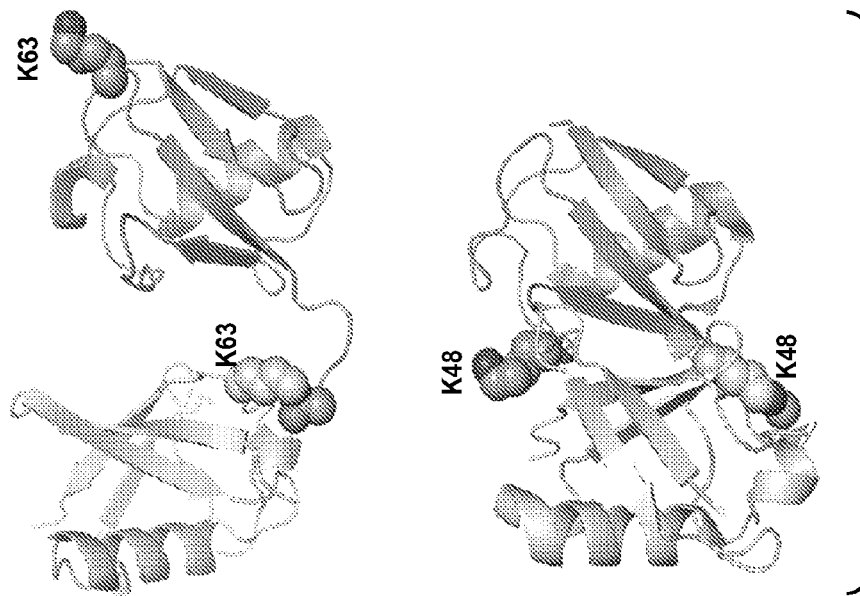
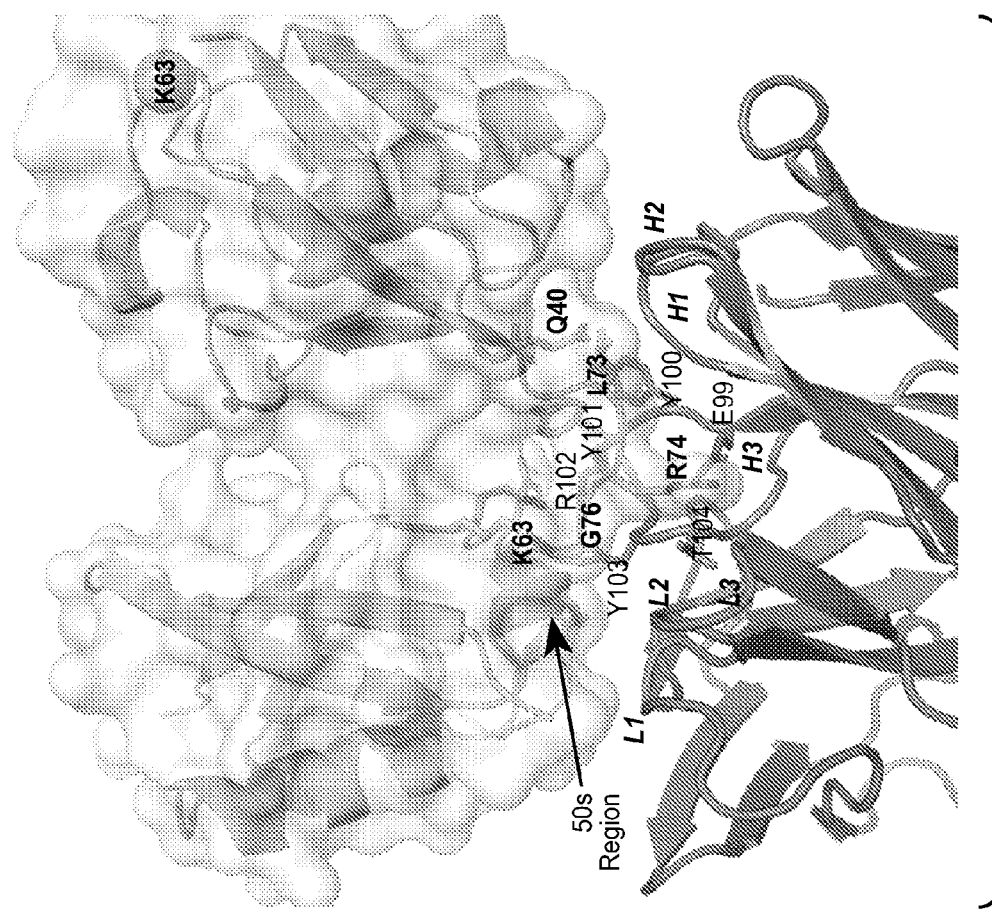
FIG. 2B
FIG. 2A

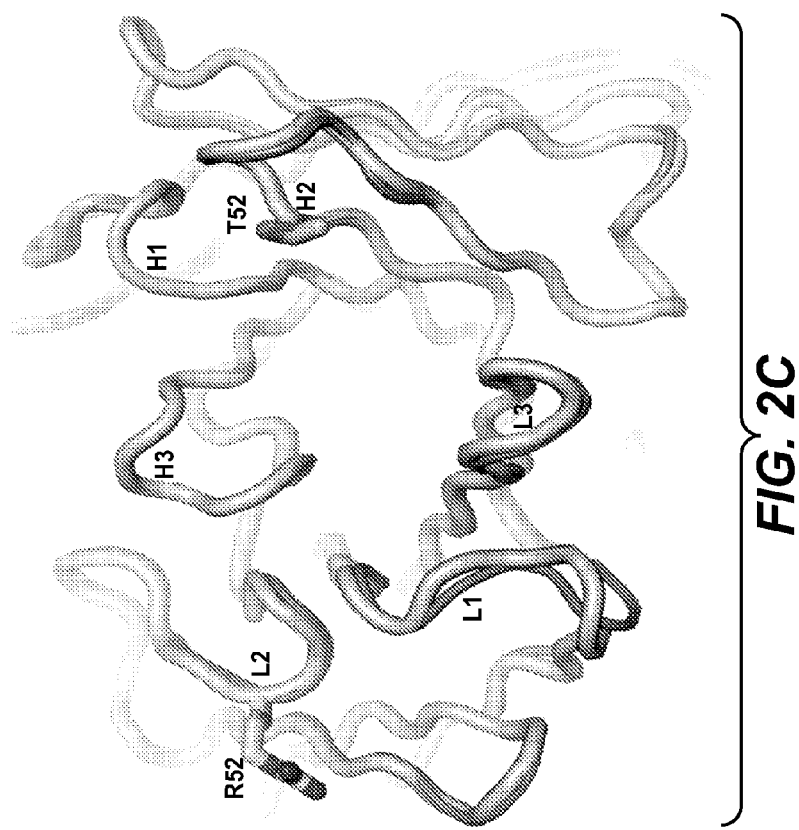
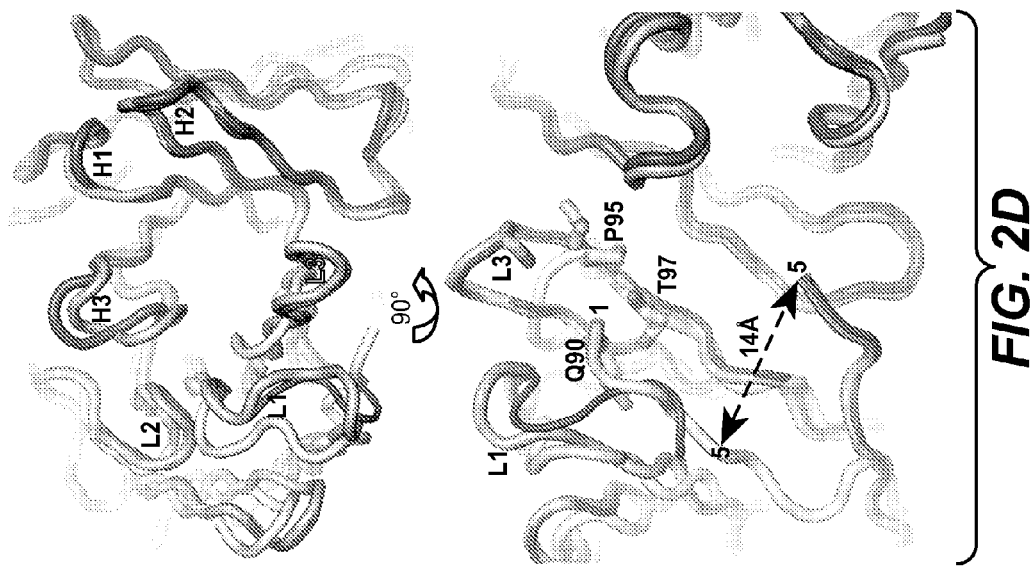
FIG. 2C
FIG. 2D

|   |   |   |   |   |
|---|---|---|---|---|
| I | A | QVQLVQSGAEVKKPGASVKVSCKASGYTFT | -H1- | WVRQAPGQGLEWMG | -H2- | RVTIT |
|   | B | QVQLVQSGAEVKKPGASVKVSCKAS | -H1- | WVRQAPGQGLEWM | -H2- | RVTIT |
|   | C | QVQLVQSGAEVKKPGASVKVSCKAS | -H1- | WVRQAPGQGLEWM | -H2- | RVTIT |
|   | D | QVQLVQSGAEVKKPGASVKVSCKAS | -H1- | WVRQAPGQGLEWM | -H2- | RVTIT |
| II | A | QVQLQESGPGLVKPSQTLSLTCTVSGGSVS | -H1- | WIRQPPGKGLEWIG | -H2- | RVTIS |
|   | B | QVQLQESGPGLVKPSQTLSLTCTVS | -H1- | WIRQPPGKGLEWI | -H2- | RVTIS |
|   | C | QVQLQESGPGLVKPSQTLSLTCTVS | -H1- | WIRQPPGKGLEWI | -H2- | RVTIS |
|   | D | QVQLQESGPGLVKPSQTLSLTCTVS | -H1- | WIRQPPGKGLEWI | -H2- | RVTIS |
| III | A | EVQLVESGGGLVQPGGSLRLSCAASGFTFS | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
|   | D | EVQLVESGGGLVQPGGSLRLSCAAS | -H1- | WVRQAPGKGLEWV | -H2- | RFTIS |
| Acceptor | A | EVQLVESGGGLVQPGGSLRLSCAASGFNIK | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
| Second Acceptor | A | EVQLVESGGGLVQPGGSLRLSCAASGFNIK | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
|   | D | EVQLVESGGGLVQPGGSLRLSCAAS | -H1- | WVRQAPGKGLEWV | -H2- | RFTIS |

FIG. 12A

|   |   |   |   |
|---|---|---|---|
| I |   |   |   |
| A | ADTSTSTAYMELSSLRSEDTAVYYCAR | -H3- | WGQGTLVTVSS SEQ ID NO.: 113, 114, 115, 116 |
| B | ADTSTSTAYMELSSLRSEDTAVYYCAR | -H3- | WGQGTLVTVSS SEQ ID NO.: 117, 118, 119, 120 |
| C | ADTSTSTAYMELSSLRSEDTAVYYCA  | -H3- | WGQGTLVTVSS SEQ ID NO.: 121, 122, 123, 124 |
| D | ADTSTSTAYMELSSLRSEDTAVYYC   | -H3- | WGQGTLVTVSS SEQ ID NO.: 125, 126, 127, 128 |
| II |  |   |   |
| A | VDTSKNQFSLKLSSVTAADTAVYYCAR | -H3- | WGQGTLVTVSS SEQ ID NO.: 129, 130, 131, 132 |
| B | VDTSKNQFSLKLSSVTAADTAVYYCAR | -H3- | WGQGTLVTVSS SEQ ID NO.: 133, 134, 135, 136 |
| C | VDTSKNQFSLKLSSVTAADTAVYYCA  | -H3- | WGQGTLVTVSS SEQ ID NO.: 137, 138, 139, 140 |
| D | VDTSKNQFSLKLSSVTAADTAVYYC   | -H3- | WGQGTLVTVSS SEQ ID NO.: 141, 142, 143, 144 |
| III |  |   |   |
| A | RDNSKNTLYLQMNSLRAEDTAVYYCAR | -H3- | WGQGTLVTVSS SEQ ID NO.: 145, 146, 147, 148 |
| B | RDNSKNTLYLQMNSLRAEDTAVYYCAR | -H3- | WGQGTLVTVSS SEQ ID NO.: 149, 150, 151, 152 |
| C | RDNSKNTLYLQMNSLRAEDTAVYYCA  | -H3- | WGQGTLVTVSS SEQ ID NO.: 153, 154, 155, 156 |
| D | RDNSKNTLYLQMNSLRAEDTAVYYC   | -H3- | WGQGTLVTVSS SEQ ID NO.: 157, 158, 159, 160 |
| Acceptor |  |   |   |
| A | ADTSKNTAYLQMNSLRAEDTAVYYCSR | -H3- | WGQGTLVTVSS SEQ ID NO.: 161, 162, 163, 164 |
| B | ADTSKNTAYLQMNSLRAEDTAVYYCAR | -H3- | WGQGTLVTVSS SEQ ID NO.: 165, 166, 167, 168 |
| C | ADTSKNTAYLQMNSLRAEDTAVYYCSR | -H3- | WGQGTLVTVSS SEQ ID NO.: 169, 170, 171, 172 |
| Second Acceptor |  |   |   |
| A | ADTSKNTAYLQMNSLRAEDTAVYYCAR | -H3- | WGQGTLVTVSS SEQ ID NO.: 173, 174, 175, 176 |
| B | ADTSKNTAYLQMNSLRAEDTAVYYCAR | -H3- | WGQGTLVTVSS SEQ ID NO.: 177, 178, 179, 180 |
| C | ADTSKNTAYLQMNSLRAEDTAVYYCA  | -H3- | WGQGTLVTVSS SEQ ID NO.: 181, 182, 183, 184 |
| D | ADTSKNTAYLQMNSLRAEDTAVYYC   | -H3- | WGQGTLVTVSS SEQ ID NO.: 185, 186, 187, 188 |

FIG. 12B

Framework Sequences of huMAb4D5-8 Light Chain

LC-FR1  $^1$Asp Ile Gln Met Thr Gln Ser Pro Ser Ser Leu Ser Ala Ser Val Gly Asp Arg Val Thr Ile Thr Cys$^{23}$  (SEQ ID NO: 205)

LC-FR2  $^{35}$Trp Tyr Gln Gln Lys Pro Gly Lys Ala Pro Lys Leu Leu Ile Tyr$^{49}$ (SEQ ID NO: 206)

LC-FR3  $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 207)

LC-FR4  $^{98}$Phe Gly Gln Gly Thr Lys Val Glu Ile Lys$^{107}$ (SEQ ID NO: 208)

Framework Sequences of huMAb4D5-8 Heavy Chain

HC-FR1  $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 209)

HC-FR2  $^{36}$Trp Val Arg Gln Ala Pro Gly Lys Gly Leu Glu Trp Val$^{48}$ (SEQ ID NO: 210)

HC-FR3  $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 211)

HC-FR4  $^{103}$Trp Gly Gln Gly Thr Leu Val Thr Val Ser Ser$^{113}$ (SEQ ID NO: 212)

*FIG. 14*

Framework Sequences of huMAb4D5-8 Light Chain Modified at Position 66 and 99 (Underlined)

LC-FR1  $^1$Asp Ile Gln Met Thr Gln Ser Pro Ser Ser Leu Ser Ala Ser Val Gly Asp Arg Val Thr Ile Thr Cys$^{23}$ (SEQ ID NO: 213)

LC-FR2  $^{35}$Trp Tyr Gln Gln Lys Pro Gly Lys Ala Pro Lys Leu Leu Ile Tyr$^{49}$ (SEQ ID NO: 214)

LC-FR3  $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 215)

LC-FR4  $^{98}$Phe <u>Arg</u> Gln Gly Thr Lys Val Glu Ile Lys$^{107}$ (SEQ ID NO: 216)

Framework Sequences of huMAb4D5-8 Heavy Chain Modified at Postions 71, 73 and 78 (Underlined)

HC-FR1  $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 217)

HC-FR2  $^{36}$Trp Val Arg Gln Ala Pro Gly Lys Gly Leu Glu Trp Val$^{48}$ (SEQ ID NO: 218)

HC-FR3  $^{66}$Arg Phe Thr Ile Ser <u>Arg</u> Asp <u>Asn</u> Ser Lys Asn Thr Ala <u>Leu</u> Tyr Leu Gln Met Asn83 Ser83a Leu83b Arg83c Ala Glu Asp Thr Ala Val Tyr Tyr Cys$^{92}$ (SEQ ID NO: 219)

HC-FR4  $^{103}$Trp Gly Gln Gly Thr Leu Val Thr Val Ser Ser$^{113}$ (SEQ ID NO: 220)

*FIG. 15*

METHODS AND COMPOSITIONS FOR TARGETING POLYUBIQUITIN

RELATED APPLICATIONS

This application is a divisional of U.S. patent application No. 14/732,243, filed Jun. 5, 2015, which is a continuation of U.S. patent application Ser. No. 13/361,093, filed Jan. 30, 2012, now U.S. Pat. No. 9,081,015 B2, which is a divisional of U.S. patent application Ser. No. 12/355,531, filed Jan. 16, 2009, now U.S. Pat. No. 8,133,488 B2, which claims priority under 35 U.S.C. § 119(e) to U.S. Provisional Application No. 61/011,577, filed Jan. 18, 2008, and to U.S. Provisional Application No. 61/127,862, filed May 16, 2008, the contents of which are incorporated in their entirety herein by reference.

FIELD OF THE INVENTION

This invention relates to the field of anti-polyubiquitin antibodies, and more particularly to anti-polyubiquitin antibodies that do not specifically bind to monoubiquitin and that can discriminate between polyubiquitins having different isopeptide linkages.

REFERENCE TO SEQUENCE LISTING SUBMITTED AS A TEXT FILE VIA EFS-WEB

A sequence listing is submitted as an ASCII formatted text file via EFS-Web, with a file name of "2016-08-03 01146-0008-03US_SeqList.txt", a creation date of Aug. 3, 2016, and a size of 66,648 bytes. The sequence listing filed via EFS-Web is part of the specification and is hereby incorporated by reference in its entirety.

BACKGROUND

Ubiquitin is a small protein that has important regulatory roles in a wide variety of cellular pathways. The best known of these is ubiquitin's role in protein degradation, where covalent attachment of ubiquitin to a target protein enables that target protein to be recognized and destroyed by the 26S proteasome (see Wilkinson, Semin. Cell Devel. Biol. 11(3): 141-148 (2000)). Protein kinase regulation of various signaling pathways has also been correlated with ubiquitination (see Sun and Chen, Curr. Opin. Cell Biol. 16: 119-126 (2004)). For example, phosphorylation of IκB by IκB kinase permits ubiquitination of IκB and subsequent degradation by the 26S proteasome; because IκB is an inhibitor of NFκB, the degradation of IκB activates NFκB (Ghosh and Karin, Cell 109 (Suppl.): S81-S96 (2002); Palombella et al., Cell 78: 773-785 (1994)). Ubiquitination also mediates DNA repair (see Sun and Chen, Curr. Opin. Cell Biol. 16:119-126 (2004)). After DNA is damaged, monoubiquitination of proliferating cell nuclear antigen (PCNA) activates damage-tolerant polymerases which are able to synthesize DNA despite any DNA lesions (Stelter and Ulrich, Nature 425: 188-191 (2003). Other physiological processes in which ubiquitination is known to be involved include cell division, cell growth, cell movement, and apoptosis/cell death (Johnson, Nat. Cell Biol. 4:E295-E298 (2002); Pickart, Mol. Cell. 8: 499-504 (2001)).

The covalent attachment of ubiquitin, a 76 amino acid protein, to a target protein is a three-step enzymatic process (Pickart, Annu. Rev. Biochem. 70: 503-533 (2001)). First, ubiquitin-activating enzyme E1 forms an ubiquitin-E1 thioester in an ATP-dependent reaction. The ubiquitin is transferred from the ubiquitin-E1 thioester to a member of the ubiquitin-conjugating enzyme (E2) family in the second step. In the third step, with the assistance of a ubiquitin-protein ligase (E3), an isopeptide bond is formed between the carboxyl terminus of ubiquitin and the ε-amino group of a lysine residue on the target protein. Enzymes termed deubiquitinases remove ubiquitin moieties from target proteins (Guterman and Glickman, Curr. Prot. Pep. Sci. 5: 201-210 (2004)). Highlighting ubiquitin's role as an important regulatory molecule, the human genome contains many different proteins involved in ubiquitination or deubiquitination: at least 40 different E2s, 500 different E3s, and 80 different deubiquitinases have been identified thus far (Wong et al., Drug. Discov. Today 8: 746-754 (2003)).

Ubiquitin contains seven lysine residues (Lys6, Lys11, Lys27, Lys33, Lys29, Lys48, and Lys63), and thus ubiquitin itself may serve as a target protein for ubiquitination (Peng et al., Nat. Biotechnol. 21: 921-926 (2003); Pickart and Fushman, Curr. Opin. Chem. Biol. 8:610-616 (2004)). The molecule produced upon ubiquitination of a ubiquitin protein is termed a polyubiquitin molecule, and may comprise two or more ubiquitin moieties. Ubiquitination of ubiquitin may theoretically occur at any of the seven lysine residues (Peng et al., Nat. Biotechnol. 21: 921-926 (2003)), so that different species of polyubiquitins exist having isopeptide bonds to different lysine residues within ubiquitin. It is possible that a single polyubiquitin molecule with greater than two ubiquitin moieties may have more than one type of lysine linkage. Studies have shown that the E2 enzyme influences the type of lysine linkage created between one ubiquitin molecule and another (Tenno et al., Genes to Cells 9: 865-875 (2004); Deng et al. (2000); Hofmann and Pickart (2001)). Polyubiquitin and ubiquitin exist both as free molecules and in covalent attachment with a target protein.

Like ubiquitin, polyubiquitin involvement has been found in many cellular processes, including intracellular trafficking, endocytosis, gene expression/silencing, proteolysis, kinase activation, translation, and DNA repair (Hoege et al., Nature 419:135-141 (2002); Spence et al., Mol. Cell. Biol. 15:1265-1273 (1995); Hofmann and Pickart, Cell 96: 645-653 (1999). Polyubiquitin and polyubiquitination can have strikingly different physiological roles than monoubiquitin and monoubiquitination in the same pathways, however. For example, whereas monoubiquitination of PCNA after DNA damage results in the activation of error-prone DNA polymerases, polyubiquitination of PCNA at the identical residue where monoubiquitination is observed results in activation of error-free DNA repair (Stelter and to Ulrich, Nature 425: 188-191 (2003); Hoege et al., Nature 419:135-141 (2002); Spence et al., Mol. Cell. Biol. 15:1265-1273 (1995); and Hofmann and Pickart, Cell 96: 645-653 (1999)).

Even polyubiquitins having different lysine linkages appear to play different physiological roles. The two best-studied are the Lys48-linked and Lys63-linked polyubiquitins, and structural studies of the two suggest that different lysine-linked polyubiquitins may adopt markedly different conformations, thus permitting different interactions with selected binding partners (Tenno et al., Genes to Cells 9: 865-875 (2004)). Covalent modification by Lys48-linked polyubiquitin typically marks the target protein for proteolytic degradation, though there is some evidence that Lys48-linked polyubiquitin may also regulate certain proteins by non-proteolytic means (Chau et al., Science 243: 1576-1583 (1989); Finley et al., Mol. Cell. Biol. 14: 5501-5509 (1994); Flick et al., Nat. Cell. Biol. 6:634-641 (2004)). Lys63-linked polyubiquitins, in contrast, have been linked to a variety of nonproteolytic intracellular pathways, including DNA repair (yeast cells expressing K63R-ubiquitin are defective in DNA repair), kinase activation, intracellular trafficking, and translation (Pickart and Fushman, Curr. Opin. Chem. Biol. 8: 610-616 (2004); Hicke and Dunn, Annu Rev. Cell Dev. Biol. 19: 141-172 (2003); Spece et al., Mol. Cell Biol. 15: 1265-1273 (1995); Ulrich, Eukaryot. Cell 1: 1-10 (2002); Spence et al., Cell 102: 67-76 (2000); Seibenhener et al., Mol. Cell. Biol. 24(18): 8055-8068 (2004)). In one specific example, synphilin-1 is normally ubiquitinated with K63-linked polyubiquitin by parkin in a proteasomal-independent manner, but synphilin-1 can alternately be targeted for destruction by ubiquitination with K48-linked polyubiquitin (Lim et al., J. Neurosci. 25(8): 2002-9 (2005)). An analysis of subjects with Parkinson's disease shows that K63-polyubiquitination of synphilin-1 may be involved in the formation of Lewy body inclusions associated with that disease (Lim et al., J. Neurosci. 25(8): 2002-9 (2005)).

Other lysine-linked polyubiquitins have not been studied extensively, largely because of the difficulty in distinguishing between them. Studies have thus far relied on cells expressing mutagenized ubiquitins in which one or more lysines have been removed, on enzymatically synthesized polyubiquitins of particular linkages, or on techniques such as mass spectrometry to distinguish between one type of polyubiquitin and another. Each of those methodologies is ill-suited or cumbersome for analysis of the normal physiological behavior of particular lysine-linked polyubiquitins. While antibodies exist that are specific for polyubiquitin as opposed to monoubiquitin (Fujimoro et al., FEBS Lett. 349: 173-180 (1994)), there are as yet no antibodies that can distinguish between polyubiquitins of different lysine linkages.

Unsurprisingly, given their important roles in a variety of cellular processes, ubiquitin and polyubiquitins have also been implicated in many diseases (see Argiles, Ubiquitin and Disease, R. G. Landes (1998)). Ubiquitin dysregulation is observed in muscle wasting (Mitch and Goldberg, New Engl. J. Med. 335: 1897-905 (1996); Bodine et al., Science 294: 1704-1708 (2001)). Several genetic diseases have been linked to aberrant ubiquitin activity, including cystic fibrosis (Ward et al., Cell 83: 121-127 (1995)), Angelman's syndrome (Kishino et al., Nature Genet. 15: 70-73 (1997)), and Liddle syndrome (Staub et al., EMBO J 16: 6325-6336 (1997)). Ubiquitin also plays a role in immune and inflammatory responses; for example, extracellular ubiquitin has been found to act as a sort of cytokine, inhibiting the TNFα response to endotoxin in peripheral blood mononuclear cells and regulating endotoxin hyporesponsiveness (Majetschak et al., Blood 101: 1882-1890 (2003); Ciechanover, EMBO J 17: 7151-7160 (1998)). Also, both ubiquitin and polyubiquitin have been found in human serum, with higher levels of both molecules observed in the serum of patients having parasitic and allergic disease (Takada et al., Clinical Chem. 43: 1188-1195 (1997)).

Dysregulation of several ubiquitin-mediated pathways are also involved in cancer (Spataro et al., Br. J. Cancer 77: 448-55 (1998); Beckmann et al., Hum. Mutat. 25: 507-12 (2005)). For example, mutations in the heterodimeric ubiquitin ligase BRCA1-BARD1 are correlated with breast cancer (Hashizume et al., J. Biol. Chem. 276: 14537-40 (2001)), mutations that disrupt the ability of Myc to be degraded by the ubiquitin pathway activate the oncogenic potential of c-Myc (Salghetti et al., EMBO J. 18: 717-726 (1999)), and transformed v-Jun is unable to be ubiquitinated and degraded as its non-oncogenic correlate, c-Jun, is, giving rise to uncontrolled growth (Ciechanover, EMBO J. 17: 7151-7160 (1998); Trier et al., Cell 78: 787-798 (1994)).

Ubiquitin and polyubiquitin have particularly been studied in the context of neurological diseases (Chung et al., TINS 24(11 Suppl.) S7-S14 (2001)). The inclusions, bodies, and neurofibrillary tangles that accumulate in Huntington's disease, Spinocerebellar ataxia, prion encephalopathies, Pick's disease, Lewy body disease, Parkinson's disease, and Alzheimer's disease stain immunopositively for mono and/or polyubiquitin (Alves-Rodrigues et al., Trends Neurosci. 21: 516-520 (1998); Cammarata et al., Neurosci Lett. 156: 96-98 (1993); Kalchman et al., J. Biol. Chem. 271: 19385-94 (1996); Holmberg et al., Human Mol. Genet. 7: 913-918 (1998); Yedidia et al., EMBO J. 20: 5383-91 (2001); Mori et al., Science 235: 1641-44 (1987); Leigh et al., Acta Neuropathol. (Berl.) 79: 61-72 (1989); and Kuzuhara et al., Acta Neuropathologica 75: 345-353 (1988)). Several forms of Parkinson's disease have been linked to mutations in the ubiquitin carboxy-terminal hydrolase L1 (UCH-L1) gene, a deubiquitinase (Leroy et al., Nature 395: 451-452 (1998)), while other forms of Parkinson's have been linked to inactivating mutations in Parkin, an E2-dependent ubiquitin-protein ligase known to interact with the ubiquitin-conjugating enzyme UbcH7 and to ubiquitinate synphilin-1 (Shimura et al., Nature Genet. 25: 302-305 (2000), Zhang et al., Proc. Natl. Acad. Sci. 97: 13354-13359 (2000); Lim et al., J. Neurosci. 25(8): 2002-9 (2005)). Both types of mutations result in aberrant proteolytic processing and the inappropriate aggregation of proteins (see McNaught et al., Nature Rev. Neurosci. 2: 589-594 (2001)). UCH-L1 mutations have also been found to segregate with Huntington's disease (Naze et al., Neurosci. Lett. 328: 1: 1-4 (2002)). A mutant form of ubiquitin has been identified in the brains of Alzheimer's patients that is very efficiently incorporated into polyubiquitin chains, but is refractory to deubiquitination once formed, potentially leading to dominant inhibition of the normal cellular proteolytic processing system (Lam et al., Proc. Natl. Acad. Sci. 97: 9902-9906 (2000)).

It is clear that it would be beneficial not only to have compositions and methods that can distinguish between polyubiquitins of different lysine linkages, but also to have compositions and methods that are effective in targeting and modulating ubiquitin and polyubiquitin-mediated pathways. The invention provided herein relates to such compositions and methods.

All references cited herein, including patent applications and publications, are incorporated by reference in their entirety.

SUMMARY OF THE INVENTION

The invention provides novel antibodies capable of binding to and/or regulating biological activities associated with polyubiquitin.

In one embodiment, the invention provides an isolated antibody or antigen-binding fragment thereof that specifically binds to K63-linked polyubiquitin, wherein the antibody does not specifically bind to K48-linked polyubiquitin or monoubiquitin. In one aspect, the invention provides an isolated antibody or antigen-binding fragment comprising at least one hypervariable (HVR) sequence selected from HVR-H2 and HVR-L2 of any of SEQ ID NOs: 59-110 and 112, and 7-58 and 111, respectively.

In another embodiment, the invention provides an isolated antibody or antigen-binding fragment that specifically binds to K63-linked polyubiquitin, wherein the antibody or antigen-binding fragment does not specifically bind to K48- linked polyubiquitin or monoubiquitin, wherein the antibody or antigen-binding fragment comprises at least one HVR-H2 sequence, wherein HVR-H2 comprises the amino acid sequence a b c d e f g h i j k l m n o p (SEQ ID NO: 221), and wherein amino acid a is selected from the amino acids tyrosine, aspartic acid and tryptophan; amino acid b is isoleucine; amino acid c is selected from the amino acids serine, threonine, alanine, phenylalanine, tyrosine, and valine; amino acid d is proline; amino acid e is tyrosine; amino acid f is selected from the amino acids tyrosine, phenylalanine, leucine, and histidine; amino acid g is glycine; amino acid h is selected from the amino acids serine, glycine, alanine, phenylalanine, and tryptophan; amino acid I is threonine; amino acid j is serine; amino acid k is tyrosine; amino acid l is alanine; amino acid m is aspartic acid; amino acid n is serine; amino acid o is valine, and amino acid p is lysine.

In another embodiment, the invention provides an isolated antibody or antigen-binding fragment that specifically binds to K63-linked polyubiquitin, wherein the antibody does not specifically bind to K48-linked polyubiquitin or monoubiquitin, and wherein the antibody or antigen-binding fragment comprises at least one HVR-H2 sequence selected from the HVR-H2 sequences of SEQ ID NOs: 59-110 and 112. In one aspect, the antibody or antigen-binding fragment comprises at least one HVR-H2 sequence selected from the HVR-H2 sequences of SEQ ID NOs: 60, 63, and 66.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, and wherein the antibody or antigen-binding fragment comprises at least one HVR-L2 sequence, wherein HVR-L2 comprises the amino acid sequence q r s t u v w x (SEQ ID NO: 222), wherein amino acid q is selected from the amino acids tyrosine and phenylalanine; amino acid r is selected from the amino acids alanine and serine; amino acid s is alanine; amino acid t is selected from the amino acids serine, arginine, valine, threonine, alanine, asparagine, and leucine; amino acid u is serine; amino acid v is leucine; amino acid w is tyrosine, and amino acid x is serine.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, and wherein the antibody or antigen-binding fragment comprises at least one HVR-L2 sequence selected from the HVR-L2 sequences of SEQ ID NOs: 7-58 and 111. In one aspect, the antibody or antigen-binding fragment comprises at least one HVR-L2 sequence selected from the HVR-L2 sequences of SEQ ID NOs: 8, 11, and 14.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, wherein the antibody or antigen-binding fragment comprises at least one sequence selected from HVR-H2 and HVR-L2, wherein HVR-H2 comprises the amino acid sequence a b c d e f g h i j k l m n o p (SEQ ID NO: 221), wherein amino acid a is selected from the amino acids tyrosine, aspartic acid and tryptophan; amino acid b is isoleucine; amino acid c is selected from the amino acids serine, threonine, alanine, phenylalanine, tyrosine, and valine; amino acid d is proline; amino acid e is tyrosine; amino acid f is selected from the amino acids tyrosine, phenylalanine, leucine, and histidine; amino acid g is glycine; amino acid h is selected from the amino acids serine, glycine, alanine, phenylalanine, and tryptophan; amino acid I is threonine; amino acid j is serine; amino acid k is tyrosine; amino acid l is alanine; amino acid m is aspartic acid; amino acid n is serine; amino acid o is valine, and amino acid p is lysine; and wherein HVR-L2 comprises the amino acid sequence q r s t u v w x (SEQ ID NO: 222), wherein amino acid q is selected from the amino acids tyrosine and phenylalanine; amino acid r is selected from the amino acids alanine and serine; amino acid s is alanine; amino acid t is selected from the amino acids serine, arginine, valine, threonine, alanine, asparagine, and leucine; amino acid u is serine; amino acid v is leucine; amino acid w is tyrosine, and amino acid x is serine.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, wherein the antibody or antigen-binding fragment comprises at least one HVR-H2 sequence and at least one HVR-L2 sequence, wherein HVR-H2 comprises the amino acid sequence a b c d e f g h i j k l m n o p (SEQ ID NO: 221), wherein amino acid a is selected from the amino acids tyrosine, aspartic acid and tryptophan; amino acid b is isoleucine; amino acid c is selected from the amino acids serine, threonine, alanine, phenylalanine, tyrosine, and valine; amino acid d is proline; amino acid e is tyrosine; amino acid f is selected from the amino acids tyrosine, phenylalanine, leucine, and histidine; amino acid g is glycine; amino acid h is selected from the amino acids serine, glycine, alanine, phenylalanine, and tryptophan; amino acid I is threonine; amino acid j is serine; amino acid k is tyrosine; amino acid l is alanine; amino acid m is aspartic acid; amino acid n is serine; amino acid o is valine, and amino acid p is lysine; and wherein HVR-L2 comprises the amino acid sequence q r s t u v w x (SEQ ID NO: 222), wherein amino acid q is selected from the amino acids tyrosine and phenylalanine; amino acid r is selected from the amino acids alanine and serine; amino acid s is alanine; amino acid t is selected from the amino acids serine, arginine, valine, threonine, alanine, asparagine, and leucine; amino acid u is serine; amino acid v is leucine; amino acid w is tyrosine, and amino acid x is serine.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, wherein the antibody or antigen-binding fragment comprises at least one HVR-H2 sequence selected from the HVR-H2 sequences of SEQ ID NOs: 59-110 and 112 and at least one HVR-L2 sequence selected from the HVR-L2 sequences of SEQ ID NOs: 7-58 and 111.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, wherein the antibody or antigen-binding fragment comprises at least one HVR-H2 sequence selected from the HVR-H2 sequences of SEQ ID NOs: 60, 63, and 66 and at least one HVR-L2 sequence selected from the HVR-L2 sequences of SEQ ID NOs: 8, 11, and 14.

In another embodiment, the invention provides an isolated antibody or antigen-binding fragment that specifically binds to K63-linked polyubiquitin, wherein the antibody or antigen-binding fragment does not specifically bind to K48-linked polyubiquitin or monoubiquitin, wherein the antibody or antigen-binding fragment comprises HVR amino acid sequences selected from the HVR-H2 and HVR-L2 amino acid sequences set forth for any one of Apu3.A8-Apu3.H10 in Table B. In one aspect, the HVR amino acid sequences are selected from the HVR-H2 and HVR-L2 amino acid sequences set forth for any one of Apu3.A8, Apu3.A12, and Apu3.B3 in Table B.

In one aspect, any of the foregoing antibody or antigen-binding fragments comprise at least one HVR sequence selected from the HVR-H1 sequence of SEQ ID NO: 5, the HVR-H3 sequence of SEQ ID NO: 6, the HVR-L1 sequence of SEQ ID NO: 3 and the HVR-L3 sequence of SEQ ID NO: 4. In another aspect, any of the foregoing antibody or antigen-binding fragments comprise at least two HVR sequences selected from the HVR-H1 sequence of SEQ ID NO: 5, the HVR-H3 sequence of SEQ ID NO: 6, the HVR-L1 sequence of SEQ ID NO: 3 and the HVR-L3 sequence of SEQ ID NO: 4. In another aspect, any of the foregoing antibody or antigen-binding fragments comprise at least three HVR sequences selected from the HVR-H1 sequence of SEQ ID NO: 5, the HVR-H3 sequence of SEQ ID NO: 6, the HVR-L1 sequence of SEQ ID NO: 3 and the HVR-L3 sequence of SEQ ID NO: 4. In another aspect, any of the foregoing antibody or antigen-binding fragments comprise the HVR-H1 sequence of SEQ ID NO: 5, the HVR-H3 sequence of SEQ ID NO: 6, the HVR-L1 sequence of SEQ ID NO: 3 and the HVR-L3 sequence of SEQ ID NO: 4.

In one aspect, any of the foregoing antibody or antigen-binding fragments have an affinity for K63-linked polyubiquitin improved relative to the affinity of the parental Fab Apu2.16 for K63-linked polyubiquitin. In another aspect, any of the foregoing antibody or antigen-binding fragments have Kd values for K63-linked polyubiquitin less than or equal to 10 nM.

In another embodiment, the invention provides an isolated antibody or antigen-binding fragment that binds to the same antigenic determinant on polyubiquitin as any of the foregoing antibody or antigen-binding fragments, wherein the antibody or antigen-binding fragment does not specifically bind to monoubiquitin. In another embodiment, the invention provides an isolated antibody or antigen-binding fragment that competes with any of the foregoing antibody or antigen-binding fragments for binding to polyubiquitin, wherein the antibody or antigen-binding fragment does not specifically bind to monoubiquitin.

In another embodiment, the invention provides an isolated antibody or antigen-binding fragment that binds to an epitope in K63-linked polyubiquitin. In one aspect, the epitope includes residues in both a first ubiquitin subunit and a second ubiquitin subunit of the K63-linked polyubiquitin. In another aspect, the epitope includes at least one residue in a first ubiquitin subunit selected from Glu-18, Pro-19, Ser-20, Asp-21, Thr-55, Leu-56, Ser-57, Asp-58, Asn-60, Ile-61, and Gln-62. In another aspect, the epitope includes at least one residue in a second ubiquitin subunit selected from Leu-8, Thr-9, Glu-34, Gly-35, Ile-36, Pro-37, Asp-39, Gln-40, Leu-71, Arg-72, Leu-73, Arg-74, and Gly-75. In another aspect, the epitope includes at least one residue in a first ubiquitin subunit selected from Glu-18, Pro-19, Ser-20, Asp-21, Thr-55, Leu-56, Ser-57, Asp-58, Asn-60, Ile-61, and Gln-62, and at least one residue in a second ubiquitin subunit selected from Leu-8, Thr-9, Glu-34, Gly-35, Ile-36, Pro-37, Asp-39, Gln-40, Leu-71, Arg-72, Leu-73, Arg-74, and Gly-75. In another aspect, the N-terminal portion of HVRH3 contacts C-terminal residues and Q40 from the donor ubiquitin. In another aspect, the distal part of HVRH3 contacts the 50s loop of the K63-acceptor ubiquitin. In another such aspect, the N-terminal portion of HVRH3 contacts C-terminal residues 72-74 and Q40 from the donor ubiquitin, while residues R102 and Y103 of HVRH3 contact the 50s loop of the K63-acceptor ubiquitin. In another aspect, C-terminal residues of the donor ubiquitin contact the antibody or antigen-binding fragment. In another such aspect, the donor ubiquitin residues involved in the contact are L73 and R74.

In another embodiment, the invention provides an isolated antibody or antigen-binding fragment comprising improved electrostatic compatibility between its light chain and the surface of a K63-acceptor ubiquitin. In one aspect, the antibody or antigen-binding fragment comprises an Arg at position 52 of HVRL2. In another aspect, the antibody or antigen-binding fragment comprises an Arg at position 66 of the light chain framework region. In another aspect, the antibody or antigen-binding fragment comprises an Arg at position 52 of HVRL2 and an Arg at position 66 of the light chain framework region.

In another embodiment, any of the foregoing antibodies or antigen-binding fragments specifically binds to a K63-linked polyubiquitinated protein. In one aspect, the antibody or antigen-binding fragment inhibits degradation of the K63-linked polyubiquitinated protein. In another aspect, the antibody or antigen-binding fragment modulates at least one polyubiquitin-mediated signaling pathway. In another aspect, the antibody or antigen-binding fragment inhibits at least one polyubiquitin-mediated signaling pathway. In another aspect, the antibody or antigen-binding fragment stimulates at least one polyubiquitin-mediated signaling pathway.

In another embodiment, the invention provides a nucleic acid molecule encoding any of the foregoing antibody or antigen-binding fragments. In another embodiment, the invention provides a vector comprising such a nucleic acid molecule. In another embodiment, the invention provides a host cell comprising such a vector. In another embodiment, the invention provides a cell line capable of producing any of the foregoing antibodies or antigen-binding fragments. In another embodiment, the invention provides a method of producing any of the foregoing antibodies or antigen-binding fragments, comprising culturing a host cell comprising a nucleic acid molecule encoding the antibody or antigen-binding fragment under conditions wherein the antibody or antigen-binding fragment is produced.

In another embodiment, the invention provides a composition comprising an effective amount of any of the foregoing antibodies or antigen-binding fragments and a pharmaceutically acceptable carrier. In one aspect, the composition comprises two or more of the foregoing antibodies or antigen-binding fragments.

In another embodiment, the invention provides a method of identifying the presence of K63-linked polyubiquitin or a K63-linked polyubiquitinated protein in a sample, comprising contacting the sample with at least one of the foregoing antibodies or antigen-binding fragments.

In another embodiment, the invention provides a method for the treatment of a disease or condition associated with dysregulation of polyubiquitin in a patient, the method comprising administering to the patient an effective amount of at least one of the foregoing antibodies or antigen-binding fragments. In one aspect, the patient is a mammalian patient. In another aspect, the patient is human. In another aspect, the disease is selected from cancer, a muscular disorder, a ubiquitin-pathway-related genetic disorder, an immune/inflammatory disorder, and a neurological disorder. In another aspect, the disease is selected from carcinoma, lymphoma, blastoma, sarcoma, leukemia, muscular dystrophy, multiple sclerosis, amyotrophic lateral sclerosis, cystic fibrosis, Angelman's syndrome, Liddle syndrome, Alzheimer's disease, Parkinson's disease, Pick's disease, and Paget's disease.

In another embodiment, the invention provides a method of determining the presence of a K63-linked polyubiquitin or a K63-linked polyubiquitinated protein in a sample suspected of containing a K63-linked polyubiquitin or K63-linked polyubiquitinated protein, comprising exposing the sample to at least one of the foregoing antibodies or antigen-binding fragments and determining the binding of the at least one antibody or antigen-binding fragment to a K63-linked polyubiquitin or K63-linked polyubiquitinated protein in the sample.

In another embodiment, the invention provides a method of separating K63-linked polyubiquitinated protein from non-K63-linked polyubiquitinated protein in a sample, comprising contacting the sample with at least one of the foregoing antibodies or antigen-binding fragments.

In another embodiment, the invention provides a method of determining the function and/or activity of K63-linked polyubiquitin in a cell comprising contacting the cell with at least one of the foregoing antibodies or antigen-binding fragments and assessing the effect of said contacting step on the cell. In another embodiment, the invention provides a method of determining the function and/or activity of K63-linked polyubiquitin in a sample comprising contacting the sample with at least one of the foregoing antibodies or antigen-binding fragments and assessing the effect of said contacting step on the sample.

An antibody of the invention can be in any number of forms. For example, an antibody of the invention can be a chimeric antibody, a humanized antibody or a human antibody. In one embodiment, an antibody of the invention is not a human antibody, for example it is not an antibody produced in a xenomouse (e.g., as described in WO96/33735). An antibody of the invention can be full length or a fragment thereof (e.g., a fragment comprising an antigen binding component).

In another embodiment, the invention provides an antigen-binding fragment of any of the above-described antibodies.

BRIEF DESCRIPTION OF THE DRAWINGS

FIGS. 1A-B show the primary structure of ubiquitin and schematic views of certain polyubiquitin isopeptide linkages. FIG. 1A shows the amino acid sequence of human ubiquitin (SEQ ID NO: 223), with the lysine residues indicated in bold, underlined text. FIG. 1B shows a schematic depiction of the bond formed between the lysine-48 or lysine-63 of a first ubiquitin molecule and the C-terminal glycine residue of a second ubiquitin molecule.

FIGS. 2A-E depict crystal structures of relevant molecules as discussed in Example 4. FIG. 2A depicts the complex between K63-linked diubiquitin (upper part of figure) and the Apu2.16 Fab fragment (lower part of figure, with the light chain on the left and the heavy chain on the right), and shows that the heavy chain CDR3 ("H3") contacts both ubiquitin chains on either side of the isopeptide linkage. H3 side chain within 4.2 Å of diubiquitin, and ubiquitin side chains within 4.2 Å of H3, are shown as sticks. Residues labeled in bold are ubiquitin residues while the other (non-bold) labeled residues are Fab residues. K63 in the acceptor ubiquitin is shown as a sphere. FIG. 2B depicts a comparison of K63-linked (upper) and K48-linked (lower) diubiquitin structures. In both cases, the lysine acceptor ubiquitin is to the left and the donor ubiquitin is to the right of the figure. The K48-linked diubiquitin forms a more compact shape with the chain extending perpendicular to the ubiquitin dimer as compared to the K63 dimer, where the chain extends in a more elongated manner. FIG. 2C is a superimposition of the Apu2.16 crystal structure shown in FIG. 2A superimposed on the crystal structure of Apu3.A8, showing the location of the two changes in L2 (S52R) and H3 (S52T) introduced during the affinity maturation process to create Apu3.A8. FIG. 2D shows a comparison of the structures of Apu2.16, Apu3.A8 and a variant of humanized 4D5 (pdb 1FVE). The Fv regions of Apu2.16 and Apu3.A8 are shown as tubes and superimposed on the Fv region of the humanized anti-Her2 antibody 4D5 variant. In the top view, the CDR regions are labeled; in the bottom view, the Fv regions are rotated by 90 degrees to show the N-termini. FIG. 2E depicts the charge complementarity between Apu3.A8 (lower) and diubiquitin (upper). Electrostatic surfaces were calculated with PyMol. Regions of positive potential are shaded; regions with negative potential are shaded and indicated with dotted lines.

FIG. 3A shows the binding of the parental anti-K63-linked polyubiquitin Fab Apu2.16 to immobilized K63-linked diubiquitin and the absence of binding to immobilized K48-linked diubiquitin. FIG. 3B shows the binding of anti-K63-linked polyubiquitin Fab Apu3.A8 to immobilized K63-linked diubiquitin and the absence of binding to immobilized K48-linked diubiquitin. FIG. 3C shows the binding of anti-K63-linked polyubiquitin Fab Apu3.A12 to immobilized K63-linked diubiquitin and the absence of binding to immobilized K48-linked diubiquitin. FIG. 3D shows the binding of anti-K63-linked polyubiquitin Fab Apu3.B3 to immobilized K63-linked diubiquitin and the absence of binding to immobilized K48-linked diubiquitin.

FIG. 7A depicts the results of mass spectrometry experiments to confirm that the proteins immunoprecipitated by affinity-matured antibodies Apu3.A8, Apu3.B3, and Apu3.A12 were mainly K63-linked ubiquitinated, as described in Example 2. FIG. 7B shows that the K48 linkage was not enriched using this approach, hence showing specificity of the K63 antibody towards the K63 chain linkage. FIGS. 7C-F show bar graphs of data obtained from immunoprecipitation experiments using anti-K48-linked polyubiquitin antibody Apu2.07, anti-K63-linked polyubiquitin antibody Apu3.A8, or an isotype control antibody (anti-Her2), followed by mass spectrometric analysis to determine the total amount of ubiquitin immunoprecipitated (FIG. 7C), as well as the types of polyubiquitin linkages present in the lysate (FIG. 7D) and antibody-specific immunoprecipates (anti-K48-linked polyubiquitin in FIG. 7E; anti-K63-linked polyubiquitin in FIG. 7F). FIG. 7G schematically depicts the MuRF1 autoubiquitination reactions performed in vitro with WT, K48R or K63R ubiquitin followed by immunoprecipitation with Apu2.07, Apu3.A8, or an isotype-matched control antibody. The numbers in parentheses indicate the relevant lanes and columns in FIGS. 7H-K. FIG. 7H shows a western blot including the reactions depicted schematically in FIG. 7G. The blot was probed with a pan-ubiquitin antibody. The horizontal dotted lines indicate the portion of the gel that was cut out and subjected to analysis by mass spectrometry. FIGS. 7I-K show bar graphs of the mass spectrometry data obtained from the experiments to determine the polyubiquitin linkages in the autoubiquitination reactions and immunoprecipitations depicted schematically in FIG. 7G.

FIG. 10C shows western blots assessing IRAK1 that is modified by K48-linked polyubiquitin (top panel) or K63-linked polyubiquitin (lower panel). FIG. 10D shows a western blot indicating the effect of the protease inhibitor MG-132 on degradation of polyubiquitinated IRAK1.

FIGS. 12A and 12B and FIG. 13 depict exemplary acceptor human consensus framework sequences for use in practicing the instant invention with sequence identifiers as follows:

Variable Heavy (VH) Consensus Frameworks (FIGS. 12A and 12B)

Human VH subgroup I consensus framework minus Kabat CDRs (SEQ ID NOs: 113-116)
Human VH subgroup I consensus framework minus extended hypervariable regions (SEQ ID NOs: 117-128)
Human VH subgroup II consensus framework minus Kabat CDRs (SEQ ID NOs: 129-132)
Human VH subgroup II consensus framework minus extended hypervariable regions (SEQ ID NOs: 133-144)
Human VH subgroup III consensus framework minus Kabat CDRs (SEQ ID NOs: 145-148)
Human VH subgroup III consensus framework minus extended hypervariable regions (SEQ ID NOs: 149-160)
Human VH acceptor framework minus Kabat CDRs (SEQ ID NOs: 161-164)
Human VH acceptor framework minus extended hypervariable regions (SEQ ID NOs: 165-172)
Human VH acceptor 2 framework minus Kabat CDRs (SEQ ID NOs: 173-176) Human VH acceptor 2 framework minus extended hypervariable regions (SEQ ID NOs: 177-188)

Figure 13:

Variable Light (VL) Consensus Frameworks (FIG. 13)

Human VL kappa subgroup I consensus framework (SEQ ID NOs: 189-192)
Human VL kappa subgroup II consensus framework (SEQ ID NOs: 193-196)
Human VL kappa subgroup III consensus framework (SEQ ID NOs: 197-200)
Human VL kappa subgroup IV consensus framework (SEQ ID NOs: 201-204)

FIG. 14 depicts framework region sequences of huMAb4D5-8 light and heavy chains. Numbers in superscript/bold indicate amino acid positions according to Kabat.

FIG. 15 depicts modified/variant framework region sequences of huMAb4D5-8 light and heavy chains. Numbers in superscript/bold indicate amino acid positions according to Kabat.

MODES FOR CARRYING OUT THE INVENTION

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", third edition (Sambrook et al., 2001);

"Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); PCR 2: A Practical Approach (M. J. MacPherson, B. D. Hames and G. R. Taylor eds. (1995)); Harlow and Lane, eds. (1988) Antibodies, A Laboratory Manual; "A Practical Guide to Molecular Cloning" (Perbal Bernard V., 1988); and "Phage Display: A Laboratory Manual" (Barbas et al., 2001).

Definitions

As used herein, the terms "ubiquitin" and "monoubiquitin" are used interchangeably, and are defined as all species of native human and synthetic ubiquitin substantially similar to a 76-amino acid protein having at least one lysine residue at amino acid 6, amino acid 11, amino acid 27, amino acid 29, amino acid 33, amino acid 48, and/or amino acid 63.

As used herein, the term "polyubiquitin" is defined as all species of native human and synthetic polymeric chains of ubiquitin which fall within human and synthetic classes of different polymeric linkages of ubiquitin, including, but not limited to, K6-linked polyubiquitin, K11-linked polyubiquitin, K27-linked polyubiquitin, K29-linked polyubiquitin, K33-linked polyubiquitin, K48-linked polyubiquitin and K63-linked polyubiquitin. Polyubiquitin may be of any length, and includes at least two ubiquitin moieties. Polyubiquitin is distinguished from tandem repeats of ubiquitin that are originally expressed as a single protein.

As used herein, the terms "K*-linked polyubiquitin" and "Lys*-linked polyubiquitin" are interchangeable, and refer to a polyubiquitin molecule comprising at least one isopeptide bond between the C-terminus of one ubiquitin moiety and a lysine at position * in another ubiquitin moiety. For example, a "K63-linked polyubiquitin" is used interchangeably with a "Lys63-linked polyubiquitin", and both terms refer to a polyubiquitin molecule comprising an isopeptide bond between the C-terminus of one of the ubiquitin moieties in the molecule and the lysine at position 63 in another ubiquitin moiety in the molecule.

As used herein, a statement that a first lysine linkage "differs" from a second lysine linkage indicates that the first lysine linkage between one ubiquitin moiety and another ubiquitin moiety involves a different lysine residue (e.g., K6, K11, K27, K29, K33, K48, and/or K63) than the second lysine linkage between one ubiquitin moiety and another ubiquitin moiety.

As used herein, the term "ubiquitin pathway" refers to a biochemical pathway in a cell or reconstituted in vitro that includes ubiquitin and/or polyubiquitin.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

As used herein, the terms "anti-ubiquitin antibody" and "anti-monoubiquitin antibody" are used interchangeably, and refer to an antibody that is capable of specifically binding to a ubiquitin molecule.

As used herein, the term "anti-polyubiquitin antibody" refers to an antibody that is capable of specifically binding to a polyubiquitin molecule.

As used herein, the term "anti-K48-linked polyubiquitin antibody" refers to an antibody that is capable of specifically binding to K48-linked polyubiquitin.

As used herein, the term "anti-K63-linked polyubiquitin antibody" refers to an antibody that is capable of binding to K63-linked polyubiquitin.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a nonadsorbent plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (-0.2 µM) before injection at a flow rate of 5 µl/minute to achieve approximately 10 response units (RU) of coupled protein. Following the injection of antigen, 1 M ethanolamine is injected to block unreacted groups. In each experiment, a spot was activated and ethanolamine blocked without immobilizing protein, to be used for reference subtraction. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

An "on-rate" or "rate of association" or "association rate" or "$k_{on}$," according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, $2^{nd}$ ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B (Kabat Numbering) | H26-H35B | H26-H32 | H30-H35B |
| H1 | H31-H35 (Chothia Numbering) | H26-H35 | H26-H32 | H30-H35 |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 or 49-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer, muscular disorders, ubiquitin-pathway-related genetic disorders, immune/inflammatory disorders, neurological disorders, and other ubiquitin pathway-related disorders.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "muscular disorder" refers to or describes the physiological condition in muscle-containing animals that is typically characterized by deterioration or weakening of skeletal and/or smooth muscle such that normal muscular function is significantly reduced. Examples of muscular disorders include, but are not limited to, muscular dystrophy, multiple sclerosis, amyotrophic lateral sclerosis, Isaac's syndrome; stiff-person syndrome; familiar periodic paralyses, myopathy, myotonia, rhabdomyolyses, muscle atrophy, and various types of muscle weakness and muscle rigidity.

The term "ubiquitin pathway-related genetic disorder" refers to or describes a genetically-based disorder that is typically characterized by or contributed to by aberrant functioning of the ubiquitin pathway. Examples of ubiquitin pathway-related genetic disorders include, but are not limited to, cystic fibrosis, Angelman's syndrome, and Liddle syndrome.

The terms "neurological disorder" or "neurological disease" refer to or describe a disease or disorder of the central and/or peripheral nervous system in mammals that is typically characterized by deterioration of nervous tissue or deterioration of communication between cells in nervous tissue. Examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia.

The terms "inflammatory disorder" and "immune disorder" refer to or describe disorders caused by aberrant immunologic mechanisms and/or aberrant cytokine signaling. Examples of inflammatory and immune disorders include, but are not limited to, autoimmune diseases, immunologic deficiency syndromes, and hypersensitivity. An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitus); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia) ; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

Examples of immunologic deficiency syndromes include, but are not limited to, ataxia telangiectasia, leukocyte-adhesion deficiency syndrome, lymphopenia, dysgammaglobulinemia, HIV or deltaretrovirus infections, common variable immunodeficiency, severe combined immunodeficiency, phagocyte bactericidal dysfunction, agammaglobulinemia, DiGeorge syndrome, and Wiskott-Aldrich syndrome. Examples of hypersensitivity include, but are not limited to, allergies, asthma, dermatitis, hives, anaphylaxis, Wissler's syndrome, and thrombocytopenic purpura.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Compositions and Methods of Making Same

The present invention provides antibodies that bind specifically to polyubiquitin, but not to monoubiquitin. More specifically, antibodies that are capable of binding specifically to a polyubiquitin comprising a K63 linkage but not to a polyubiquitin comprising a second, different, lysine linkage are provided. The antibodies of the invention provide surprisingly improved affinity for K63-linked polyubiquitin over previously known antibodies. This improved affinity enables their broad use in a variety of assays where tight binding of the antibody to K63-linked polyubiquitinated protein is a prerequisite, such as immunoprecipitation reactions. The antibodies of the invention are also better suited for use as therapeutics than previously identified anti-K63-linked polyubiquitin-specific antibodies because they may potentially be administered at lower dosages or less frequently than an antibody with a lesser affinity for the same K63-linked polyubiquitin.

In one aspect, the invention provides an antibody comprising an HVR-H2 region comprising the sequence of at least one of SEQ ID NOs: 60-110. In one aspect, the invention provides an antibody comprising an HVR-H2 region consensus sequence of SEQ ID NO: 112.

In one aspect, the invention provides an antibody comprising an HVR-L2 region comprising the sequence of at least one of SEQ ID NOs: 8-58. In one aspect, the invention provides an antibody comprising a HVR-L3 region consensus sequence of SEQ ID NO: 111.

In one aspect, the invention provides an antibody comprising at least one or at least two of the following:
(i) an HVR-H2 sequence comprising at least one sequence of SEQ ID NOs: 60-110;
(ii) an HVR-L2 sequence comprising at least one sequence of SEQ ID NOs: 8-58.

In one aspect, the invention provides an antibody that specifically binds K63-linked polyubiquitin with high affinity but binds K48-linked polyubiquitin with substantially reduced affinity, comprising at least one or at least two of the following:
(i) an HVR-H2 sequence comprising at least one sequence of SEQ ID NOs: 60-110;
(ii) an HVR-L2 sequence comprising at least one sequence of SEQ ID NOs: 8-58.

The amino acid sequences of SEQ ID NOs: 8-112 are numbered with respect to individual HVR (i.e., H2, L2) as indicated in Table B, the numbering being consistent with the Kabat numbering system as described below. In one embodiment, an antibody of the invention comprises one or two of the HVR sequences of (i)-(ii) above, and at least one of HVR-L1 of SEQ ID NO: 3, HVR-L3 of SEQ ID NO: 4, HVR-H1 of SEQ ID NO: 5, and HVR-H3 of SEQ ID NO: 6.

In one aspect, the invention provides antibodies comprising heavy chain HVR H2 sequences as set forth in Table B. In one embodiment, the antibodies further comprise light chain HVR-L2 sequences as set forth in Table B.

Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340(5):1073-93) as depicted in SEQ ID NO: 224 below.

(SEQ ID NO: 224)

Asp¹ Ile Gln Met Thr Gln Ser Pro Ser Ser Leu Ser Ala Ser Val Gly

Asp Arg Val Thr Ile Thr Cys Arg Ala Ser Gln Asp Val Asn Thr Ala

Val Ala Trp Tyr Gln Gln Lys Pro Gly Lys Ala Pro Lys Leu Leu Ile

Tyr Ser Ala Ser Phe Leu Tyr Ser Gly Val Pro Ser Arg Phe Ser Gly Ser

Arg Ser Gly Thr Asp Phe Thr Leu Thr Ile Ser Ser Leu Gln Pro Glu

```
Asp Phe Ala Thr Tyr Tyr Cys Gln Gln His Tyr Thr Thr Pro Pro Thr

Phe Gly Gln Gly Thr Lys Val Glu Ile Lys 107
```

(HVR residues are underlined)

In one embodiment, the huMAb4D5-8 light chain variable domain sequence is modified at one or more of positions 28, 30, 31, 42, 53, 66, and 91-96 (Asp, Asn, Thr, Lys, Phe, Arg, His, Tyr, Thr, Thr, Pro, and Pro as indicated in bold/italics above, respectively). In one embodiment, the modified huMAb4D5-8 sequence comprises Ser in position 28, Ser in position 30, Ser in position 31, Glu in position 42, Ser in position 53, Gly in position 66, Tyr in position 91, Ser in position 92, Ser in position 93, Tyr in position 94, Ser in position 95, Ser in position 96, and/or an insertion of Leu and Phe between the Ser at position 96 and the Thr at position 97. In another embodiment, the modified huMAb4D5-8 sequence comprises an inserted Ser just prior to position 1 (i.e., at the N-terminus of the protein), a Ser in position 28, Ser in position 30, Ser in position 31, Glu in position 42, Ser in position 53, Gly in position 66, Tyr in position 91, Ser in position 92, Ser in position 93, Tyr in position 94, Ser in position 95, Ser in position 96, and/or an insertion of Leu and Phe between the Ser at position 96 and the Thr at position 97. Accordingly, in one embodiment, an antibody of the invention comprises a light chain variable domain comprising the sequence depicted in SEQ ID NO: 225 below:

```
                                                      (SEQ ID NO: 225)
Ser⁻¹ Asp¹ Ile Gln Met Thr Gln Ser Pro Ser Ser Leu Ser Ala Ser Val

Gly Asp Arg Val Thr Ile Thr Cys Arg Ala Ser Gln Ser Val Ser Ser Ala

Val Ala Trp Tyr Gln Gln Lys Pro Gly Glu Ala Pro Lys Leu Leu Ile

Tyr Ser Ala Ser Ser Leu Tyr Ser Gly Val Pro Ser Arg Phe Ser Gly Ser

Gly Ser Gly Thr Asp Phe Thr Leu Thr Ile Ser Ser Leu Gln Pro Glu

Asp Phe Ala Thr Tyr Tyr Cys Gln Gln Tyr Ser Ser Tyr Ser Ser Leu

Phe Thr Phe Gly Gln Gly Thr Lys Val Glu Ile Lys
```

(HVR residues are underlined)

Substituted residues with respect to huMAb4D5-8 are indicated in bold/italics above.

Certain embodiments of antibodies of the invention comprise a heavy chain variable domain having the following sequence:

```
                                                      (SEQ ID NO: 226)
Glu Ile Ser Glu Val Gln Leu Val Glu Ser Gly Gly Gly Leu Val Gln

Pro Gly Gly Ser Leu Arg Leu Ser Cys Ala Ala Ser Gly Phe Asn Val

Lys Thr Gly Leu Ile His Trp Val Arg Gln Ala Pro Gly Lys Gly Leu

Glu Trp Val Ala Tyr Ile Ser Pro Tyr Tyr Gly Ser Thr Ser

Thr Ser Tyr Ala Asp Ser Val Lys Gly Arg Phe Thr Ile Ser Ala Asp

Thr Ser Lys Asn Thr Ala Tyr Leu Gln Met Asn Ser Leu Arg Ala Glu

Asp Thr Ala Val Tyr Tyr Cys Ala Arg Glu Tyr Tyr Arg Trp Tyr Thr

Ala Ile Asp Tyr Trp Gly Gln Gly Thr Leu Val Thr Val Ser Ser
```

(HVR residues are underlined)

In one embodiment, the heavy chain variable domain sequence is modified at the bold, italicized position. In another embodiment, the bold, italicized Ser is modified to Thr. In another embodiment, the first three residues of the heavy chain variable domain sequence set forth in SEQ ID NO: 226 are not present.

In another embodiment, an antibody of the invention comprises a heavy chain variable domain having the following sequence:

(SEQ ID NO: 227)
Glu Ile Ser Glu Val Gln Leu Val Glu Ser Gly Gly Gly Leu Val Gln

Pro Gly Gly Ser Leu Arg Leu Ser Cys Ala Ala Ser Gly Phe Asn <u>Val</u>

<u>Lys Thr Gly Leu Ile</u> His Trp Val Arg Gln Ala Pro Gly Lys Gly Leu

Glu Trp Val Ala <u>Tyr Ile Thr Pro Tyr Tyr Gly Ser Thr Ser</u> Thr

Ser Tyr Ala Asp Ser Val Lys Gly Arg Phe Thr Ile Ser Ala Asp Thr

Ser Lys Asn Thr Ala Tyr Leu Gln Met Asn Ser Leu Arg Ala Glu Asp

Thr Ala Val Tyr Tyr Cys Ala Arg <u>Glu Tyr Tyr Arg Trp Tyr Thr Ala</u>

<u>Ile</u> Asp Tyr Trp Gly Gln Gly Thr Leu Val Thr Val Ser Ser (HVR residues are underlined)

In another embodiment, an antibody of the invention comprises a heavy chain variable domain having the following sequence:

(SEQ ID NO: 228)
Glu Val Gln Leu Val Glu Ser Gly Gly Gly Leu Val Gln Pro Gly Gly

Ser Leu Arg Leu Ser Cys Ala Ala Ser Gly Phe Asn <u>Val Lys Thr Gly</u>

<u>Leu Ile</u> His Trp Val Arg Gln Ala Pro Gly Lys Gly Leu Glu Trp Val

Ala <u>Tyr Ile Thr Pro Tyr Tyr Gly Ser Thr Ser</u> Tyr Ala Asp Ser

Val Lys Gly Arg Phe Thr Ile Ser Ala Asp Thr Ser Lys Asn Thr Ala

Tyr Leu Gln Met Asn Ser Leu Arg Ala Glu Asp Thr Ala Val Tyr Tyr

Cys Ala Arg <u>Glu Tyr Tyr Arg Trp Tyr Thr Ala Ile</u> Asp Tyr Trp Gly

Gln Gly Thr Leu Val Thr Val Ser Ser (HVR residues are underlined)

Antibodies of the invention can comprise any suitable framework variable domain sequence, provided binding activity to polyubiquitin including a particular lysine linkage is substantially retained. For example, in some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93). In one embodiment, these antibodies further comprise a human κI light chain framework consensus sequence. In one embodiment, these antibodies comprise at least one, two or more of the light chain HVR sequences of SEQ ID NOs: 3, 4, 8-58, and 111. In one embodiment, these antibodies comprise light chain HVR sequences of huMAb4D5-8 as described in U.S. Pat. Nos. 6,407,213 & 5,821,337. In one embodiment, these antibodies comprise light chain variable domain sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5): 1073-93).

In one embodiment, an antibody of the invention comprises a heavy chain variable domain, wherein the framework sequence comprises the sequence of at least one of SEQ ID NOs: 113-188, 209-212, and 217-220, the HVR H1 sequence is SEQ ID NO: 5, the HVR H2 sequence is selected from at least one of SEQ ID NOs: 59-110 and 112; and the HVR H3 sequence is SEQ ID NO: 6. In one embodiment, an antibody of the invention comprises a light chain variable domain, wherein the framework sequence comprises the sequence of at least one of SEQ ID NOs: 189-204, 205-208, and 213-216, the HVR-L1 sequence is SEQ ID NO: 3, the HVR-L2 sequence is selected from at least one of SEQ ID NOs: 8-58 and 111, and the HVR-L3 sequence is SEQ ID NO: 4.

In one embodiment, an antibody of the invention comprises a heavy chain variable domain, wherein the framework sequence comprises at least one sequence of SEQ ID NOs: 113-188, and HVR H1, H2 and H3 sequences are SEQ ID NOs: 5, 60, and 6, respectively (clone Apu3.A8). Similarly, in other embodiments, antibodies of each of clones Apu3.A9-H10 as set forth on Table B herein comprise a heavy chain variable domain, wherein the framework sequence comprises at least one sequence of SEQ ID NOs: 113-188, and HVR-H1 is SEQ ID NO: 5, HVR-H2 sequences are those sequences specifically enumerated for each clone in Table B, and HVR-H3 is SEQ ID NO: 6. In one embodiment, an antibody of the invention comprises a light chain variable domain, wherein the framework sequence comprises at least one sequence of SEQ ID NOs: 189-204, and HVR L1, L2 and L3 sequences are SEQ ID NOs: 3, 8, and 4, respectively (Apu3.A8). Similarly, in other embodiments, antibodies of each of clones Apu3.A9-H10 as set forth on Table B herein comprise a light chain variable domain, wherein the framework sequence comprises at least one sequence of SEQ ID NOs: 189-204, and HVR-L1 is SEQ ID NO: 3, HVR-L2 sequences are those sequences specifically enumerated for each clone in Table B, and HVR-L3 is SEQ ID NO: 4.

In one embodiment, an antibody of the invention comprises a heavy chain variable domain, wherein the framework sequence comprises at least one sequence of SEQ ID NOs: 209-212, and HVR H1, H2 and H3 sequences are SEQ ID NOs: 5, 60, and 6, respectively (clone Apu3.A8). Similarly, in other embodiments, antibodies of each of clones Apu3.A9-H10 comprise a heavy chain variable domain, wherein the framework sequence comprises at least one sequence of SEQ ID NOs: 209-212, and HVR-H1 is SEQ ID NO: 5, HVR-H2 sequences are those sequences specifically enumerated for each clone in Table B, and HVR-H3 is SEQ ID NO: 6. In one embodiment, an antibody of the invention comprises a light chain variable domain, wherein the framework sequence comprises at least one sequence of SEQ ID NOs: 205-208, and HVR L1, L2 and L3 sequences are SEQ ID NOs: 3, 8, and 4, respectively (Apu3.A8). Similarly, in other embodiments, antibodies of each of clones Apu3.A9-H10 shown in Table B comprise a light chain variable domain, wherein the framework sequence comprises at least one sequence of SEQ ID NOs: 205-208, and HVR-L1 is SEQ ID NO: 3, HVR-L2 sequences are those sequences specifically enumerated for each clone in Table B, and HVR-L3 is SEQ ID NO: 4.

In one embodiment, an antibody of the invention comprises a heavy chain variable domain, wherein the framework sequence comprises at least one sequence of SEQ ID NOs: 217-220, and HVR H1, H2 and H3 sequences are SEQ ID NOs: 5, 60, and 6, respectively (clone Apu3.A8). Similarly, in other embodiments, antibodies of each of clones Apu3.A9-H10 comprise a heavy chain variable domain, wherein the framework sequence comprises at least one sequence of SEQ ID NOs: 217-220, and HVR-H1 is SEQ ID NO: 5, HVR-H2 sequences are those sequences specifically enumerated for each clone in Table B, and HVR-H3 is SEQ ID NO: 6. In one embodiment, an antibody of the invention comprises a light chain variable domain, wherein the framework sequence comprises at least one sequence of SEQ ID NOs: 213-216, and HVR L1, L2 and L3 sequences are SEQ ID NOs: 3, 8, and 4, respectively (Apu3.A8). Similarly, in other embodiments, antibodies of each of clones Apu3.A9-H10 shown in Table B comprise a light chain variable domain, wherein the framework sequence comprises at least one sequence of SEQ ID NOs: 213-216, and HVR-L1 is SEQ ID NO: 3, HVR-L2 sequences are those sequences specifically enumerated for each clone in Table B, and HVR-L3 is SEQ ID NO: 4.

In another example, an affinity matured antibody of the invention which specifically binds to K63-linked polyubiquitin with high affinity but binds to K48-linked polyubiquitin with substantially reduced affinity comprises substitution at HVR-H2 amino acid positions 50, 52, 53, 54 and 56. In another example, an affinity matured antibody of the invention which specifically binds to K63-linked polyubiquitin with high affinity but binds to K48-linked polyubiquitin with substantially reduced affinity comprises substitution at HVR-L2 amino acid positions 49, 50, 52, and 53.

In one embodiment, an antibody of the invention comprises a heavy chain variable domain comprising the sequence of SEQ ID NOs: 5, 8, and 6. In one embodiment, an antibody of the invention comprises a light chain variable domain comprising the sequence of SEQ ID NOs: 3, 60, and 4. In one embodiment, an antibody of the invention comprises a heavy chain variable domain comprising the sequence of SEQ ID NOs: 5, 8, and 6 and also comprises a light chain variable domain comprising the sequence of SEQ ID NOs: 3, 60, and 4. In another embodiment, an antibody of the invention comprises a heavy chain variable domain comprising the sequence of SEQ ID NOs: 5, 63, and 6. In one embodiment, an antibody of the invention comprises a light chain variable domain comprising the sequence of SEQ ID NOs: 3, 11, and 4. In one embodiment, an antibody of the invention comprises a heavy chain variable domain comprising the sequence of SEQ ID NOs: 5, 63, and 6 and also comprises a light chain variable domain comprising the sequence of SEQ ID NOs: 3, 11, and 4. In another embodiment, an antibody of the invention comprises a heavy chain variable domain comprising the sequence of SEQ ID NOs: 5, 66, and 6. In one embodiment, an antibody of the invention comprises a light chain variable domain comprising the sequence of SEQ ID NOs: 3, 14, and 4. In one embodiment, an antibody of the invention comprises a heavy chain variable domain comprising the sequence of SEQ ID NOs: 5, 66, and 6 and also comprises a light chain variable domain comprising the sequence of SEQ ID NOs: 3, 14, and 4.

In one aspect, the invention provides an antibody that competes with any of the above-mentioned antibodies for binding to polyubiquitin. In one aspect, the invention provides an antibody that binds to the same antigenic determinant on polyubiquitin as any of the above-mentioned antibodies.

As shown herein, the antibodies of the invention specifically bind to an isolated polyubiquitin having a specific lysine linkage. As shown herein, the antibodies of the invention also specifically bind to polyubiquitin having a K63 lysine linkage when that polyubiquitin is attached to a heterologous protein (see, e.g., Examples 2 and 3).

Compositions comprising at least one anti-polyubiquitin antibody or at least one polynucleotide comprising sequences encoding an anti-polyubiquitin antibody are provided. In certain embodiments, a composition may be a pharmaceutical composition. As used herein, compositions comprise one or more antibodies that bind to one or more polyubiquitin and/or one or more polynucleotides comprising sequences encoding one or more antibodies that bind to one or more polyubiquitin. These compositions may further comprise suitable carriers, such as pharmaceutically acceptable excipients including buffers, which are well known in the art.

Isolated antibodies and polynucleotides are also provided. In certain embodiments, the isolated antibodies and polynucleotides are substantially pure.

In one embodiment, anti-polyubiquitin antibodies are monoclonal. In another embodiment, fragments of the anti-polyubiquitin antibodies (e.g., Fab, Fab'-SH and F(ab')2 fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

Generation of Anti-Polyubiquitin Antibodies using a Phage Display Library

A variety of methods are known in the art for generating phage display libraries from which an antibody of interest can be obtained. One method of generating antibodies of interest is through the use of a phage antibody library as described in Lee et al., J. Mol. Biol. (2004), 340(5):1073-93.

The anti-polyubiquitin antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-polyubiquitin antibodies of the invention can be obtained by designing a suitable antigen screening procedure to select for the phage clone of interest followed by construction of a full length anti-polyubiquitin antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-polyubiquitin clones is desired, the subject is immunized with polyubiquitin to generate an antibody response, and spleen cells and/or circulating B cells or other peripheral blood lymphocytes (PBLs) are recovered for library construction. In one embodiment, a human antibody gene fragment library biased in favor of anti-human polyubiquitin clones is obtained by generating an anti-human polyubiquitin antibody response in transgenic mice carrying a functional human immunoglobulin gene array (and lacking a functional endogenous antibody production system) such that polyubiquitin immunization gives rise to B cells producing human antibodies against polyubiquitin. The generation of human antibody-producing transgenic mice is described in Section (III)(b) below.

Additional enrichment for anti-polyubiquitin reactive cell populations can be obtained by using a suitable screening procedure to isolate B cells expressing polyubiquitin-specific membrane bound antibody, e.g., by cell separation with polyubiquitin affinity chromatography or adsorption of cells to fluorochrome-labeled polyubiquitin followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which polyubiquitin is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). In certain embodiments, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

Screening of the libraries can be accomplished by any art-known technique. For example, polyubiquitin can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized polyubiquitin under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by polyubiquitin antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for polyubiquitin. However, random mutation of a selected antibody (e.g. as performed in some of the affinity maturation techniques described above) is likely to give rise to many mutants, most binding to antigen, and a few with higher affinity. With limiting polyubiquitin, rare high affinity phage could be competed out. To retain all the higher affinity mutants, phages can be incubated with excess biotinylated polyubiquitin, but with the biotinylated polyubiquitin at a concentration of lower molarity than the target molar affinity constant for polyubiquitin. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-polyubiquitin clones may be activity selected. In one embodiment, the invention provides anti-polyubiquitin antibodies that block the binding between a polyubiquitin ligand and polyubiquitin, but do not block the binding between a polyubiquitin ligand and a second protein. Fv clones corresponding to such anti-polyubiquitin antibodies can be selected by (1) isolating anti-polyubiquitin clones from a phage library as described in Section B(I)(2) above, and optionally amplifying the isolated population of phage clones by growing up the population in a suitable bacterial host; (2) selecting polyubiquitin and a second protein against which blocking and non-blocking activity, respectively, is desired; (3) adsorbing the anti-polyubiquitin phage clones to immobilized polyubiquitin; (4) using an excess of the second protein to elute any undesired clones that recognize polyubiquitin-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In one embodiment, a Fv clone derived from human variable DNA is fused to human constant region DNA to form coding sequence(s) for all human, full or partial length heavy and/or light chains.

The antibodies produced by naive libraries (either natural or synthetic) can be of moderate affinity ($K_a^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$ M range.

Other Methods of Generating Anti-Polyubiquitin Antibodies

Other methods of generating and assessing the affinity of antibodies are well known in the art and are described, e.g., in Kohler et al., Nature 256: 495 (1975); U.S. Pat. No. 4,816,567; Goding, Monoclonal Antibodies: Principles and Practice, pp. 59-103 (Academic Press, 1986; Kozbor, *J. Immunol.*, 133:3001 (1984); Brodeur et al., *Monoclonal Antibody Production Techniques and Applications*, pp. 51-63 (Marcel Dekker, Inc., New York, 1987; Munson et al., *Anal. Biochem.*, 107:220 (1980); Engels et al., *Agnew. Chem. Int. Ed. Engl.*, 28: 716-734 (1989); Abrahmsen et al., *EMBO J.*, 4: 3901 (1985); *Methods in Enzymology*, vol. 44 (1976); Morrison et al., *Proc. Natl. Acad. Sci. USA*, 81: 6851-6855 (1984).

General Methods

In general, the invention provides affinity-matured anti-K63-linked polyubiquitin antibodies. These antibodies have increased affinity and specificity for K63-linked polyubiquitin relative to the antibodies described in US Patent Publication No. US2007-0218069, incorporated by reference herein in its entirety. The best anti-K63-linked Fab identified in that publication (Apu2.16) has a Kd of approximately 100 nM and a small amount of artifactual binding to K48-linked polyubiquitin. The improved Fabs and antibodies provided herein are affinity-matured versions of Apu2.16, and the best binders (see, for example, the Fabs Apu3.A8, Apu3.A12, and Apu3.B3 and antibody versions thereof) have a greater than ten-fold increase in affinity over Apu2.16 for K63-linked polyubiquitin and negligible binding to K48-linked polyubiquitin. This increase in affinity and sensitivity permits the molecules of the invention to be used for applications and methods that are benefited by (a) the increased sensitivity of the molecules of the invention and/or (b) the tight binding of K63-linked polyubiquitin by the molecules of the invention and/or (c) the increased specificity of the molecules of the invention for K63-linked polyubiquitin relative to K48-linked polyubiquitin, relative to the parental molecule Apu2.16.

In one embodiment, the invention provides anti-K63-linked polyubiquitin antibodies that are useful for treatment of K63-linked polyubiquitin-mediated disorders in which a partial or total blockade of one or more K63-linked polyubiquitin activities is desired. In one embodiment, the anti-K63-linked polyubiquitin antibodies of the invention are used to treat cancer. In another embodiment, the anti-K63-linked polyubiquitin antibodies provided herein are used to treat muscular disorders, such as those indicated above. In another embodiment, the anti-K63-linked polyubiquitin antibodies provided herein are used to treat neurological disorders, such as those indicated above. In another embodiment, the anti-K63-linked polyubiquitin antibodies provided herein are used to treat genetic disease. In another embodiment, the anti-K63-linked polyubiquitin antibodies provided herein are used to treat immune/inflammatory disorders.

The unique properties of the anti-K63-linked polyubiquitin antibodies of the invention make them particularly useful for distinguishing between different lysine-linked forms of polyubiquitin in a cellular system without resorting to cumbersome and expensive genetic manipulation or biophysical methods such as mass spectrometry. The anti-K63-linked polyubiquitin antibodies of the invention can be used to characterize the function(s) and activities of K63-linked polyubiquitins both in vitro and in vivo. For example, as shown herein, both RIP and IRAK1 are modulated in function and activity by alternative tagging to with either K48-linked or K63-linked polyubiquitin due to TNFα or IL-1β stimulation, respectively. The anti-K63-linked polyubiquitin antibodies of the invention permit the sensitive and specific detection of the K63-ubiquitinated versions of, e.g., RIP and/or IRAK in straightforward and routine biomolecular assays such as immunoprecipitations, ELISAs, or immunomicroscopy without the need for mass spectrometry or genetic manipulation. In turn, this provides a significant advantage in both observing and elucidating the normal functioning of these pathways and in detecting when the pathways are functioning aberrantly.

The anti-K63-linked polyubiquitin antibodies of the invention can also be used to determine the role of specific lysine-linked polyubiquitins in the development and pathogenesis of disease. For example, as described above, the anti-K63-linked polyubiquitin antibodies of the invention can be used to determine whether RIP or IRAK1 are aberrantly K63-polyubiquitinated, which in turn provides information about the normal or aberrant functioning of TNFα or IL-1β signaling, which can be correlated with one or more disease states.

The anti-K63-linked polyubiquitin antibodies of the invention can further be used to treat diseases in which one or more K63-linked polyubiquitins are aberrantly regulated or aberrantly functioning without interfering with the normal activity of polyubiquitins for which the anti-polyubiquitin antibodies of the invention are not specific.

In another aspect, the anti-K63-linked polyubiquitin antibodies of the invention find utility as reagents for detection and isolation of K63-linked polyubiquitin, such as detection of K63-linked polyubiquitin in various cell types and tissues, including the determination of K63-linked polyubiquitin density and distribution in cell populations and within a given cell, and cell sorting based on the presence or amount of K63-linked polyubiquitin. The antibodies of the invention are able to specifically bind not only to isolated K63-linked polyubiquitin of various chain lengths, but also to proteins which have been polyubiquitinated with K63-linked polyubiquitin, and thus detection and binding to either free (i.e. unconjugated to a heterologous protein) or K63-linked polyubiquitinated protein (i.e., conjugated to a heterologous protein) and/or both is contemplated herein.

In yet another aspect, the present anti-K63-linked polyubiquitin antibodies are useful for the development of polyubiquitin antagonists with blocking activity patterns similar to those of the subject antibodies of the invention. For example, anti-K63-linked polyubiquitin antibodies of the invention can be used to determine and identify other antibodies that have the same K63-linked polyubiquitin binding characteristics and/or capabilities of blocking K63-linked polyubiquitin-mediated pathways.

As a further example, anti-K63-linked polyubiquitin antibodies of the invention can be used to identify other anti-polyubiquitin antibodies that bind substantially the same antigenic determinant(s) of K63-linked polyubiquitin as the antibodies exemplified herein, including linear and conformational epitopes.

The anti-polyubiquitin antibodies of the invention can be used in assays based on the physiological pathways in which K63-linked polyubiquitin is involved to screen for small molecule antagonists of K63-linked polyubiquitin which will exhibit similar pharmacological effects in blocking the binding of one or more binding partners to K63-linked polyubiquitin as the antibody does. For example, K63-linked polyubiquitin is known to be involved in DNA repair (see, e.g., Pickart and Fushman, Curr. Opin. Chem. Biol. 8: 610-616 (2004)), and thus the activity of anti-K63-linked polyubiquitin antibodies to antagonize a DNA repair pathway may be compared to the activity of one or more potential small molecule antagonists of K63-linked polyubiquitin in that same DNA repair pathway. Similarly, in another example, K63-linked polyubiquitin is known to be involved in formation of Lewy bodies in Parkinson's disease (see, e.g., Lim et al., J. Neurosci. 25(8): 2002-9 (2005)), and thus the activity of anti-K63-linked polyubiquitin antibodies to antagonize the formation of Lewy bodies may be compared to the activity of one or more potential small molecule antagonists of K63-linked polyubiquitin in antagonizing the formation of Lewy bodies.

Generation of antibodies can be achieved using routine skills in the art, including those described herein, such as the hybridoma technique and screening of phage displayed libraries of binder molecules. These methods are well-established in the art.

Briefly, the anti-polyubiquitin antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-polyubiquitin antibodies of the invention can be obtained by designing a suitable antigen screening procedure to select for the phage clone of interest followed by construction of a full length anti-polyubiquitin antibody clone using the Fv sequences from the phage clone of interest and suitable constant region (Fc) sequences described in Kabat et al., *Sequences of Proteins of Immunological Interest,* Fifth Edition, NIH Publication 91-3242, Bethesda MD (1991), vols. 1-3. See also PCT Pub. WO03/102157, and references cited therein.

In one embodiment, anti-polyubiquitin antibodies of the invention are monoclonal. Also encompassed within the scope of the invention are antibody fragments such as Fab, Fab', Fab'-SH and F(ab')2 fragments, and variations thereof, of the anti-polyubiquitin antibodies provided herein. These antibody fragments can be created by traditional means, such as enzymatic digestion, or may be generated by recombinant techniques. Such antibody fragments may be chimeric, human or humanized. These fragments are useful for the experimental, diagnostic, and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-polyubiquitin monoclonal antibodies of the invention can be made using a variety of methods known in the art, including the hybridoma method first described by Kohler et al., *Nature,* 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells include, but are not limited to, cells of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5, 840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$, 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, growth occurs at a temperature range including, but not limited to, about 20° C. to about 39° C., about 25° C. to about 37° C., and at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, for example about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem.102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. Nos. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-polyubiquitin antibodies of the invention can be constructed by combining Fv clone variable domain sequence(s) selected from human-derived phage display libraries with known human constant domain sequences(s) as described above. Alternatively, human monoclonal anti-polyubiquitin antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published April 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for polyubiquitin including a specific lysine linkage and the other is for any other antigen. In certain embodiments, bispecific antibodies may bind to two different polyubiquitins having two different lysine linkages. Bispecific antibodies can be prepared as full length antibodies or antibody fragments (e.g. F(ab')2 bispecific antibodies). Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different embodiment, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tuft et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The dimerization domain comprises (or consists of), for example, an Fc region or a hinge region. In this scenario, the antibody will comprise an Fc region and three or more antigen binding sites amino-terminal to the Fc region. In one embodiment, a multivalent antibody comprises (or consists of), for example, three to about eight, or four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH- CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. Antibody Variants In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is tested for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is tested for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{311}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolostatins, aurostatins, a trichothecene, and CC1065, and the derivatives of these toxins that have toxin activity, are also contemplated herein.

Maytansine and Maytansinoids

In some embodiments, the immunoconjugate comprises an antibody of the invention conjugated to one or more maytansinoid molecules.

Maytansinoids are mitotic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieties include: DM1; DM3; and DM4. Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Maytansinoids include, but are not limited to, maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Coupling agents include, but are not limited to, N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Exemplary auristatin embodiments include MMAE and MMAF. Additional exemplary embodiments comprising MMAE or MMAF and various linker components (described further herein) include Ab-MC-vc-PAB-MMAF, Ab-MC-vc-PAB-MMAE, Ab-MC-MMAE and Ab-MC-MMAF.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lüke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody of the invention conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug to which the antibody can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos.5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Exemplary linker component structures are shown below (wherein the wavy line indicates sites of covalent attachment to other components of the ADC):

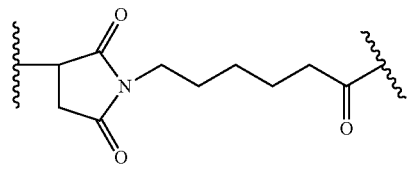

MC

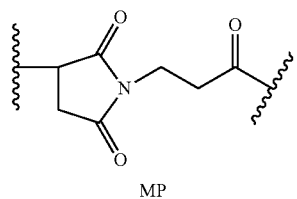

MP

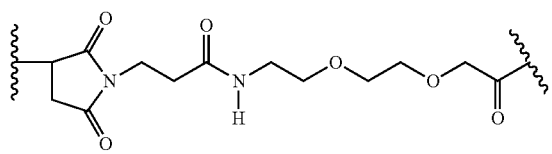

MPEG

Additional exemplary linker components and abbreviations include (wherein the antibody (Ab) and linker are depicted, and p is 1 to about 8):

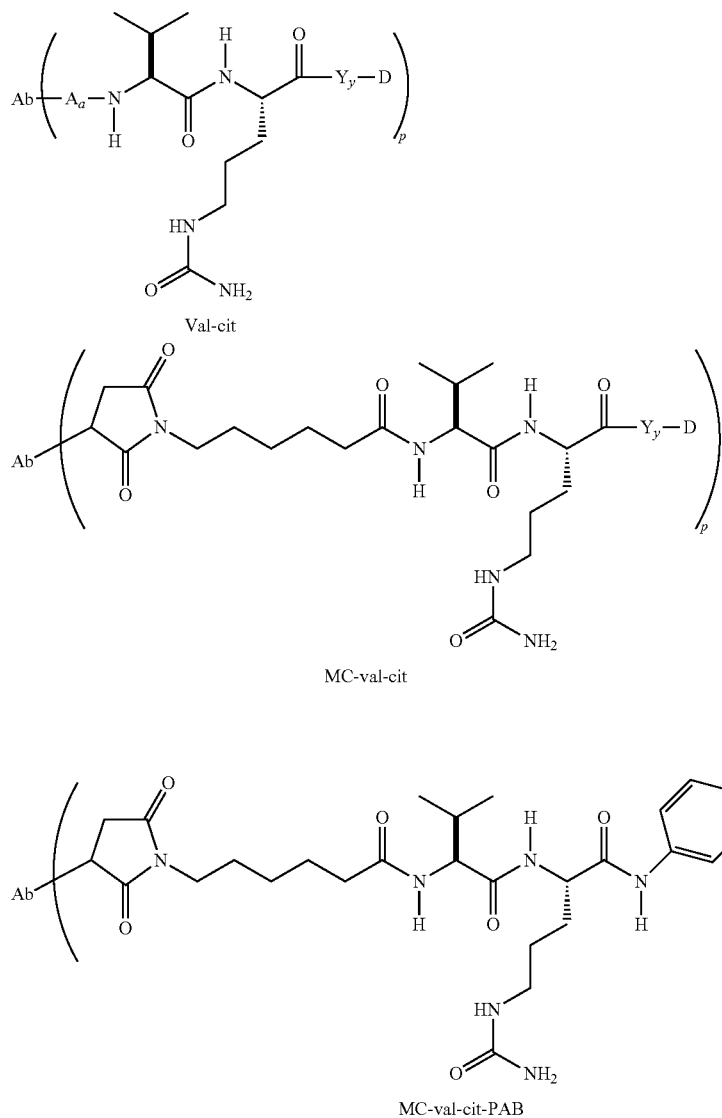

Val-cit

MC-val-cit

MC-val-cit-PAB

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. 5362852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent to one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody (Ab)-MC-MMAE may be prepared by conjugation of any of the antibodies provided herein with MC-MMAE as follows. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker reagent, maleimidocaproyl-monomethyl auristatin E (MMAE), i.e. MC-MMAE, dissolved in DMSO, is diluted in acetonitrile and water at known concentration, and added to the chilled reduced antibody 2H9 in PBS. After about one hour, an excess of maleimide is added to quench the reaction and cap any unreacted antibody thiol groups. The reaction mixture is concentrated by centrifugal ultrafiltration and 2H9-MC-MMAE is purified and desalted by elution through G25 resin in PBS, filtered through 0.2 μm filters under sterile conditions, and frozen for storage.

Antibody-MC-MMAF may be prepared by conjugation of any of the antibodies provided herein with MC-MMAF following the protocol provided for preparation of Ab-MC-MMAE.

Antibody-MC-val-cit-PAB-MMAE is prepared by conjugation of any of the antibodies provided herein with MC-val-cit-PAB-MMAE following the protocol provided for preparation of Ab-MC-MMAE.

Antibody-MC-val-cit-PAB-MMAF is prepared by conjugation of any of the antibodies provided herein with MC-val-cit-PAB-MMAF following the protocol provided for preparation of Ab-MC-MMAE.

Antibody-SMCC-DM1 is prepared by conjugation of any of the antibodies provided herein with SMCC-DM1 as follows. Purified antibody is derivatized with (Succinimidyl 4-(N-maleimidomethyl) cyclohexane-1-carboxylate (SMCC, Pierce Biotechnology, Inc) to introduce the SMCC linker. Specifically, antibody is treated at 20 mg/mL in 50 mM potassium phosphate/50 mM sodium chloride/2 mM EDTA, pH 6.5 with 7.5 molar equivalents of SMCC (20 mM in DMSO, 6.7 mg/mL). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody-containing fractions are pooled and assayed.

Antibody-SMCC prepared thusly is diluted with 50 mM potassium phosphate/50 mM sodium chloride/2 mM EDTA, pH 6.5, to a final concentration of about 10 mg/ml, and reacted with a 10 mM solution of DM1 in dimethylacetamide. The reaction is stirred at ambient temperature under argon for 16.5 hours. The conjugation reaction mixture is filtered through a Sephadex G25 gel filtration column (1.5× 4.9 cm) with 1×PBS at pH 6.5. The DM1 drug to antibody ratio (p) may be about 2 to 5, as measured by the absorbance at 252 nm and at 280 nm.

Ab-SPP-DM1 is prepared by conjugation of any of the antibodies provided herein with SPP-DM1 as follows. Purified antibody is derivatized with N-succinimidyl-4-(2-pyridylthio)pentanoate to introduce dithiopyridyl groups. Antibody (376.0 mg, 8 mg/mL) in 44.7 mL of 50 mM potassium phosphate buffer (pH 6.5) containing NaCl (50 mM) and EDTA (1 mM) is treated with SPP (5.3 molar equivalents in 2.3 mL ethanol). After incubation for 90 minutes under argon at ambient temperature, the reaction mixture is gel filtered through a Sephadex G25 column equilibrated with a 35 mM sodium citrate, 154 mM NaCl, 2 mM EDTA buffer. Antibody-containing fractions were pooled and assayed. The degree of modification of the antibody is determined as described above.

Antibody-SPP-Py (about 10 μmoles of releasable 2-thiopyridine groups) is diluted with the above 35 mM sodium citrate buffer, pH 6.5, to a final concentration of about 2.5 mg/mL. DM1 (1.7 equivalents, 17 μmoles) in 3.0 mM dimethylacetamide (DMA, 3% v/v in the final reaction mixture) is then added to the antibody solution. The reaction proceeds at ambient temperature under argon for about 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate may be about 5.0 mL/min and 65 fractions (20.0 mL each) are collected. The number of DM1 drug molecules linked per antibody molecule (p') is determined by measuring the absorbance at 252 nm and 280 nm, and may be about 2 to 4 DM1 drug moieties per 2H9 antibody.

Antibody-BMPEO-DM1 is prepared by conjugation of any of the antibodies provided herein with BMPEO-DM1 as follows. The antibody is modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing antibody in phosphate buffered saline at a concentration of approximately 1.6 mg/ml (10 micromolar) and allowing it to react for 1 hour to form an antibody-linker intermediate, 2H9-BMPEO. Excess BM(PEO)4 is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the 2H9-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on 5200 columns in PBS is used to remove high molecular weight aggregates and to furnish purified 2H9-BMPEO-DM1.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Pharmaceutical Formulations

Therapeutic formulations comprising an antibody of the invention are prepared for storage by mixing the antibody having the desired degree of purity with optional physiologically acceptable carriers, excipients or stabilizers (Remington's Pharmaceutical *Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of polyubiquitins and polyubiquitinated proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for a polyubiquitin having a K63 lysine linkage, and inhibits normal K63-linked polyubiquitin activity by blocking or interfering with the interaction between a K63-linked polyubiquitin and a protein that interacts with that K63-linked polyubiquitin, thereby inhibiting the corresponding signal pathway and other associated molecular or cellular events. In another aspect, a blocking antibody of the invention specific for K63-linked polyubiquitin interacts with one or more proteins conjugated with K63-linked polyubiquitin, thereby inhibiting the interaction of the protein with signal pathways or other binding partners and interfering with associated molecular or cellular events.

In certain embodiments, an immunoconjugate comprising an antibody of the invention conjugated with a cytotoxic agent is administered to the patient. In some embodiments, the immunoconjugate and/or antigen to which it is bound is/are internalized by cells expressing one or more proteins on their cell surface which are associated with K63-linked polyubiquitin, resulting in increased therapeutic efficacy of the immunoconjugate in killing the target cell with which it is associated. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-polyubiquitin antibody of the invention can be delivered to a target cell, such that one or more intrabodies are expressed which are capable of intracellular binding to a polyubiquitin and modulation of one or more polyubiquitin-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA (1999), 96:4325-4329.

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

The antibody composition of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Example 1

Affinity Maturation of a K63-Linked Diubiquitin-Specific Antibody Fragment

Panels of antibodies able to discriminate between K48-linked polyubiquitin and K63-linked polyubiquitin were described in US Patent Publication No. US2007-0218069, incorporated by reference herein in its entirety. The affinity and specificity of the best anti-K63-linked Fab identified in that publication (Apu2.16, Kd of approximately 100 nM and a small amount of artifactual binding to K48-linked polyubiquitin) was inferior to the affinity and specificity of the best anti-K48-linked Fab identified in that publication (Apu2.07, Kd of approximately 1 nM, no observed binding to K63-linked polyubiquitin). An improved K63-linked polyubiquitin-specific Fab/antibody was sought to facilitate applications in which greater specificity or affinity of the Fab/antibody would be desirable.

(A) Library Generation

The Apu2.16 anti-K63-linked diubiquitin antibody fragment (Fab) was subjected to mutagenesis in order to affinity mature the antibody. Residues 49, 50, 52, and 53 of CDR L2 and residues 50, 52, 53, 54, and 56 of CDR H2 were selected for mutagenesis based on their contact with K63-linked diubiquitin, as shown in the co-crystal structure of Apu2.16 and K63-linked diubiquitin (see FIG. 2 and US Patent Publication No. US2007-0218069, incorporated herein in its entirety). An Apu2.16 stop template with TAA stop codons at positions 51 of CDR L2 and 52a of CDR H2 was used to force mutagenesis of both CDR regions. Expression of this construct was under the control of the bacterial alkaline phosphatase (PhoA) promoter. Both the light chain and the heavy chain contained an amino terminal bacterial stII signal sequence to permit secretion in E. coli. The heavy chain carboxyl terminus was fused in-frame to an amber stop codon followed by gene product III of the M13 bacteriophage, allowing for monovalent Fab display on phage when expressed in an amber suppressor E. coli strain. Degenerate oligonucleotides were synthesized to soft-randomize the positions of contact so that 50% of the time the Apu2.16 wild-type residue would be retained and 50% of the time one of the remaining 19 amino acids would be encoded. To achieve soft randomization, oligonucleotides were designed such that certain nucleotide positions were occupied 70% of the time with the indicated base and 10% of the time occupied by one of the three other bases (Gallop et al., J. Med. Chem. 37: 1233 (1994)). Where such soft randomization was included at a particular base, the presence of the soft randomization is indicated by the presence of a number at that base position. The number "5" indicates that the base adenine was present 70% of the time at that position, while the bases guanine, cytosine, and thymine were each present 10% of the time. Similarly, the number "6" refers to guanine, "7" to cytosine, and "8" to thymine, where in each case, each of the other three bases was present only 10% of the time.

Mutagenic oligonucleotides 310887 (CCGAAGCT TCTGATT857876GCA877567CTCTACTCTGGAGTC) (SEQ ID NO: 1) and 310890 (GGCCTGGA ATGGGTTGCA858ATT878CCT858858GGC878ACTT CTTATGCCGATAGC) (SEQ ID NO: 2) were used with 40 μg of Kunkel DNA of the Apu2.16 stop template in a Kunkel mutagenesis reaction (see Kunkel, Proc. Natl. Acad. Sci. USA 82: 488 (1985) and Sidhu et al., Meth. Enzymol. 328: 333 (2000)). The mutagenesis reaction was electroporated into ElectroTen Blue E. coli (Stratagene) and recovered in 25 mL of SOC medium for 45 minutes at 37° C. with shaking. Twenty microliters were removed and ten-fold serial dilutions were plated onto solid agar plates containing carbenicillin and grown overnight at 37° C. to determine the library size. The remaining culture was transferred to 500 mL of 2YT broth containing 50 μg/mL carbenicillin, 50 μg/mL kanamycin, and $10^{10}$ phage/mL M13K07 helper phage (New England Biolabs). The culture was grown for 14 hours at 30° C. with shaking. The library contained approximately $3 \times 10^{10}$ CFUs. The phage were purified from the culture supernatant by two rounds of precipitation with 1/5 volume of 20% polyethylene glycol (PEG)/2.5 M NaCl.

(B) Library Sorting

Amplified phage were used in sorting against enzymatically synthesized K63-linked diubiquitin (Boston Biochem) immobilized on 96-well Maxisorb immunoplates (Nunc). The plates were coated overnight at 4° C. with 5 μg/mL K63-linked diubiquitin in 50 mM sodium carbonate buffer, pH 9.6. The coated plates were blocked with 2.5% milk in PBS containing 0.05% Tween-20 (PBST) for one hour at 25° C. with shaking. The phage were diluted to an $OD_{268}$ of 5.0 in 2.5% milk/PBST and incubated on ice for one hour. After blocking, the plate was washed five times with PBST. One hundred microliters/well of the phage was added and incubated at 25° C. for one hour with shaking. After binding, the plate was washed ten times with PBST. Phage were eluted with 100 μL/well of 100 mM HCl for 20 minutes at 25° C. with shaking. The eluate was neutralized with 1/10 volume 1 M Tris, pH 11.0 and subsequently propagated in XL-1 blue E. coli (Stratagene) with the addition of M13K07 helper phage.

Amplified phage were used in subsequent rounds of sorting. The second sort was performed as described above, with the exception that 100 nM biotinylated K63-linked diubiquitin was used as a target in solution and the phage were used at an $OD_{268}$ of 1.0. The biotinylated K63-linked diubiquitin along with bound phage were captured on 5 μg/mL neutravidin-coated immunoplates. The third sorting round was performed similarly to the second round, with the addition of soluble 100 nM K48-linked diubiquitin and 100 nM monoubiquitin (Boston Biochem) as competitors in the phage blocking and phage binding steps. In the fourth sorting round the biotinylated K63-linked diubiquitin target concentration was decreased to 10 nM and the K48-linked diubiquitin and monoubiquitin competitor concentrations were increased to 1 μM each. Enrichment for binding to biotinylated K63-linked diubiquitin compared to neutravidin alone was observed after rounds three and four.

Ninety-six individual clones from the fourth sort were grown up in a 96-well format in 1 mL of 2YT broth containing 50 μg/mL carbenicillin and $10^{10}$ phage/mL M13K07 helper phage. Supernatants from those cultures were used in high-throughput phage ELISAs for binding to K63-linked diubiquitin, K48-linked diubiquitin, monoubiquitin, or the uncoated wells of the plate. Fifty-one clones demonstrated specific binding to K63-linked diubiquitin and their DNA was sequenced using standard procedures. The sequences of CDRs L2 and H2 for each clone are shown in Table B. CDRs L1, L3, H1, and H3 were not sequenced, but since they were not targeted for mutagenesis they were expected to retain the Apu2.16 template CDR L1 sequence (RASQSVSSAVA) (SEQ ID NO: 3), CDR L3 sequence (QQYSSYSSLFT) (SEQ ID NO: 4), CDR H1 sequence (VKTGLI) (SEQ ID NO: 5), and CDR H3 sequence (EYYRWYTAI) (SEQ ID NO: 6), which had not been targeted for mutagenesis.

TABLE B

HVR L2 and HVR H2 Sequences for Parental and Affinity-Matured Anti-K63-linked Polyubiquitin Fabs

| Clone | HVR L2 sequence | | | | | | | | SEQ ID NO | HVR H2 sequence | | | | | | | | | | | | | | | | | SEQ ID NO |
|---|---|---|---|---|---|---|---|---|---|---|---|---|---|---|---|---|---|---|---|---|---|---|---|---|---|---|---|
| | 49 | 50 | 51 | 52 | 53 | 54 | 55 | 56 | | 50 | 51 | 52 | 52a | 53 | 54 | 55 | 56 | 57 | 58 | 59 | 60 | 61 | 62 | 63 | 64 | 65 | |
| Apu2.16 | Y | S | A | S | S | L | Y | S | 7 | Y | I | S | P | Y | Y | G | S | T | S | Y | A | D | S | V | K | G | 59 |
| A8 | Y | S | A | R | S | L | Y | S | 8 | Y | I | T | P | Y | Y | G | S | T | S | Y | A | D | S | V | K | G | 60 |
| A9 | Y | S | A | V | S | L | Y | S | 9 | Y | I | S | P | Y | Y | G | S | T | S | Y | A | D | S | V | K | G | 61 |
| A11 | Y | S | A | S | S | L | Y | S | 10 | D | I | T | P | Y | Y | G | S | T | S | Y | A | D | S | V | K | G | 62 |
| A12 | Y | S | A | R | S | L | Y | S | 11 | Y | I | A | P | Y | Y | G | S | T | S | Y | A | D | S | V | K | G | 63 |
| B1 | Y | S | A | R | S | L | Y | S | 12 | Y | I | T | P | Y | Y | G | S | T | S | Y | A | D | S | V | K | G | 64 |
| B2 | Y | S | A | A | S | L | Y | S | 13 | Y | I | F | P | Y | Y | G | S | T | S | Y | A | D | S | V | K | G | 65 |
| B3 | Y | A | A | V | S | L | Y | S | 14 | Y | I | A | P | Y | H | G | A | T | S | Y | A | D | S | V | K | G | 66 |
| B4 | Y | S | A | R | S | L | Y | S | 15 | Y | I | F | P | Y | Y | G | S | T | S | Y | A | D | S | V | K | G | 67 |
| B5 | Y | S | A | R | S | L | Y | S | 16 | D | I | A | P | Y | F | G | S | T | S | Y | A | D | S | V | K | G | 68 |
| B9 | Y | S | A | A | S | L | Y | S | 17 | Y | I | F | P | Y | Y | G | S | T | S | Y | A | D | S | V | K | G | 69 |
| C1 | Y | A | A | V | S | L | Y | S | 18 | Y | I | A | P | Y | Y | G | S | T | S | Y | A | D | S | V | K | G | 70 |
| C3 | Y | S | A | A | S | L | Y | S | 19 | D | I | V | P | Y | Y | G | S | T | S | Y | A | D | S | V | K | G | 71 |
| C4 | Y | S | A | V | S | L | Y | S | 20 | Y | I | S | P | Y | Y | G | S | T | S | Y | A | D | S | V | K | G | 72 |
| C5 | Y | S | A | R | S | L | Y | S | 21 | Y | I | T | P | Y | Y | G | S | T | S | Y | A | D | S | V | K | G | 73 |
| C8 | Y | A | A | A | S | L | Y | S | 22 | Y | I | T | P | Y | Y | G | S | T | S | Y | A | D | S | V | K | G | 74 |
| C12 | Y | S | A | V | S | L | Y | S | 23 | D | I | S | P | Y | Y | G | S | T | S | Y | A | D | S | V | K | G | 75 |
| D1 | Y | S | A | T | S | L | Y | S | 24 | Y | I | A | P | Y | Y | G | W | T | S | Y | A | D | S | V | K | G | 76 |
| D3 | Y | S | A | N | S | L | Y | S | 25 | D | I | V | P | Y | Y | G | S | T | S | Y | A | D | S | V | K | G | 77 |
| D7 | Y | S | A | V | S | L | Y | S | 26 | Y | I | F | P | Y | Y | G | S | S | S | Y | A | D | S | V | K | G | 78 |
| D8 | Y | S | A | A | S | L | Y | S | 27 | Y | I | V | P | Y | Y | G | S | T | S | Y | A | D | S | V | K | G | 79 |
| D9 | Y | A | A | V | S | L | Y | S | 28 | D | I | F | P | Y | Y | G | S | T | S | Y | A | D | S | V | K | G | 80 |
| D10 | Y | S | A | V | S | L | Y | S | 29 | Y | I | S | P | Y | Y | G | S | T | S | Y | A | D | S | V | K | G | 81 |
| D11 | Y | S | A | R | S | L | Y | S | 30 | Y | I | A | P | Y | Y | G | S | T | S | Y | A | D | S | V | K | G | 82 |
| E1 | Y | S | A | A | S | L | Y | S | 31 | W | I | T | P | Y | Y | G | S | T | S | Y | A | D | S | V | K | G | 83 |
| E2 | F | S | A | V | S | L | Y | S | 32 | Y | I | S | P | Y | Y | G | F | T | S | Y | A | D | S | V | K | G | 84 |
| E3 | Y | S | A | R | S | L | Y | S | 33 | Y | I | R | P | Y | Y | G | S | T | S | Y | A | D | S | V | K | G | 85 |
| E4 | Y | S | A | R | S | L | Y | S | 34 | D | I | A | P | Y | Y | G | F | T | S | Y | A | D | S | V | K | G | 86 |
| E5 | Y | A | A | A | S | L | Y | S | 35 | Y | I | S | P | Y | Y | G | G | T | S | Y | A | D | S | V | K | G | 87 |
| E8 | Y | S | A | A | S | L | Y | S | 36 | Y | I | A | P | Y | Y | G | W | T | S | Y | A | D | S | V | K | G | 88 |
| E12 | Y | S | A | R | S | L | Y | S | 37 | Y | I | T | P | Y | Y | G | F | T | S | Y | A | D | S | V | K | G | 89 |
| F1 | Y | S | A | V | S | L | Y | S | 38 | Y | I | V | P | Y | Y | G | S | T | S | Y | A | D | S | V | K | G | 90 |
| F3 | Y | S | A | L | S | L | Y | S | 39 | D | I | F | P | Y | Y | G | S | T | S | Y | A | D | S | V | K | G | 91 |
| F4 | Y | S | A | A | S | L | Y | S | 40 | Y | I | T | P | Y | L | G | S | T | S | Y | A | D | S | V | K | G | 92 |
| F6 | Y | S | A | S | S | L | Y | S | 41 | Y | I | S | P | Y | Y | G | S | T | S | Y | A | D | S | V | K | G | 93 |
| F9 | Y | S | A | S | S | L | Y | S | 42 | D | I | A | P | Y | Y | G | S | T | S | Y | A | D | S | V | K | G | 94 |
| G1 | Y | S | A | A | S | L | Y | S | 43 | Y | I | T | P | Y | Y | G | S | T | S | Y | A | D | S | V | K | G | 95 |
| G2 | Y | S | A | R | S | L | Y | S | 44 | Y | I | A | P | Y | Y | G | S | T | S | Y | A | D | S | V | K | G | 96 |
| G3 | Y | S | A | T | S | L | Y | S | 45 | D | I | S | P | Y | Y | G | S | T | S | Y | A | D | S | V | K | G | 97 |
| G4 | Y | A | A | L | S | L | Y | S | 46 | Y | I | T | P | Y | Y | G | S | T | S | Y | A | D | S | V | K | G | 98 |
| G5 | Y | S | A | A | S | L | Y | S | 47 | Y | I | A | P | Y | Y | G | S | T | S | Y | A | D | S | V | K | G | 99 |
| G10 | Y | S | A | V | S | L | Y | S | 48 | Y | I | T | P | Y | Y | G | S | T | S | Y | A | D | S | V | K | G | 100 |
| G11 | Y | A | A | A | S | L | Y | S | 49 | D | I | T | P | Y | Y | G | S | T | S | Y | A | D | S | V | K | G | 101 |
| G12 | Y | S | A | A | S | L | Y | S | 50 | Y | I | T | P | Y | Y | G | S | T | S | Y | A | D | S | V | K | G | 102 |
| H2 | Y | S | A | A | S | L | Y | S | 51 | D | I | T | P | Y | Y | G | S | T | S | Y | A | D | S | V | K | G | 103 |

TABLE B-continued

HVR L2 and HVR H2 Sequences for Parental and Affinity-Matured Anti-K63-linked Polyubiquitin Fabs

| Clone | HVR L2 sequence | | | | | | | | | SEQ ID NO | HVR H2 sequence | | | | | | | | | | | | | | SEQ ID NO |
| | 49 | 50 | 51 | 52 | 53 | 54 | 55 | 56 | | | 50 | 51 | 52 | 52a | 53 | 54 | 55 | 56 | 57 | 58 | 59 | 60 | 61 | 62 | 63 | 64 | 65 | |
|---|---|---|---|---|---|---|---|---|---|---|---|---|---|---|---|---|---|---|---|---|---|---|---|---|---|---|---|---|
| H3 | Y | A | A | A | S | L | Y | S | | 52 | Y | I | T | P | Y | Y | G | S | T | S | Y | A | D | S | V | K | G | 104 |
| H4 | Y | S | A | A | S | L | Y | S | | 53 | Y | I | S | P | Y | Y | G | S | T | S | Y | A | D | S | V | K | G | 105 |
| H5 | Y | A | A | A | S | L | Y | S | | 54 | D | I | S | P | Y | Y | G | F | T | S | Y | A | D | S | V | K | G | 106 |
| H6 | Y | S | A | S | S | L | Y | S | | 55 | Y | I | T | P | Y | Y | G | S | T | S | Y | A | D | S | V | K | G | 107 |
| H7 | Y | S | A | V | S | L | Y | S | | 56 | Y | I | T | P | Y | Y | G | F | T | S | Y | A | D | S | V | K | G | 108 |
| H9 | Y | S | A | V | S | L | Y | S | | 57 | D | I | T | P | Y | Y | G | S | T | S | Y | A | D | S | V | K | G | 109 |
| H10 | Y | S | A | L | S | L | Y | S | | 58 | Y | I | A | P | Y | Y | G | S | T | S | Y | A | D | S | V | K | G | 110 |
| Consensus | Y/F | A/S | A | S/R/ V/T/A/N/L | S | L | Y | S | | 111 | Y/D/W | I | S/T/ A/F/Y/V | P | Y | Y/F/L/H | G | S/G/A/F/W | T | S | Y | A | D | S | V | K | G | 112 |

(C) Fab Production

Twenty-four of the most specific anti-K63-linked diubiquitin clones (as judged by a signal ratio of greater than ten for binding to K63-linked diubiquitin relative to K48-linked diubiquitin in the phage spot ELISA described above) were selected for soluble Fab production. Plasmids encoding these Fabs were transformed into E. coli and plated on solid agar containing carbenicillin. Single colonies were used to inoculate 25 mL of 2YT broth containing 50 μg/mL carbenicillin. Cultures were grown overnight at 37° C. and 5 mL were used to inoculate 500 mL of complete C.R.A.P. media (3.57 g $(NH_4)_2SO_4$, 0.71 g sodium citrate $2H_2O$, 1.07 g KCl, 5.36 g yeast extract, 5.36 g Hycase SF (Sheffield), pH adjusted to 7.3 by addition of KOH and volume adjusted to 872 mL with ultrapure water, autoclaved, cooled to 55° C., to which was added (per L) 110 mL 1 M MOPS pH 7.3, 11 mL 50% glucose, and 7 mL 1 M $MgSO_4$) with 50 μg/mL carbenicillin. Cultures were grown at 30° C. for 24 hours with shaking. Cells were harvested by centrifugation and pellets were stored at −20° C. Fabs were purified by resuspending each pellet in 35 mL cold wash buffer (PBS+150 mM NaCl) containing 10 μg/mL DNase I, 0.2 mg/mL lysozyme, and 1 mM phenylmethylsulphonylfluoride (PMSF). Pellets were resuspended by vortexing rapidly for 45 minutes at 25° C. Cell debris was pelleted by centrifugation and lysates were loaded on 1 mL protein A-sepharose columns (GE Health Sciences) preequilibrated with cold wash buffer. The columns were washed with 50 mL cold wash buffer, eluted with 3 mL 0.1 M acetic acid, and neutralized with 150 μL of 2M Tris, pH 11.0. The Fabs were concentrated using Amicon Ultra-15 centrifugal filter units (5 KD cut-off, Millipore). The resulting Fab concentrations were determined spectrophotometrically, and the concentrated Fabs were stored at 4° C.

(D) Affinity Analysis of Isolated Fabs

The affinities of the 24 selected Fabs (see Example 1(C), above), were determined by surface plasmon resonance (SPR) using a BIACORE™ A100 system (Biacore). Approximately 50 resonance units of K63-linked diubiquitin or K48-linked diubiquitin were immobilized in two of the four flow cells of a CM5 chip using the amine coupling protocol supplied by the manufacturer. One flow cell on each CM5 chip was activated and ethanolamine blocked without immobilizing protein, to be used as a reference. Two-fold serial dilutions (31.25-500 nM) of each Fab were injected (60 μL total at a flow rate of 30 μL/min) over each flow cell. The reference signal was subtracted from each flow cell signal. Following a dissociation period (10 minutes), the chip surface was regenerated with 15 μL of 10 mM HCl. Kinetic constants and binding constants were simultaneously calculated by nonlinear regression analysis, using software provided by the manufacturer, and are shown in Table C. The average (Avg) from three separate measurements of the kinetic constants and binding constants of the parental Apu2.16 Fab, and from single measurements for the 24 affinity matured Fabs are shown. Neither the parental Apu2.16 Fab, nor any of the 24 affinity matured Fabs demonstrated detectable binding to K48-linked diubiquitin.

TABLE C

Binding Constants for Affinity Matured Anti-K63-linked Polyubiquitin Fabs Binding to K63-linked Diubiquitin as Measured by SPR

| clone | kon (1/Ms) | koff (1/s) | Kd (nM) |
|---|---|---|---|
| Apu2.16 Avg | $4.9 \times 10^5$ | $5.4 \times 10^{-2}$ | 110 |
| Standard deviation for Apu2.16 measurements | $0.49 \times 10^5$ | $2.0 \times 10^{-2}$ | 30 |
| Apu3.A8 | $1.7 \times 10^6$ | $1.4 \times 10^{-2}$ | 8.7 |
| Apu3.A9 | $2.3 \times 10^6$ | $9.9 \times 10^{-2}$ | 44 |
| Apu3.A12 | $9.9 \times 10^9$ | $6.2 \times 10^1$ | 6.2 |
| Apu3.B3 | $4.8 \times 10^6$ | $2.9 \times 10^{-2}$ | 6.1 |
| Apu3.B5 | $1.0 \times 10^6$ | $4.6 \times 10^{-2}$ | 46 |
| Apu3.C1 | $4.3 \times 10^6$ | $7.8 \times 10^{-2}$ | 18 |
| Apu3.C4 | $4.7 \times 10^8$ | $3.4 \times 10^1$ | 73 |
| Apu3.C5 | $1.0 \times 10^6$ | $2.9 \times 10^{-2}$ | 28 |
| Apu3.D3 | $7.9 \times 10^5$ | $6.1 \times 10^{-2}$ | 78 |
| Apu3.D7 | $8.1 \times 10^5$ | $3.7 \times 10^{-2}$ | 46 |
| Apu3.D8 | $3.9 \times 10^8$ | $4.4 \times 10^0$ | 11 |
| Apu3.E1 | $1.1 \times 10^6$ | $2.1 \times 10^{-2}$ | 18 |
| Apu3.E2 | $1.0 \times 10^6$ | $3.0 \times 10^{-2}$ | 29 |
| Apu3.E4 | $7.2 \times 10^5$ | $8.2 \times 10^{-2}$ | 110 |
| Apu3.E5 | $1.0 \times 10^6$ | $2.6 \times 10^{-2}$ | 25 |
| Apu3.F1 | $8.3 \times 10^5$ | $2.3 \times 10^{-2}$ | 28 |
| Apu3.G1 | $6.5 \times 10^5$ | $5.4 \times 10^{-2}$ | 84 |
| Apu3.G2 | $6.1 \times 10^5$ | $5.4 \times 10^{-2}$ | 90 |
| Apu3.G3 | $1.0 \times 10^6$ | $4.1 \times 10^{-2}$ | 39 |
| Apu3.G4 | $7.3 \times 10^5$ | $2.4 \times 10^{-2}$ | 33 |
| Apu3.G5 | $1.1 \times 10^6$ | $3.1 \times 10^{-2}$ | 29 |
| Apu3.H5 | $1.0 \times 10^6$ | $2.9 \times 10^{-2}$ | 28 |
| Apu3.H6 | $3.6 \times 10^9$ | $7.8 \times 10^1$ | 22 |
| Apu3.H7 | $2.0 \times 10^4$ | $9.2 \times 10^{-4}$ | 45 |

(E) Western Blots of Affinity Matured Fabs

The binding constants obtained from the SPR analysis in Example 1(D) indicated that three clones (Apu3.A8, Apu3.A12, and Apu3.B3) displayed single digit nanomolar binding. These three Fabs along with the parental Apu2.16 Fab were tested for detection of K63-linked diubiquitin and K48-linked diubiquitin in a western blot. Six concentrations of K63-linked diubiquitin (31-1000 ng) and three concentrations of K48-linked diubiquitin (250-1000 ng) were run on a 4-12% NuPAGE gel (Invitrogen), transferred to a polyvinylidene fluoride (PVDF) membrane, and blotted with the parental clone and the three affinity-matured Fabs. The Fabs contained a carboxy-terminal 6×-His tag and were thus detected with an anti-pentaHis-HRP conjugated secondary antibody (Qiagen) followed by chemiluminescence development. All four Fabs specifically detected K63-linked diubiquitin (see FIG. 3). No binding to K48-linked diubiquitin was observed for any of the four Fabs tested.

(F) Conversion to IgG

The parental Fab Apu2.16 and the three affinity-matured Fabs Apu3.A8, Apu3.A12, Apu3.B3 were expressed in HEK293 cells as human IgGs. Expression constructs were generated by cloning the Fab variable domains into pRK mammalian expression constructs encoding the heavy and light chains of human IgG (Gorman et al., DNA Prot. Eng. Tech. 2: 3-10 (1990)). IgGs were purified by affinity chromatography on protein A-sepharose columns by standard methodologies.

Example 2

Detection of Endogenously Ubiquitinated Proteins

The activity of the affinity-matured anti-K63-linked polyubiquitin IgGs described in Example 1(F) was assessed. For western blot analyses, polyubiquitin or polyubiquitinated proteins were run on polyacrylamide gels and the contents of the gels were transferred to nitrocellulose blots following standard procedures in the art. The resulting nitrocellulose blots were blocked for approximately an hour in 10 mM Tris-HCl pH 7.5, 150 mM NaCl, 0.1% Tween-20 (TBST) containing 5% non-fat milk powder. The primary anti-K63-linked polyubiquitin antibody (either the parental Apu2.16 antibody in IgG format, or Apu3.A8, Apu3.A12, or Apu3.B3 in IgG format) was added to a final concentration of 5 µg/mL for a minimum of 1 hour at room temperature. Overnight incubations were performed at 4° C. The blots were washed three times in TBST, 10 minutes per wash. Bound anti-K63-linked polyubiquitin antibodies were detected with peroxidase-conjugated anti-human IgG (ICN Cappel) diluted 1:10,000 in TBST containing 5% non-fat milk powder. After one hour at room temperature, the blots were washed 3-6 times in TBST, incubated in Supersignal (Pierce) according to the manufacturer's instructions, and exposed to film. For the western blots of endogenously ubiquitinated proteins, 293T cells were transfected with or without a vector expressing 3×HA-tagged TRAF6 using Lipofectamine 2000 (Invitrogen). Cells were harvested two days post-transfection after culture in 25 µM MG-132 (Calbiochem) for the final hour. The cells were washed in phosphate-buffered saline and then protein extracts were prepared in ice-cold lysis buffer (20 mM Tris-Cl pH 7.5, 135 mM NaCl, 1.5 mM MgCl$_2$, 1 mM EGTA, 1% Triton X-100, 10% glycerol, 1 mM dithiothreitol, 2 mM N-ethyl-maleimide) supplemented with a complete protease inhibitor cocktail (Roche).

Figure 4:
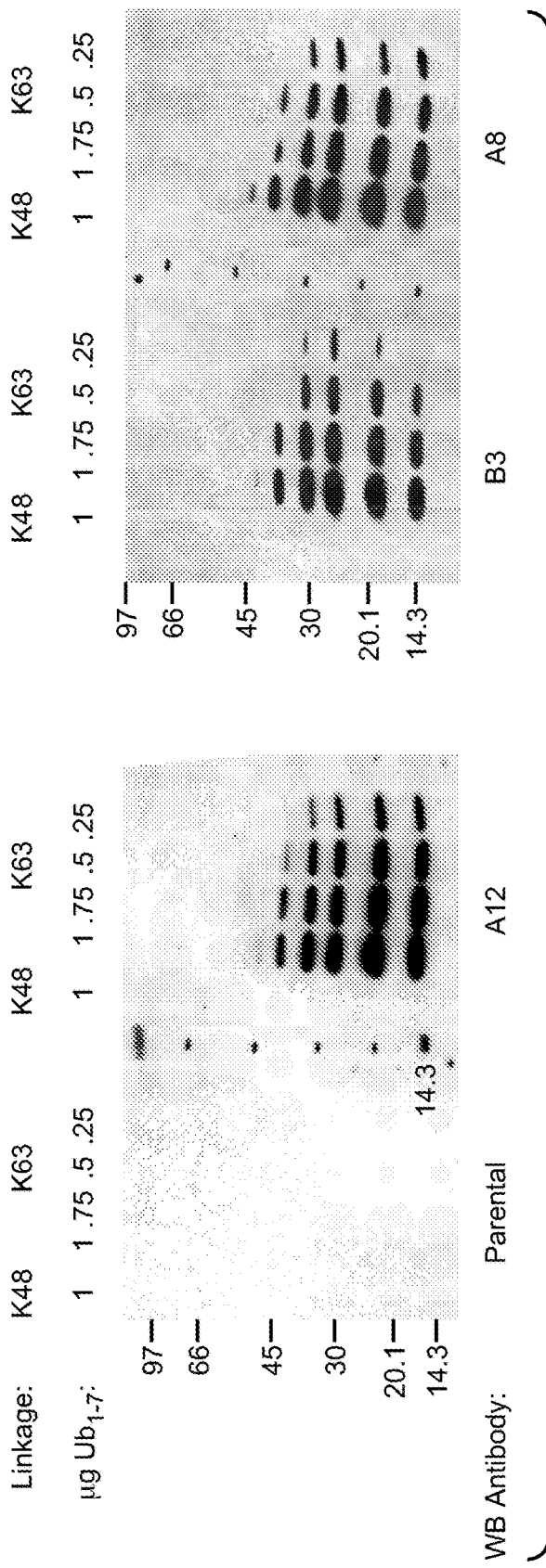
FIG. 4 depicts the results of western blotting experiments described in Example 2. The figure shows the poor binding of the parental Apu2.16 IgG to either immobilized K63-linked di- to heptaubiquitin or immobilized K48-linked di- to heptaubiquitin. The figure also shows the binding of each of the affinity-matured anti-K63-linked polyubiquitin antibodies Apu3.A12, Apu3.B3, and Apu3.A8 to immobilized K63-linked di- to heptaubiquitin and the absence of binding to immobilized K48-linked di- to heptaubiquitin.
Figure 5:
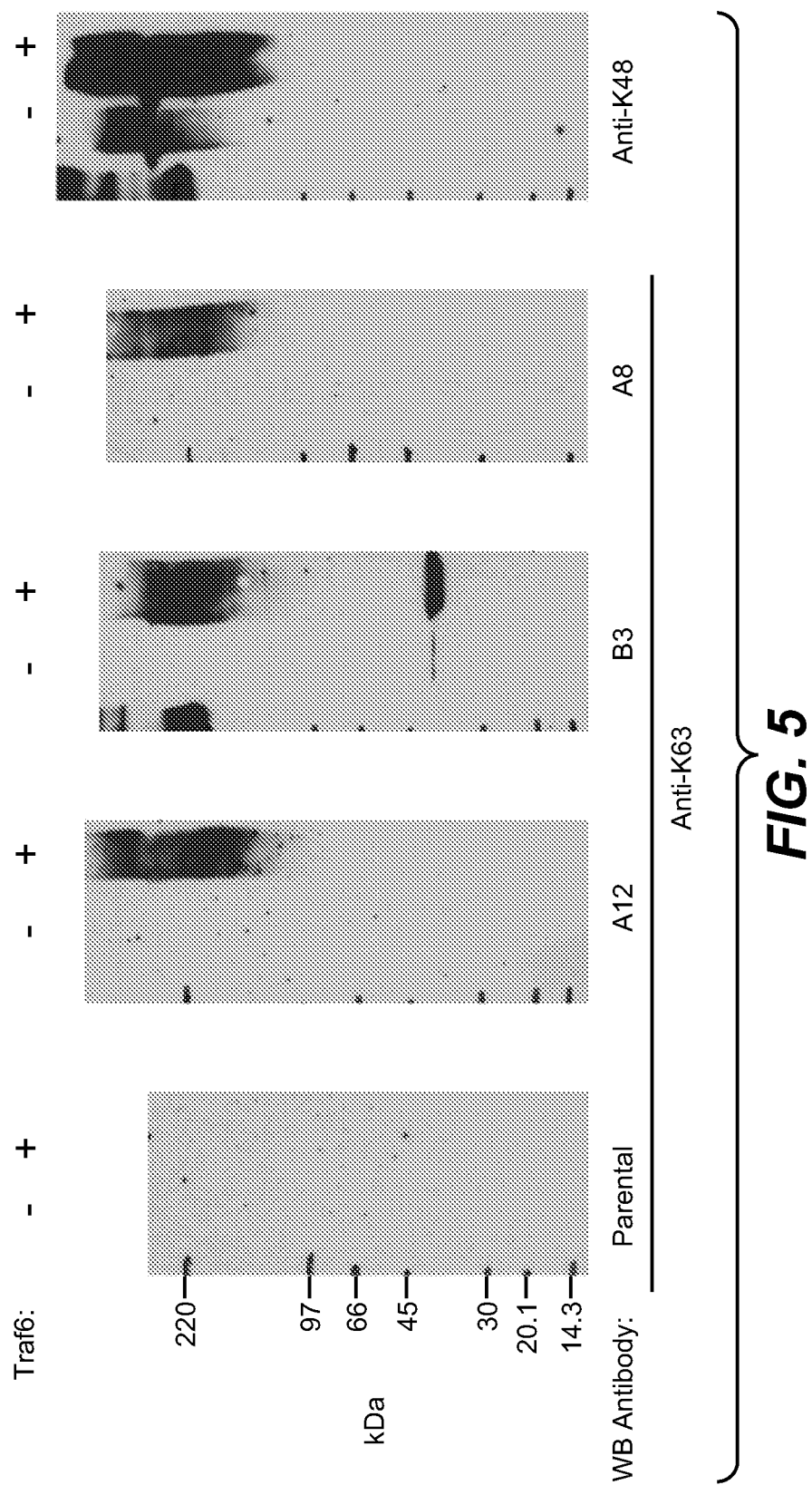
FIG. 5 depicts the results of western blotting experiments described in Example 2. The figure shows that though the parental anti-K63-linked polyubiquitin antibody Apu2.16 was not able to detect K63-linked ubiquitinated Traf6, the affinity-matured antibodies Apu3.A12, Apu3.B3, and Apu3.A8 were able to specifically detect K63-linked ubiquitinated Traf6 in a western blot format.

As shown in FIGS. 4 and 5, each of the three tested affinity-matured anti-K63-linked IgGs worked better in western blots than the parental Apu2.16 IgG. FIG. 4 depicts the results of a western blot against immobilized purified K48-linked or K63-linked polyubiquitin containing two to seven ubiquitin subunits. The parental IgG Apu2.16 did not detect K63-linked or K48-linked polyubiquitin of any number of ubiquitin subunits at any concentration tested. Affinity matured IgGs Apu3.A8, Apu3.A12, or Apu3.B3 detected K63-linked polyubiquitin containing 2 to 6 subunits at each concentration tested, and of seven subunits at all but the lowest concentration tested. No nonspecific binding to K48-linked polyubiquitin was observed with any of the three affinity-matured IgGs. To ascertain whether the affinity-matured antibodies were able to detect endogenously ubiquitinated proteins, 293T cells were transfected with TRAF6 and treated with MG-132, which has been found to result in K63-linked ubiquitination of TRAF6 in vivo (Wertz et al., Nature (2004) 430: 694-699). Similar to the western blot with immobilized purified polyubiquitin in FIG. 4, the parental Apu2.16 IgG was not able to detect K63-linked polyubiquitinated TRAF6 or any other K63-linked polyubiquitinated proteins in a western blot assay (FIG. 5). However, each of antibodies Apu3.A8, Apu3.A12, and Apu3.B3 specifically detected K63-linked polyubiquitinated TRAF6 and other K63-linked polyubiquitinated proteins in the same western blot assay (FIG. 5).

The preceding experiments confirmed that the affinity-matured antibodies were capable of detecting immobilized polyubiquitinated proteins. Further experiments were performed to ascertain whether these antibodies were able to immunoprecipitate polyubiquitinated proteins. For immunoprecipitation assays, the previously described lysis buffer also contained 6 M urea and the cells were lysed at room temperature for 15 minutes. Insoluble material was then removed by centrifugation and the soluble lysate diluted in regular lysis buffer to lower the urea concentration to 0.29M. Lysates were precleared with protein A-sepharose (GE) for 1 hour at 4° C. and then incubated with 5 pg of the antibody indicated for 1 hour at 4° C. Antibody complexes were captured with protein A-sepharose at 4° C. for 1 hour, washed extensively in lysis buffer, and eluted by boiling in Novex Tris-glycine SDS-sample buffer (Invitrogen) supplemented with 2.5% 2-mercaptoethanol.

Figure 6A:
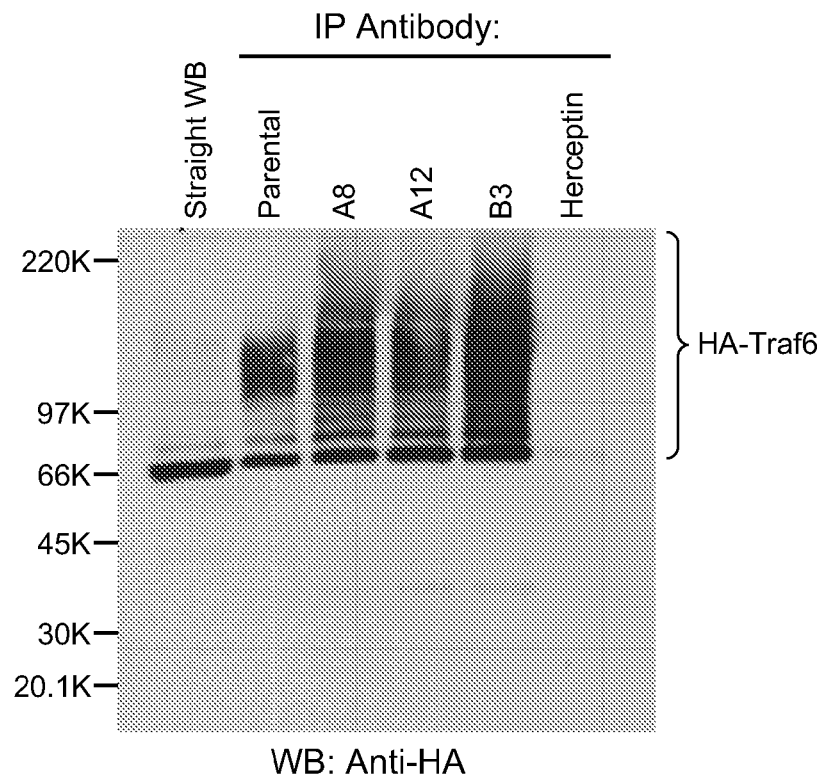
FIGS. 6A-B depict the results of a western blotting experiment to assess the ability of various anti-K63-linked polyubiquitin antibodies to immunoprecipitate K63-linked Traf6 from cellular lysates, as described in Example 2. The affinity-matured antibodies Apu3.A8, Apu3.B3, and Apu3.A12 were better able to immunoprecipitate K63-linked polyubiquitinated Traf6 than the parental antibody Apu2.16.
Figure 6B:
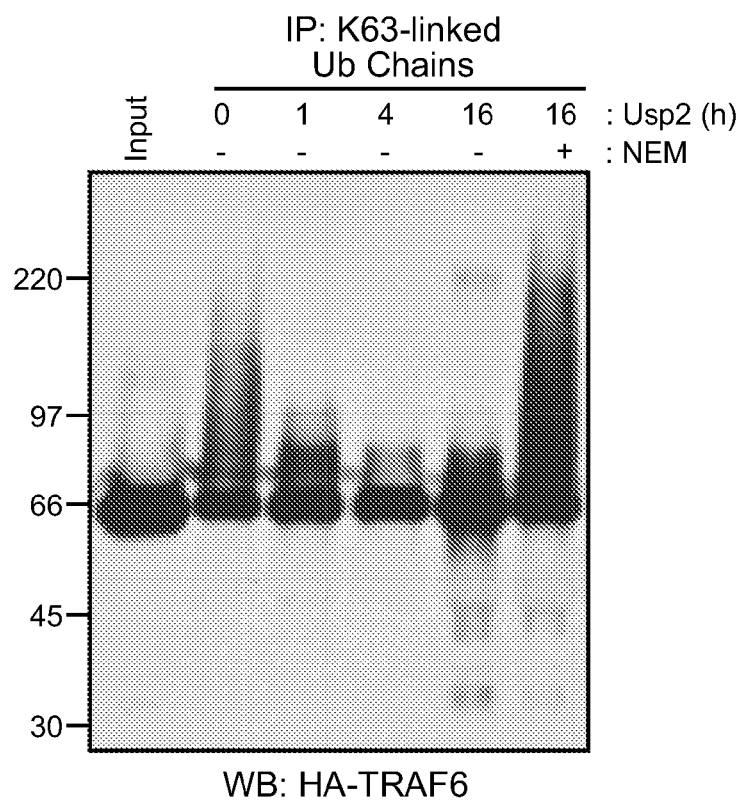

When TRAF6-containing lysates were denatured in the presence of 1% SDS to dissociate it from other ubiquitinated proteins, and immunoprecipitations were performed following dilution of the SDS to as low as 0.05%, no TRAF6 was captured by the K63-specific antibodies (data not shown). Immunoprecipitation of TRAF6 was successful, however, when TRAF6-expressing cells were lysed in the presence of an alternate denaturant: 6M urea. As shown in FIG. 6A, the three affinity-matured antibodies immunoprecipitated K63-linked polyubiquitinated Traf6 better than the parental antibody Apu2.16, showing that the affinity-matured antibodies were improved in binding to endogenously K63-ubiquitinated proteins in solution as compared to the parental anti-K63-polybuiqutin antibody. In further experiments, treatment of the immunoprecipitated K63-linked polyubiquitinated material with the promiscuous deubiquitinating enzyme Usp2 for increasing periods of time collapsed the smear of higher molecular weight bands observed in FIG. 6A and in the second lane of FIG. 6B, confirming that the immunoprecipitated TRAF6 was ubiquitinated (FIG. 6B, lanes 3-5). Non-specific proteolytic activity potentially associated with Usp2 was unlikely to have been responsible for the observed disappearance of the slower migrating species because inhibition of Usp2 deubiquitinating activity using the cysteine protease inhibitor N-ethylmaleimide (NEM) prevented collapse of the smear (FIG. 6B, lane 6). A portion of the TRAF6 immunoprecipitated by the K63-specific antibody Apu3.A8 appeared, by its migration, to be unmodified TRAF6, likely attributable to over-expression of TRAF6 inducing the formation of self-oligomers that trap unmodified TRAF6.

These results were confirmed by mass spectrometry experiments. When polyubiquitin chains are digested with trypsin, unique peptides corresponding to each of the 7 different types of lysine linkage may be observed. This follows the general consensus of a GlyGly motif on a miscleaved lysine. Each of the seven possible polyubiquitin chain linkages yields a unique peptide with a unique mass (when measured at 10 ppm mass accuracy) and also a unique fragmentation pattern upon collision-induced dissociation. Therefore using a high resolution mass spectrometer, along with targeted analysis against the specific signature peptides of interest one can monitor and quantitate the levels of abundance of either the K48 or K63 polyubiquitin chain linkage. Briefly, immunoprecipitation reactions from BJAB cells were performed as described above using an anti-K48-linked antibody, a mixture of the three affinity-matured anti-K63-linked polyubiquitin IgGs Apu3.A8, Apu3.A12, and Apu3.B3, or a control antibody (Herceptin®). Proteins were extracted from the beads chemically using acetonitrile:water+0.1% TFA, reduced, akylated, and digested with trypsin. A hybrid LTQ-Orbitrap mass spectrometer coupled to a nanoACQUITY™ UPLC (Thermo-Fisher Scientific) was used at a flow rate of 1 µL/minute with a one hour gradient (solvent A: water+0.1% formic acid; solvent B: acetonitrile+0.1% formic acid). The instrument was calibrated and tuned using tryptically digested synthetic tetraubiquitin (Boston Biochem) to validate optimum charge states for targeted analysis studies. The determined m/z for the K48-linked polyubiquitin were 487.6, 730.89, and 1460.78, and the determined m/z for the K63-linked polyubiquitin were 561.80, 748.73, and 1122.6. After tryptic digestion, reverse phase separation and targeted tandem mass spectrometry the ion chromatograms for the K48 and K63 polyubiquitin peptides were extracted and the peak area was calculated to infer concentration.

Figure 7A:
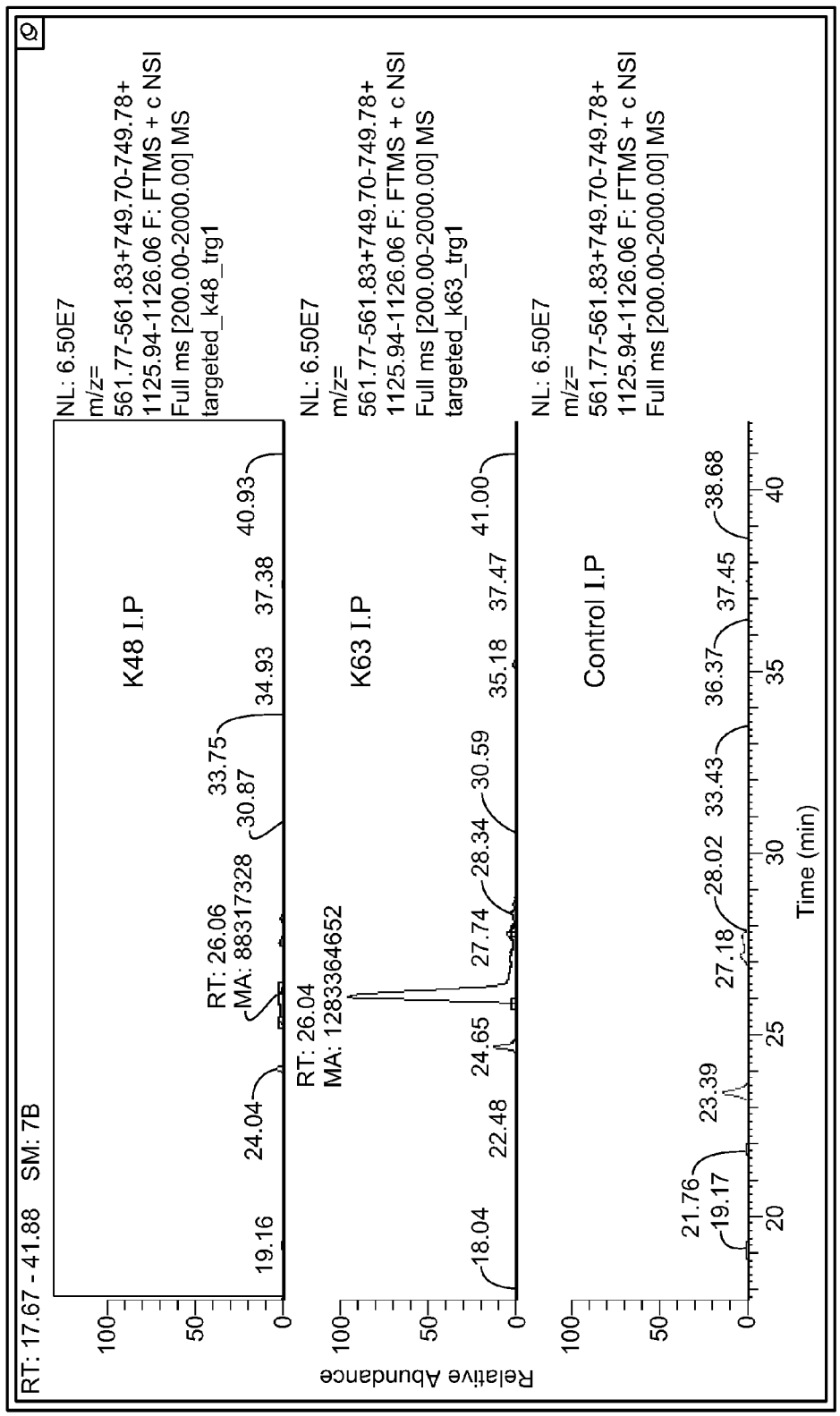
FIGS. 7A-K depict the results of confirmatory mass spectrometry experiments, as described in Example 3.
Figure 7B:
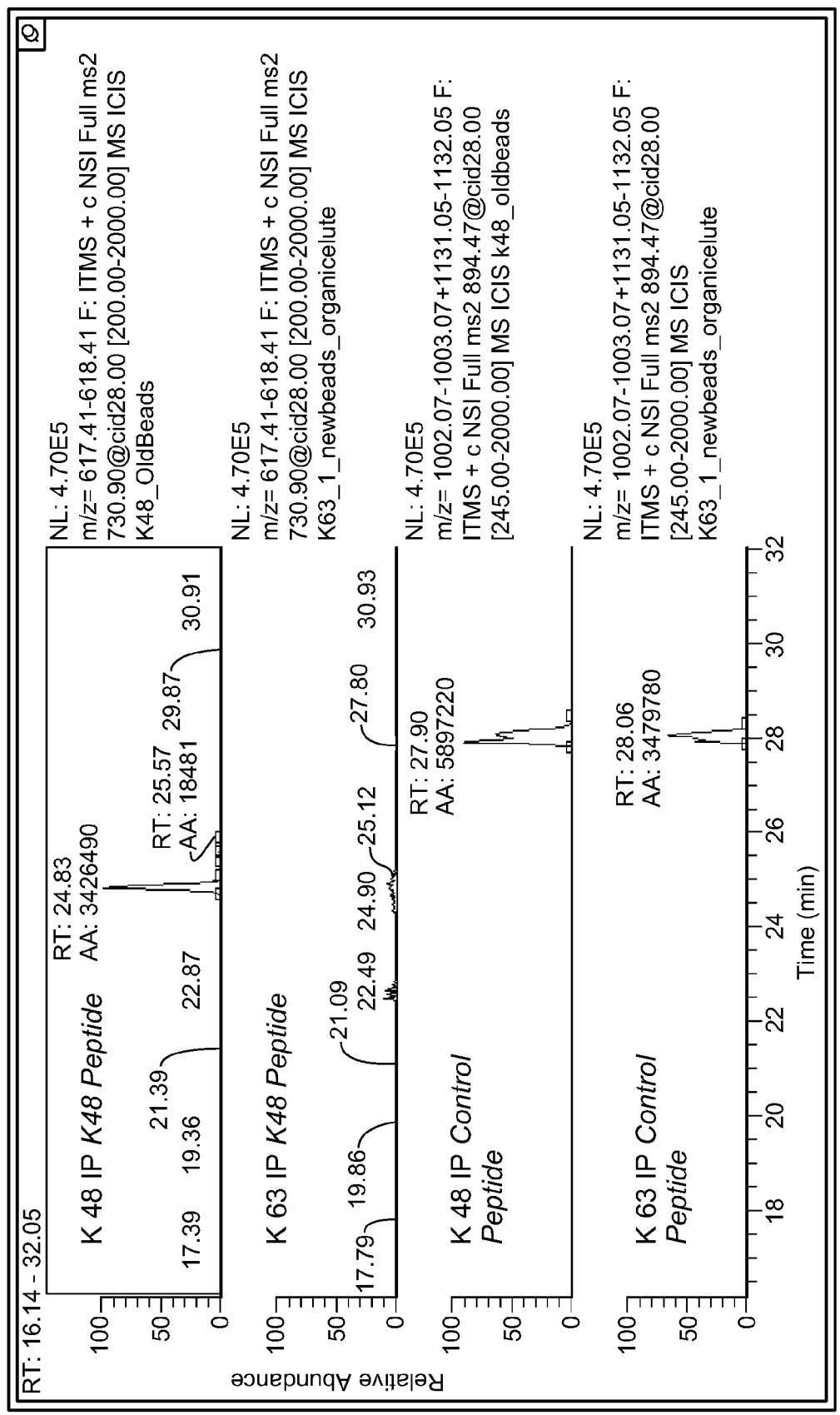

The results of the immunoprecipitation analyses are set forth in FIGS. 7A and 7B. As shown in FIG. 7A, the mixture of the three affinity-matured anti-K63-linked polyubiquitin antibodies specifically immunoprecipitated K63-linked polyubiquitinated proteins. The results in FIG. 7B show that the anti-K63-linked polyubiquitin antibodies are not cross-reactive for K48-linked polyubiquitin peptides (whereas for comparison the K48-linked polyubiquitin antibody shows substantial enrichment for the K48-linked polyubiquitin peptides).

In further mass spectrometry experiments, polyubiquitinated proteins were immunoprecipitated from human BJAB cells as described above, and then resolved by SDS-PAGE using standard methods. The immunoprecipitated gel-resolved proteins were subjected to in-gel trypsin digestion and then analyzed using a variation of the ubiquitin-AQUA method (Kirkpatrick et al., Nat. Cell Biol. 8: 700-710 (2006)). Briefly, the trypsin digests were supplemented with isotope-labeled internal standard peptides representing each polyubiquitin chain linkage and unbranched ubiquitin, and then the standards plus their corresponding native analytes were detected in high-resolution precursor ion scans using narrow range-extracted ion chromatograms (Crosas et al., Cell 127: 1401-1413 (2006)). The abundance of each polyubiquitin chain linkage and the total amount of ubiquitin in the BJAB immunoprecipitates was quantified by comparing the signal from each digested peptide relative to its corresponding internal standard. Specifically, BJAB cells were cultured in spinner flasks in the high-glucose version of Dulbecco's modified Eagle's medium supplemented with 100 µM L-asparagine, 50 µM 2-mercaptoethanol, and 10% fetal calf serum. Cells ($>10^9$) were washed in PBS and lysed for 30 minutes at room temperature in lysis buffer (20 mM Tris-HCl pH 7.5, 135 mM NaCl, 1.5 mM $MgCl_2$, 1 mM EGTA, 1% Triton X-100, 10% glycerol) containing 6 M urea, 2 mM N-ethylmaleimide (NEM) and a complete protease inhibitor cocktail (Roche). Insoluble material was removed by centrifugation and then the lysate was diluted to 4 M urea with lysis buffer supplemented with protease inhibitors, 2 mM NEM and 1 mM DTT. After preclearing with Protein A-sepharose (GE Healthcare) for one hour, the lysate was divided into three samples that received 30 µg of either Apu3.A8 anti-K63 (in IgG format), Apu2.07 anti-K48 (in IgG format), or isotype control antibody (anti-Her2). Samples were incubated at room temperature for two hours and subsequently centrifuged to remove precipitated material. Further antibody (10 µg) was added to the soluble lysate as well as Protein A-sepharose and samples were incubated at room temperature overnight. The sepharose beads were washed extensively in lysis buffer, then in PBS. The beads were eluted in reducing SDS sample buffer, alkylated with iodoacetamide, and then resolved by SDS-PAGE in 4-20% Tris glycine gels (Invitrogen). All areas of the gel (except for the 25 and 55 kDa regions representing the heavy and light chains from the precipitating antibodies) were excised, crushed, washed in 25 mM $NH_4HCO_3$ in 50:50 acetonitrile:water and dehydrated. The gel was then rehydrated in 25 mM $NH_4HCO_3$ containing trypsin (Promega) and incubated overnight at 37° C. The reaction was quenched by addition of 0.008% TFA. Peptides were extracted in 5% acetic acid and then twice in 100% acetonitrile. These samples were spiked with AQUA peptide standards (1 pmol) and injected via an auto-sampler for separation by reverse phase chromatography on a NanoAcquity UPLC system (Waters). Peptides loaded onto a pre-column (5 µm Symmetry® C18, 180×20 mm) were separated using an analytical column (1.7 µm BEH-130 C18 column 100×100 mm (Waters)) with a flow rate of 1 µL per minute and a gradient of 2% solvent B to 90% Solvent V (where Solvent A is water+0.1% formic acid and solvent B is 100% acetonitrile+0.1% formic acid) applied over 70 minutes with a total analysis time of 90 minutes. Peptides were eluted directly into a nanospray ionization source with a spray voltage of 2 kV and were analyzed using an LTQ XL-Orbitrap mass spectrometer (ThermoFisher). Precursor ions were analyzed in the FTMS at 60,000 resolution. Quantitation was performed by comparing peak areas for the heavy and light version of each peptide, extracting the ion chromatograms at 10 ppm mass accuracy to 4 decimal places.

MuRF1 autoubiquitination reactions were performed according to the manufacturer's instructions (Boston Biochem). For immunoprecipitations, samples were diluted 100-fold in lysis buffer containing 4 M urea, precleared with Protein A-sepharose, and then immunoprecipitated overnight with antibody (20 µg) and Protein A-sepharose. Total ubiquitin was blotted with P4D1 antibody (Santa Cruz Biotechnology). MuRF1 samples analyzed by mass spectrometry were resolved on an Agilent 1100 LC module with a 15 minute gradient from 5% solvent B to 30% Solvent B and a total analysis time of 30 minutes. Ion chromatograms were created by extracting a window ±15 ppm from the expected m/z.

Figure 7C:
Figure 7D:
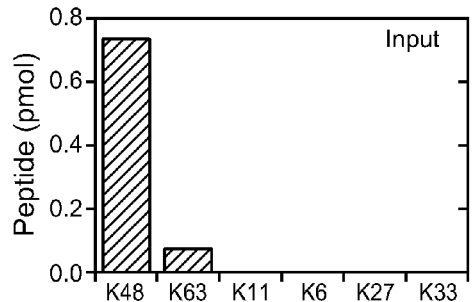
Figure 7E:
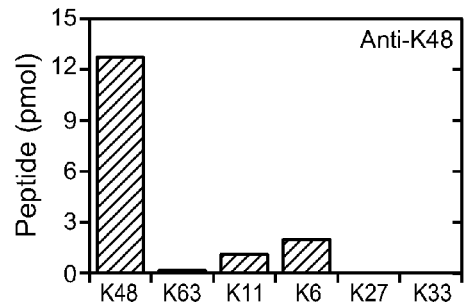
Figure 7F:
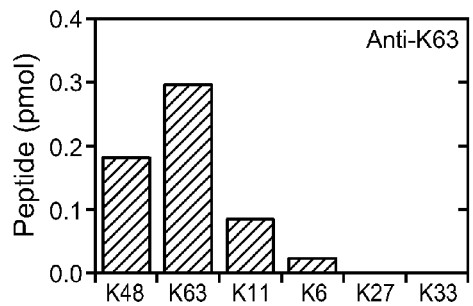

Anti-K48-linked polyubiquitin antibody Apu2.07, the anti-K63-linked polyubiquitin antibody Apu3.A8 and an isotype control antibody recognizing Her2 immunoprecipitated 49.1 pmol, 2.2 pmol and 0.2 pmol of total ubiquitin, respectively (FIG. 7C). This result was in keeping with the observation that K48-linked polyubiquitin chains were more abundant than K63-linked polyubiquitin chains in the input lysate used for the immunoprecipitations (FIG. 7D). Direct examination of the polyubiquitin linkages immunoprecipitated by the anti-K48 antibody revealed 12.7 pmol of K48-GG signature peptide and residual amounts of the signature peptides for certain other linkages (0.1 pmol K63, 1.1 pmol K11, and 2.0 pmol K6) (FIG. 7E). Similarly, polyubiquitin chains immunoprecipitated by the anti-K63 linked polyubiquitin antibody Apu3.A8 mainly produced the K63-GG signature peptide (0.3 pmol K63), and lesser amounts of other linkage peptides (0.18 pmol K48, 0.08 pmol K11, and 0.06 pmol K6) (FIG. 7F). Given the strong binding preferences seen for the anti-polyubiquitin antibodies by surface plasmon resonance, these mass spectrometry results suggest that a significant fraction of cellular substrates modified by ubiquitin exhibit heterogeneous polyubiquitin chain linkages.

Figure 7G:
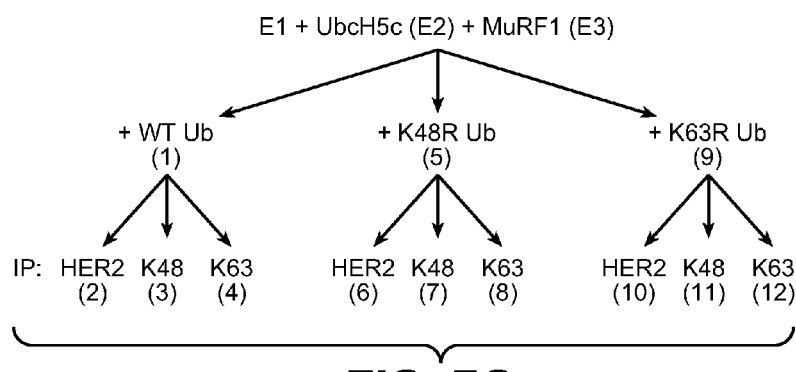
Figure 7H:
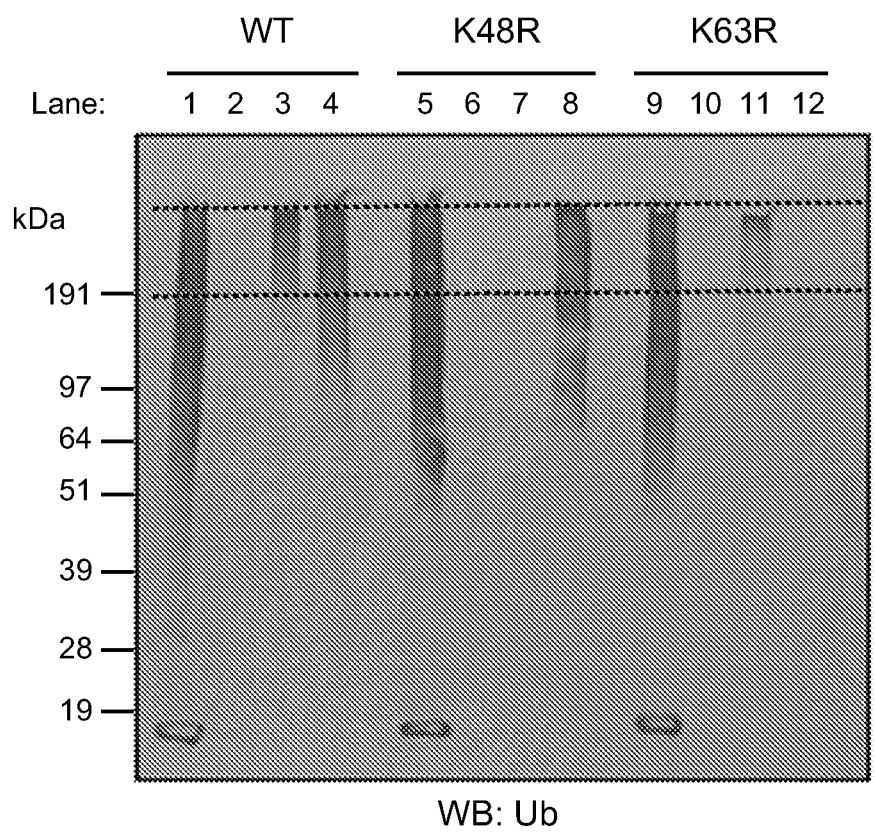
Figure 7I:
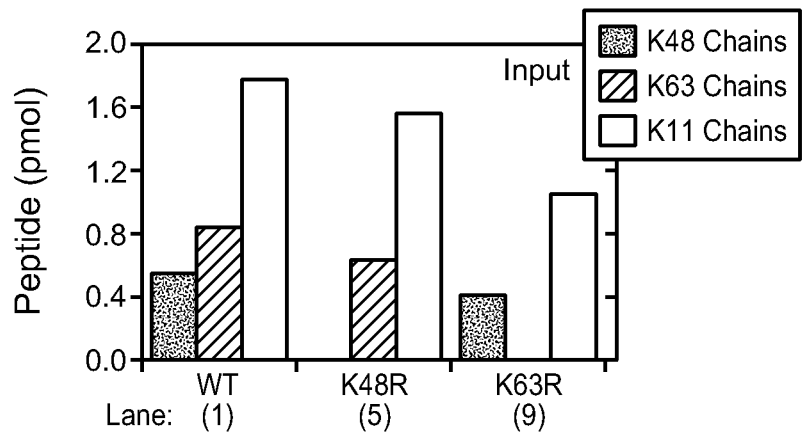
Figure 7J:
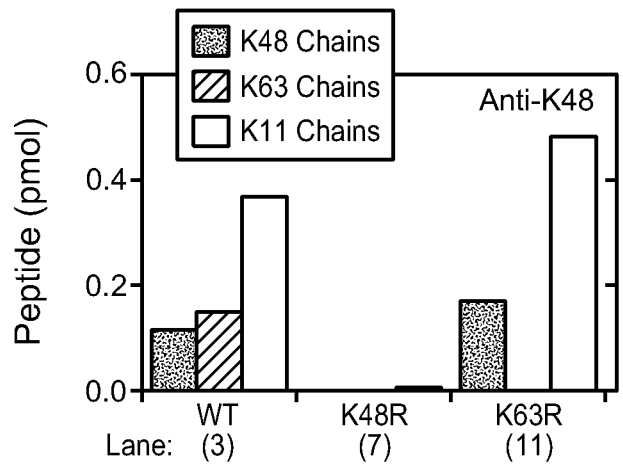
Figure 7K:
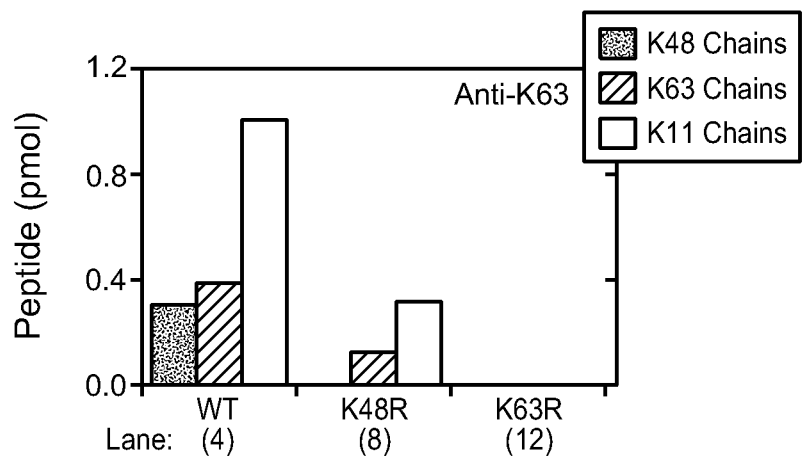

To confirm that these "off-target" linkages immunoprecipitated from BJAB cell lysates were derived from substrates bearing heterogeneous polyubiquitin chains, as opposed to non-specific binding, the necessity of the target linkage for immunoprecipitation of the "off target" linkages was investigated. Mixed linkage polyubiquitin chains lacking either the K48 or the K63 linkage were generated in vitro using E3 MuRF1 in combination with the promiscuous E2 enzyme UbcHSc (Kim et al. J. Biol. Chem. 282: 17375-17386 (2007)). The K48 or K63 linkage was excluded from the MuRF1 autoubiquitination reactions using mutant ubiquitin that had either K48 or K63 mutated to arginine (FIG. 7G). By western blotting with a pan-ubiquitin antibody, MuRF-1 autoubiquitination reactions produced high molecular weight smears irrespective of whether wild-type, K48R, or K63R ubiquitin was used (FIG. 7H, lanes 1, 5, and 9). Ubiquitin-AQUA analysis of the reaction with wild-type ubiquitin revealed three main linkages: K48, K63, and K11 (FIG. 7I, lane 1). As expected, reactions performed with K48R ubiquitin lacked K48-linked polyubiquitin chains (FIG. 7I, lane 9). Both the anti-K48-linked and anti-K63-linked polyubiquitin antibodies immunoprecipitated polyubiquitinated species when MuRF1 was modified with wild-type ubiquitin (FIG. 7H, lanes 3-4), but each antibody failed to do so if the target linkage for which it was specific was absent (FIG. 7H, lanes 7 and 12). An isotype-matched control antibody (anti-HER2) did not immunoprecipitate ubiquitinated MuRF1 from any of the reactions (FIG. 7H, lanes 2, 6, and 10). Ubiquitin-AQUA analysis of the immunoprecipitated species form the wild-type Ub reaction demonstrated the presence of K48-, K63-, and K11-linked chains regardless of the antibody used for enrichment (FIG. 7J, lane 3 and FIG. 7K, lane 4). As predicted by Western blotting (FIG. 7H, lanes 7 and 12), K11-linked chains were immunoprecipitated by both the anti-K48-linked and the anti-K63-linked polyubiquitin antibodies only if their target linkage was also present (FIGS. 7J and 7K). These results demonstrated that the anti-K48-linked and anti-K63-linked polyubiquitin antibodies retain their fidelity in the context of immunoprecipitation. Further, they indicate that alternative linkages immunoprecipitated from cells by the anti-K48-linked and anti-K63-linked polyubiquitin antibodies must stem from individual substrates bearing both target and off-target linkages.

Example 3

Ubiquitination Pathway Detection Using Affinity-Matured Antibodies

A number of cellular pathways have been identified that are regulated by polyubiquitination of key proteins. The affinity-matured anti-K63-linked polyubiquitin antibodies of the invention were used to determine the extent of K63-linked polyubiquitination of particular proteins in the cell, helping to elucidate cellular signaling pathways where ubiquitination with K63-linked polyubiquitin plays a role.

(A) TNFα Activation of TNFR1

Figure 8A:
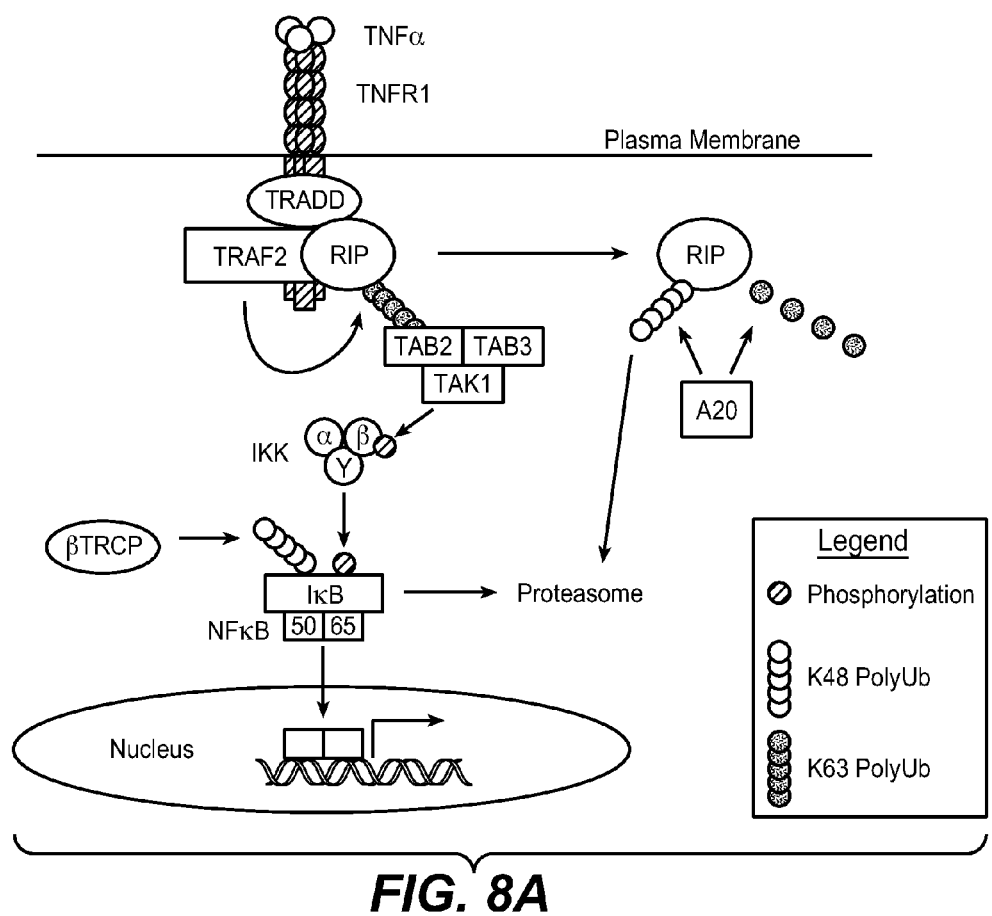
FIG. 8A schematically depicts the signaling pathway stimulated by tumor necrosis factor alpha (TNFα) binding to tumor necrosis factor receptor 1 (TNFR1) in vivo.

TNFα activation of tumor necrosis factor receptor 1 (TNFR1) leads to RIP and TRAF2 association (see FIG. 8A). TRAF2 adds K63-linked polyubiquitin chains to RIP which allows recruitment of TAK1/TAB2/TAB3 and subsequent activation of the NFκB signaling pathway (see Wertz et al., Nature (2004) 430: 694-699). Downregulation of signaling through this pathway occurs by the deubiquitinase A20 removing the K63-linked polyubiquitin chains on RIP and replacing them with K48-linked polyubiquitin chains, targeting RIP to the proteasome for degradation. The affinity matured anti-K63-linked polyubiquitin antibodies of the invention were used to assess the degree and type of polyubiquitination of RIP during various perturbations of the pathway.

Briefly, HeLa S3 cells were treated with 21 μM MG-132 for ten minutes. The cells were subsequently treated with 100 ng/mL TNF from 0 to 25 minutes. At each timepoint, the cells were pelleted and washed once with PBS. The washed pellet was lysed in 20 mL TNFR1 immunoprecipitation buffer (20 mM Tris, 150 mM NaCl, 1% Triton X-100, and 1 mM EDTA) including protease inhibitors, 25 μM MG-132, 10 mM N-ethyl maleimide (NEM), and 50 mM NaF for 10 minutes at 4° C. with rotation. Lysates were centrifuged at 10,000×g for 5 minutes. The cleared lysate was incubated with 200 μL Protein A beads for one hour at 4° C. with rotation. Beads and debris were pelleted by centrifugation at 2,000 rpm for 5 minutes. Samples were taken from each timepoint lysate for western blot analysis as described above. For immunoprecipitation samples, 20 μL anti-TNFR1 antibody was added to each sample, and the samples were rotated at 4° C. for 2.5 hours. 200 μL unblocked protein A beads were added to each sample, and the samples were again rotated at 4° C. for 2.5 hours. The beads were washed twice with immunoprecipitation buffer, twice in immunoprecipitation buffer including 1 M NaCl, and twice in immunoprecipitation buffer. Proteins specifically bound to the beads were recovered by treatment with ubiquitin chain lysis buffer (20 mM Tris-Cl pH 7.5, 135 mM NaCl, 1.5 mM $MgCl_2$, 1 mM EGTA, 1% Triton X-100 and 10% glycerol) containing 6 M urea and gentle agitation for 15 minutes at room temperature. The beads were pelleted by centrifugation. Supernatants were diluted 25-fold with ubiquitin chain lysis buffer including protease inhibitors, 10 mM NEM and 0.5 mM dithiothreitol, followed by preclearing with 50 μL Protein A beads+10 μg Herceptin for 2 hours. Anti-K48-linked polyubiquitin antibodies and anti-K63-linked polyubiquitin antibodies (1:1 mixture of Apu3.A8 and Apu3.B3) were pre-coupled to protein A beads for 3 hours at 4° C. Immunoprecipitation reaction samples were combined with one of the precoupled antibodies and rotated for 2 hours at 4° C., followed by washing in lysis buffer and the addition of sample buffer. Samples were reduced and alkylated and run on 4-12% Tris/Gly 1.5 mm 15-well Novex gels, followed by transfer, immunoblotting, and western blot analysis according to the procedures described above in Example 2.

Figure 9A:
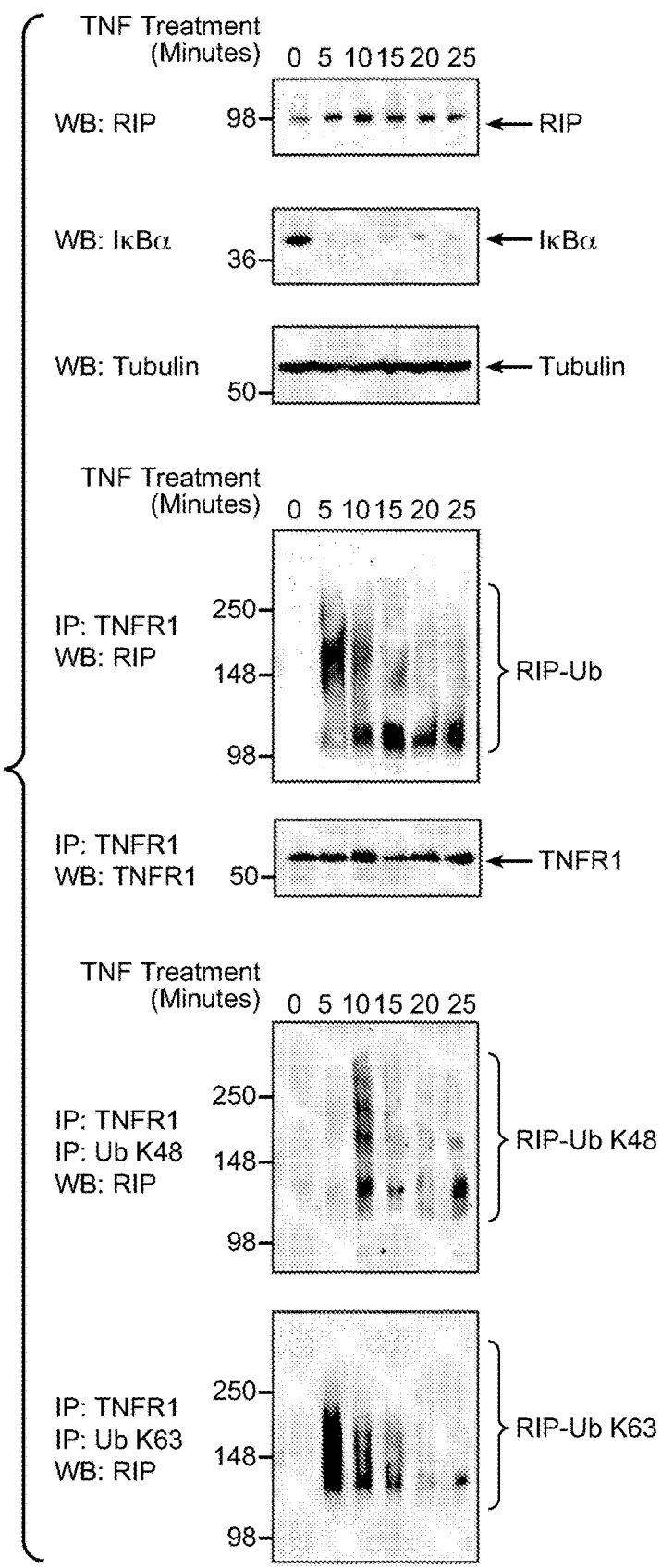
FIG. 9A shows western blots from immunoprecipitation experiments to detect the ubiquitination state of RIP, as described in Example 3. For the purpose of describing this figure only, the blots are assigned sequential numbers from 1 to 7, with the topmost blot having assigned number 1 and the bottom-most blot having assigned number 7. The blot 6 includes samples that were immunoprecipitated with anti-K48-linked IgG to capture K48-linked polyubiquitinated proteins. The blot 7 includes samples that were immunoprecipitated with a 1:1 cocktail of Apu3.A8 and Apu3.B3 to capture K63-linked polyubiquitinated proteins. Both blots were stained with an anti-RIP antibody. The blots 1-3 show control western blots to demonstrate that the levels of RIP and tubulin remain relatively constant during TNFα treatment (blots 1 and 3), while IκBα levels decrease upon TNFα treatment (blot 2). Blots 4 and 5 show control western blots to demonstrate that RIP is co-precipitated during an immunoprecipitation for TNFR1 (blot 4), and that the levels of TNFR1 remain constant during TNFα treatment (blot 5).
Figure 9B:
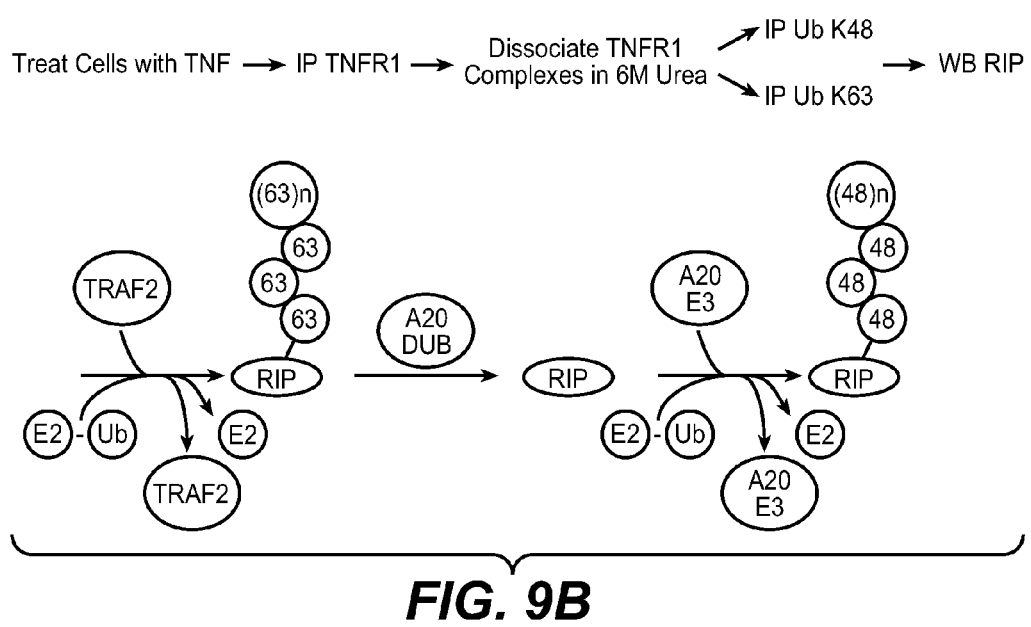
FIG. 9B schematically depicts the cellular pathway by which K63-linked polyubiquitin is added to RIP and replaced with K48-linked polyubiquitin by A20.

A simplified form of the known RIP modification pathway is shown schematically in FIG. 9B. Treatment of HeLa S3 cells with TNFα stimulates K63-linked polyubiquitination of RIP, which is in a complex with TNFR1. A two-stage immunoprecipitation (first immunoprecipitating the TNFR1 complex, then immunoprecipitating K48-linked polyubiquitinated proteins, or K63-linked polyubiquitinated proteins) permitted an analysis of the ubiquitination state of RIP upon TNFα treatment. As depicted in FIG. 9A, RIP protein quickly associates with TNFR1 within the first five minutes of TNFα treatment, and the amount of associated RIP remains constant regardless of the time of TNFα treatment thereafter (blot 4). The RIP that is initially associated with TNFR1 is K63-linked polyubiquitinated, but longer treatment with TNFα leads to chain editing, resulting in K48-linked polyubiquitinated RIP (compare blots 6 and 7). Thus the ability to discriminate between RIP bearing a K63-linked polyubiquitin label versus RIP bearing a K48-linked polyubiquitin label provides important information about a cellular pathway triggered by TNFα, and the affinity-matured antibodies of the invention provide a convenient and useful tool for examining this RIP-mediated pathway without performing mass spectrometry or other biophysical analyses.

(B) Polyubiquitin Chain Editing of IRAK1

Given that the kinase RIP1 is modified sequentially by K63- and then K48-linked polyubiquitin chains, the latter being conferred by the E3 deubiquitinase A20, and that A20 is also a known negative regulator of signaling by certain TLRs (Boone et al. Nat. Immunol. 5: 1052-1060 (2004)), other kinase adaptors recruited to TLRs and the interleukin-1 receptor (IL-1R) were investigated for regulation in a similar fashion. IRAK1 was a potential candidate for undergoing polyubiquitin chain editing because post-translationally modified IRAK is recruited rapidly to activated receptor complexes and subsequently is degraded (Yamin and Miller J. Biol. Chem. 272: 21540-21547 (1997)). 293 cells stably expressing IL-1R and IL1R-AcP were treated with 25 µM MG-132 just prior to the addition of 10 ng/mL IL-1β (eBioscience). Cells were washed with PBS and lysed in IRAK IP buffer (20 mM HEPES pH 7.6, 150 mM NaCl, 1.5 mM MgCl$_2$, 2 mM EGTA, 10 mM NaF, 2 mM DTT, and 0.5% Triton X-100) containing 6 M urea. Soluble lysates were diluted approximately 20-fold in lysis buffer and immunoprecipitations with either anti-K48-linked polyubiquitin antibody Apu2.07 or a 1:1 mix of anti-K63-linked polyubiquitin antibody Apu3.A8 and Apu3.B3 were performed as described above in Example 3(A) for RIP1. The IRAK1 antibody was obtained from Santa Cruz Biotechnology.

Figure 8B:
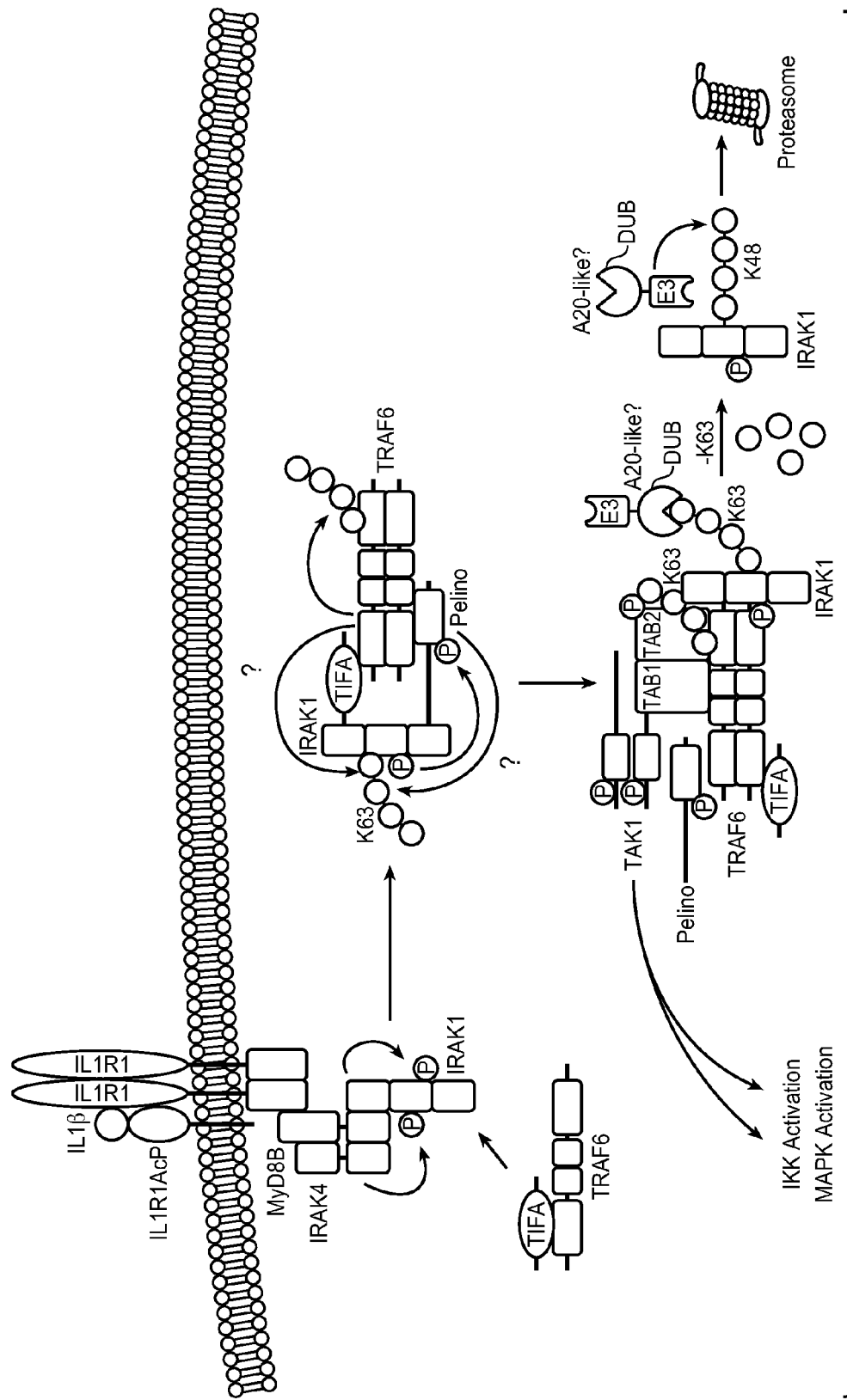
FIG. 8B schematically depicts the the signaling pathway stimulated by IL-1β binding to IL-1R1 in vivo.
Figure 10A:
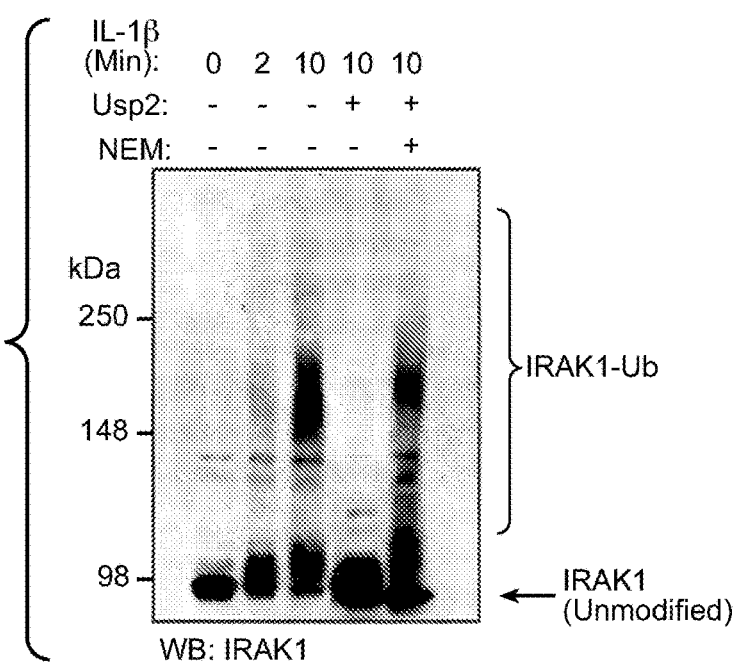
FIGS. 10A-D show the results of experiments described in Example 3(B) assessing the polyubiquitination state of IRAK1 after IL-1β stimulation of cells. Total IRAK1, IκBα and tubulin levels are shown in FIGS. 10A and 10B.
Figure 10B:
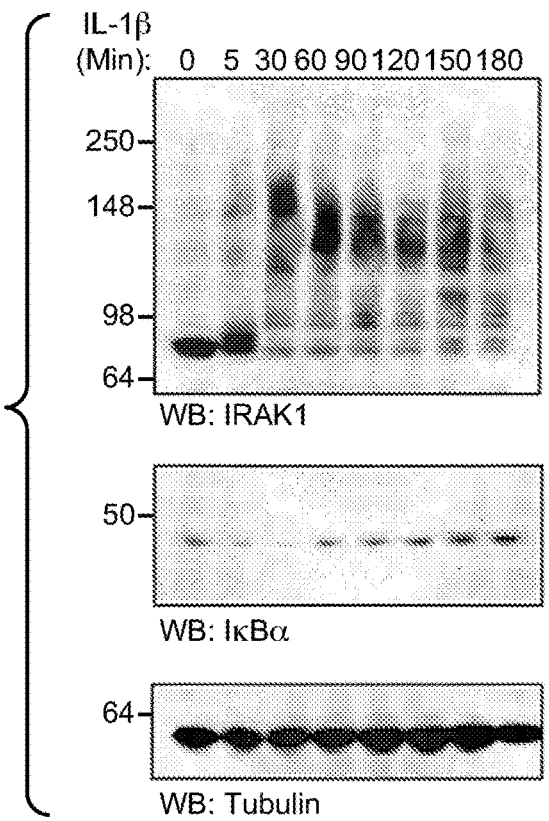
Figure 10C:
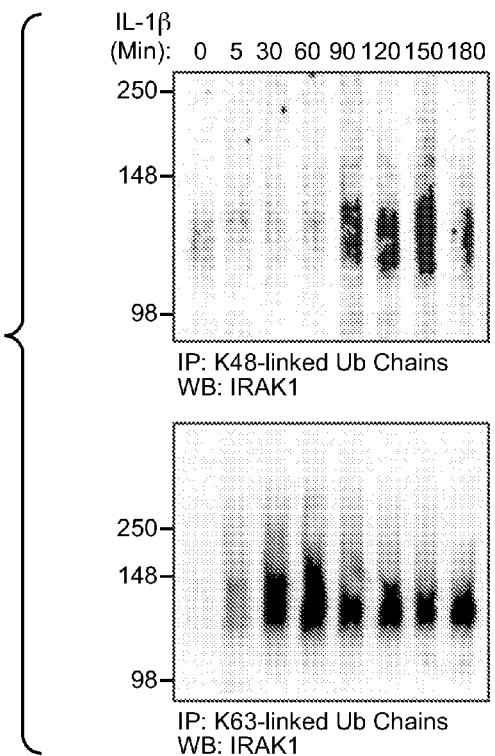
Figure 10D:
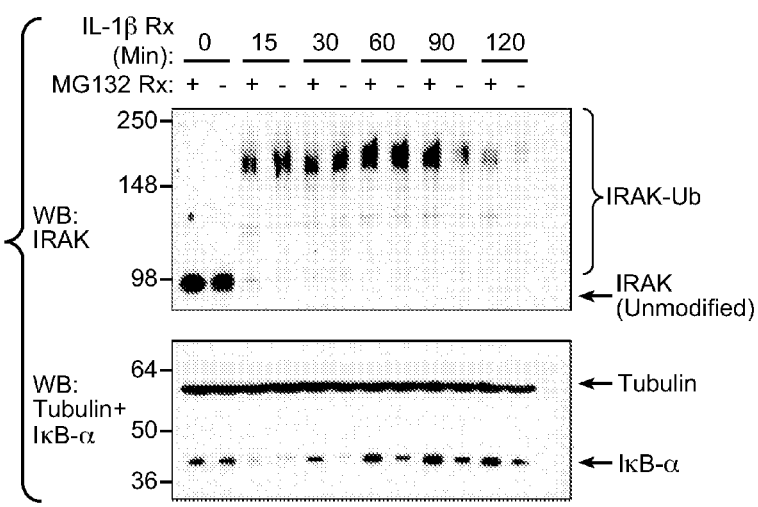
Figure 11A:
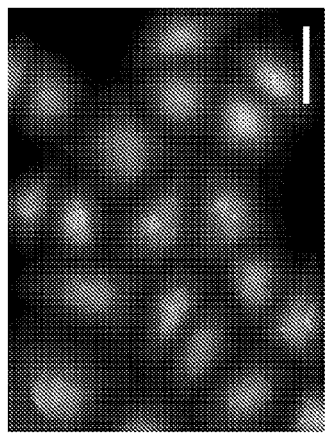
FIGS. 11A-F depict immunofluorescence microscopy images of HeLa cells stained with an anti-K48-linked polyubiquitin antibody or an anti-K63-linked polyubiquitin antibody alone (FIG. 11A or FIG. 11D, respectively) or further including a polyclonal antibody recognizing 20S proteasome subunits (FIGS. 11B and 11E, respectively), as described in Example 5. The arrow indicates mid-body staining. In the merged images (FIGS. 11C and 11F), very bright staining indicates potential colocalization and less bright staining corresponds to DAPI-labeled nuclei. The bars in each figure represent 50 µm.
Figure 11B:
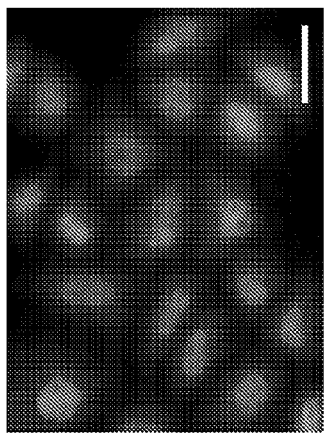
Figure 11C:
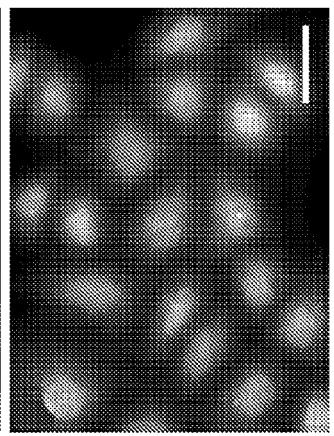
Figure 11D:
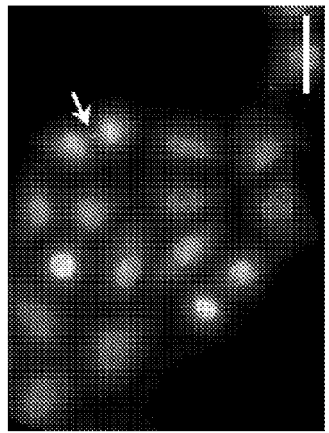
Figure 11E:
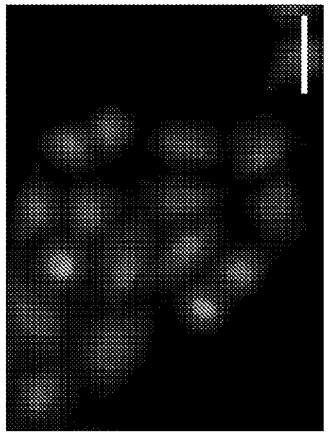
Figure 11F:
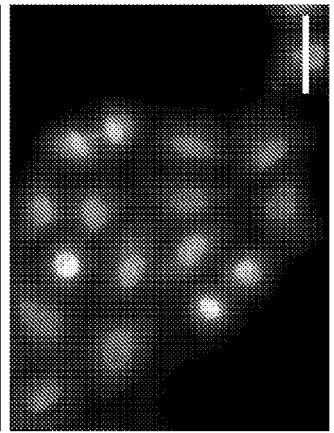

Upon treatment with IL-1β, cells stably expressing the IL-1R revealed a smear of modified IRAK1 within two minutes (FIG. 10A). The slower-migrating forms of IRAK1 were more abundant at 10 minutes and could be converted to the unmodified form of IRAK1 by Usp2 in an NEM-sensitive manner. These results suggested that the higher molecular weight forms of IRAK1 are due to ubiquitination. The appearance of ubiquitinated IRAK1 coincided with activation of downstream NF-κB signaling as evidenced by IKBα degradation (FIG. 10B). At different times after treatment with IL-1β, cell lysates were prepared in 6 M urea and immunoprecipitated with linkage-specific polyubiquitin antibodies prior to Western blotting for IRAK1 (FIG. 10C). IRAK1 modified with K63-linked polyubiquitin chains was detected at 5 minutes after IL-1β treatment and was maximal by 30-60 minutes post treatment, mirroring the timing of appearance of the high molecular weight IRAK1 smear (compare the upper panel of FIG. 10B with the lower panel of FIG. 10C). The amount of K48-linked polyubiquitin evident on IRAK1 peaked at 90-150 minutes, after which time the intensity of the total IRAK1 signal began to subside. When cells were treated with IL-1β in the presence of the proteasome inhibitor MG-132, this degradation of ubiquitinated IRAK1 was inhibited (FIG. 10D), consistent with the K48-linked polyubiquitin chains targeting IRAK1 for proteasomal degradation. Thus polyubiquitin chain editing of IRAK1 in cells treated with IL-1β resembles that of RIP1 in cells treated with TNF and this process of polyubiquitin chain editing may represent a general mechanism of terminating downstream signaling events. As described above for RIP, the ability to discriminate between IRAK1 bearing a K63-linked polyubiquitin label versus IRAK1 bearing a K48-linked polyubiquitin label provides important information about a cellular pathway triggered by IL-1β (see FIG. 8B), and the affinity-matured antibodies of the invention provide a convenient and useful tool for examining this IRAK1-mediated pathway without performing mass spectrometry or other biophysical analyses.

Example 4

Crystal Structure of APU3.A8 in Complex with K63dUB

To understand the structural consequences of the observed affinity and specificity improvements in Apu3.A8, the Fab fragment was crystallized in complex with K63-linked diubiquitin and the structure was solved to 2.6 A resolution (FIG. 2C). Briefly, the Fab fragment of Apu3.A8 was expressed in E. coli, purified using Protein G-sepharose, and eluted with 0.58% acetic acid. Fab-containing fractions were purified using an SP HiTrap column (GE Healthcare) equilibrated in 20 mM MES pH 5.5 and eluted with an NaCl gradient. The protein was further purified by passing it over an S-200 column (GE Healthcare) in 20 mM Tris-HCl pH 7.3, 150 mM NaCl. K63-linked diubiquitin was produced by incubating 4.1 mM ubiquitin (K63R and D77), 0.1 µM E1 (Boston Biochem), and 20 µM E2 (UbcH13/Uev1a for K63) (Boston Biochem) in 50 mM Tris-HCl, 5 mM MgCl$_2$, 0.5 mM DTT, 2.5 mM ATP overnight at 37° C. (see, e.g., Pickart and Raasi, Meth. Enzymol. 399: 21-36 (2005)). Diubiquitin was purified using a MonoS cation exchange column in a NaCl gradient and 20 mM MES pH 5.5, and then concentrated to 0.5 mg/mL. Diubiquitin-Fab complexes were prepared from 3-fold molar excess of Fab with diubiquitin. The protein complex was purified over a Superdex 75 column in 20 mM Tris-HCl pH 7.3, 150 mM NaCl. Complex fractions were pooled and concentrated to 17 mg/mL for crystallization screening trials. Crystals of K63R diubiquitin-Apu3.A8 (90 µm×90 µm×150 µm) grew after two weeks at 18° C. in sitting drops from 1:1 mixtures of protein (17 mg/mL in 20 mM Tris-HCl pH 7.3, 150 mM NaCl) and well solution (0.1 M Tris-HCl pH 8.0, 1.6 M LiSO$_4$). Crystals were cryoprotected using well solution with the addition of 30% glycerol. Crystallographic data was collected at SSRL beamline 7-1 (Table D) and was processed with HKL (HKL). The structure was solved by molecular replacement using the program PHASER (CCP4) followed by refinement with REFMAC5 (CCP4). The Apu3.A8 complex was solved using the refined Apu2.16 complex as a search model (see FIG. 2A and US Patent Publication No. US2007-0218069) (FIGS. 2C and 2D). All figures were made with PyMol (www.pymol.org).

TABLE D

| X-Ray Data Collection and Refinement Statistics | | |
|---|---|---|
| | Ubq-Apu2.16 | Ubq-Apu3A8 |
| Data collection | | |
| Space group | C2 | C2 |
| Cell dimensions | | |
| a, b, c (Å) | 177, 95, 98 | 107, 88, 90 |
| β (°) | 107 | 108 |
| Resolution (Å) | 50-2.7 (2.80-2.70) | 50-2.6 (2.69-2.60) |
| R$_{sym}$ | 5.0 (52.6) | 5.1 (58.0) |
| <I/σI> | 15.9 (1.9) | 11.6 (1.9) |
| Completeness (%) | 99.2 (100) | 98.1 (97.9) |
| Redundancy | 3.8 (3.9) | 3.8 (3.9) |
| Refinement | | |
| Resolution (Å) | 30-2.7 | 50-2.6 |
| Complex in asu | 2 | 1 |
| No. reflections | 40,137 | 21,569 |
| R$_{work}$/R$_{free}$ (%) | 22.1, 27.3 | 24.0, 30.1 |
| No. atoms | | |
| Protein | 8914 | 4469 |
| Solvent | 0 | 25 |
| R.m.s. deviations | | |
| Bond lengths (Å) | 0.009 | 0.009 |
| Bond angles (°) | 1.2 | 1.1 |

*Values in parentheses are for highest-resolution shell.

The resulting structure showed that the changes in L2 and H2, which had greatly improved the specificity, had relatively little impact on the structure of the Fab (FIG. 2C). Excluding differences in the conformation of CDR L3 and the N-terminal strand of the light chain, both of which are attributable to differences in crystal packing, the structure of the A8 Fab is virtually identical to the structure of the parental A16 Fab (rmsd 0.08 Å on 412 C-α atoms). Both structures were compared to the Fv region of the humanzied anti-HER2 antibody 4D5 (FIG. 2D). The conformation of L1 and the N-termini of the three Fabs differ considerably. The C-alpha atom of T5 is displaced by 14 Angstroms between the structures of either Apu2.16 or Apu3.A8 and humanized 4D5, despite identical sequences among the three structures in these regions. The conformation and sequence of L3 differs considerably as well. These differences combined to affect the position of Q90 in Apu3.A8 such that it occupies the space normally occupied by the N-terminal strand, resulting in displacement of this strand with concomitant rearrangement of L1. Comparison of the structure of K63 diubiquitin in the above co-crystal structure that of a crystal structure of K63-diubiquitin alone (pdb code 2JF5) or to either the crystal or solution structures of K48 diubiquitin (Cook et al., J. Biol. Chem. 267: 16467-16471 (1992); Varadan et al., J. Mol. Biol. 324: 637-647 (2002)) demonstrates that the Fabs recognize a specific conformation of diubiquitin that is unique to the K63 linkage.

Figure 2E:
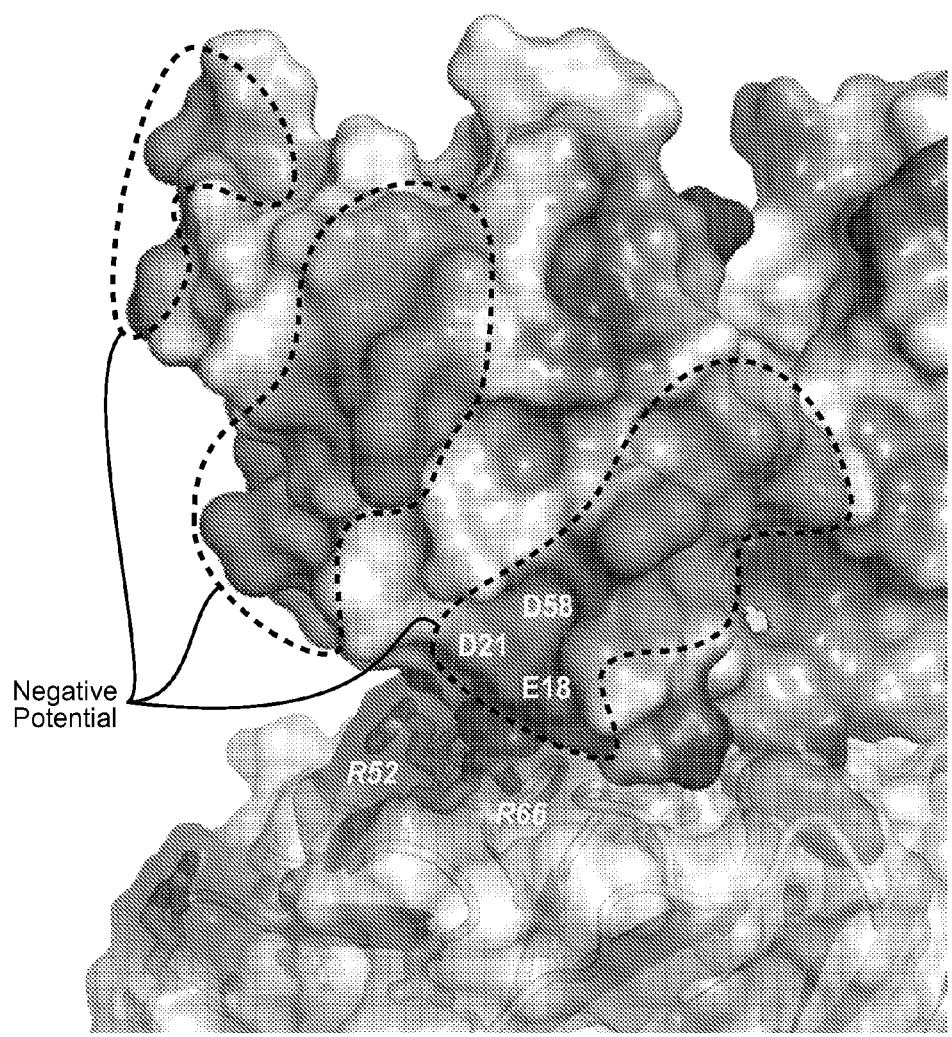
Figure 3A:
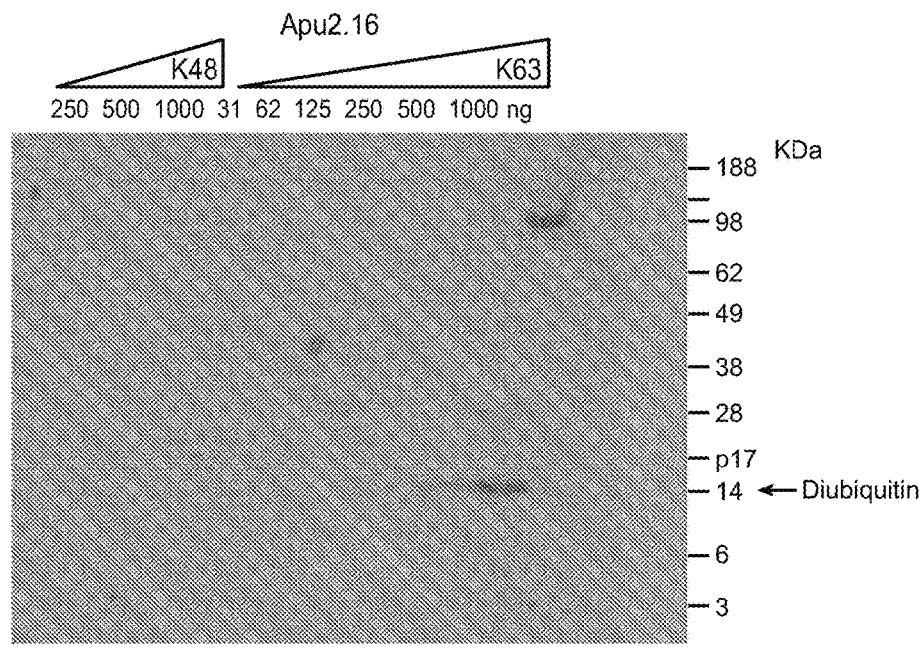
FIGS. 3A-D depict the results of western blotting experiments described in Example 1(E).
Figure 3B:
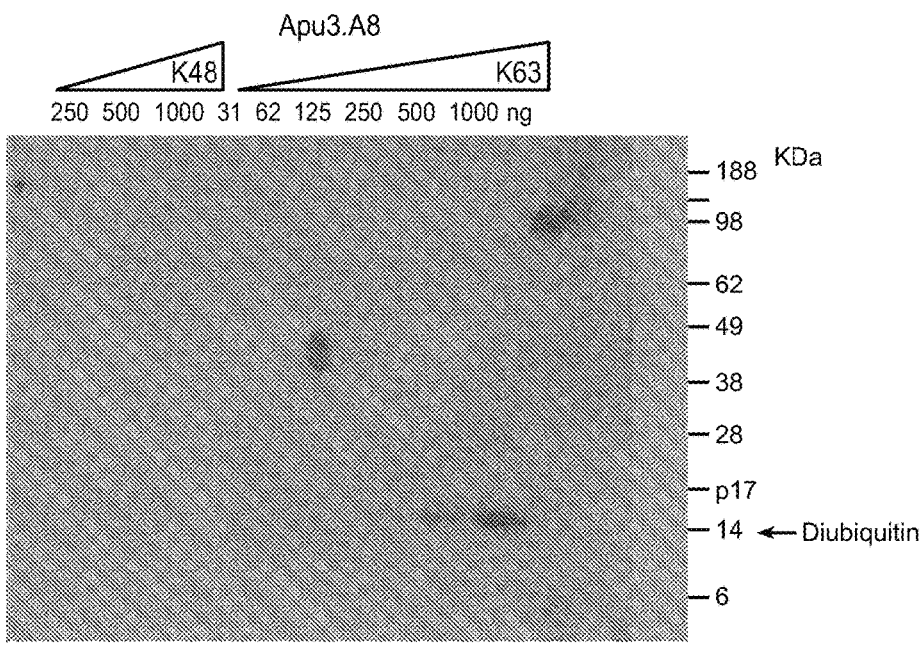
Figure 3C:
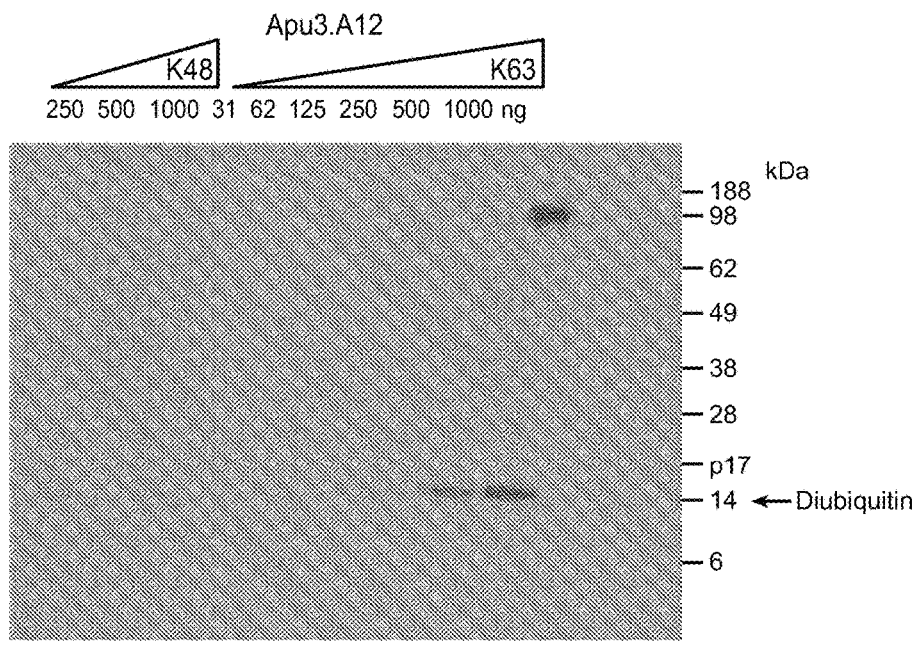
Figure 3D:
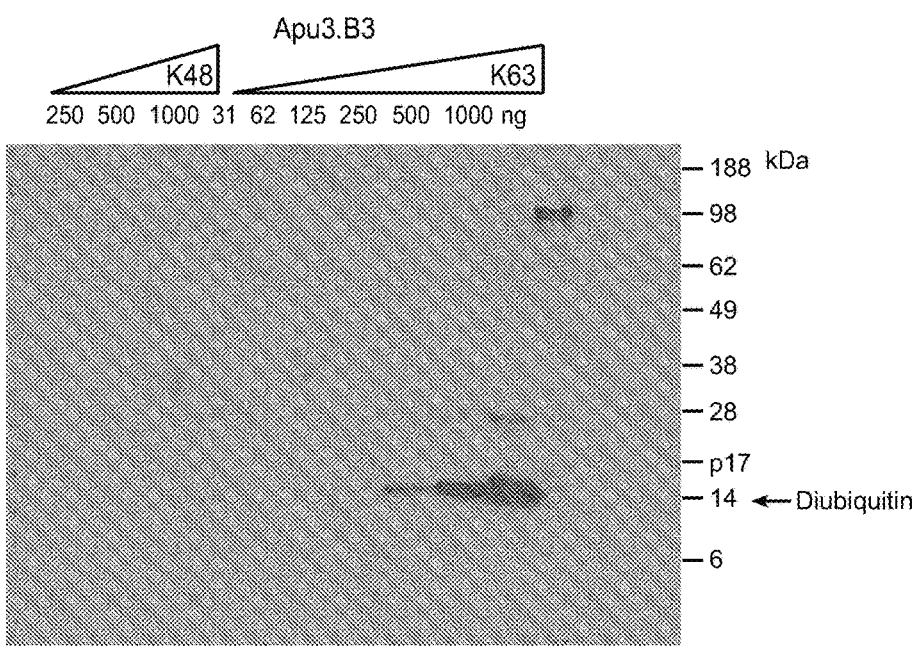

Surprisingly, neither R52 in L2 nor T52 in H2 is in intimate contact with the diubiquitin, and neither residue contributes much to the ubiquitin-binding surface on Apu3.A8. Instead, the effect of these two mutations appears to be driven largely by improved electrostatic compatibility between the surface of the K63-acceptor ubiquitin and the light chain (FIG. 2E). In the Apu3.A8 light chain, R52 (which was introduced in Apu3.A8) and R66 contribute to a positive region that is in close proximity to a negatively charged region on the ubiquitin surface, created in part by residues D21, D58, and E18 from the K63-acceptor ubiquitin.

Example 5

Localization of Polyubiquitin Chains within Cells

The preceding experiments demonstrate that the affinity-matured antibodies of the invention are capable of sensitive and specific detection of K63-linked polyubiquitinated proteins in the context of a western blot, are able to specifically immunoprecipitate K63-linked polyubiquitinated proteins from cellular lysates, and can be used to assist in the elucidation of cellular pathways involving K63-linked polyubiquitination of one or more proteins. Further experiments were performed to ascertain the ability of the antibodies be used in indirect immunofluorescence microscopy for visualization of polyubiquitinated species within cells, and where any such detected proteins localize. HeLa cells grown in 2-well chamber slides were fixed with 4% paraformaldehyde in PBS at room temperature for 20 minutes, rinsed twice with PBS, and permeabilized with PBS containing 0.1% Triton X-100 for 5 minutes. After blocking in Earle's balanced salt solution supplemented with 10% goat serum, 0.1% Triton X-100 and 0.1% saponin for one hour, cells were labeled overnight at 4° C. with 1 µg/mL Apu2.07 anti-K48, 1 µg/mL Apu3.A8 anti-K63, or 5 µg/mL PW8155 anti-proteasome antibodies (Biomol International) in blocking solution. Cells were washed three times with PBS containing 0.1% Triton X-100 and then incubated with 4 drops of Image-IT Fx signal enhancer (Invitrogen) for 15 minutes. Cells were washed three times with PBS containing 0.1% Triton X-100, then stained for 1 hour with Cy2-conjugated anti-human and Texas Red-conjugated anti-rabbit antibodies (Jackson ImmunoResearch) diluted in blocking solution. Cells were washed three times with PBS containing 0.1% Triton X-100, rinsed twice with water, and then mounted with ProLong Gold™ containing DAPI (Invitrogen) and a 1.5 mm coverslip. Cells were examined under an Axioplan 2 light microscope (Zeiss) and images were recorded with a CoolSNAPH$_Q$ CCD camera (Photometrics) controlled by SlideBook™ software (Intelligent Imaging Innovations). In addition, Z-series images were acquired and analyzed by deconvolution microscopy, using SlideBook™ or AutoQuant™ (Media Cybernetics) software (data not shown). To confirm the localization of the signal, samples were also examined with an LSM510 META laser-scanning confocal microscope (Zeiss). All of the images presented are single-capture wide-field fluorescent micrographs.

The results are shown in FIG. 11. The anti-K48-linked polyubiquitin antibody Apu2.07 stained both the nucleus and cytoplasm of HeLa cells, but did not label nucleoli (FIG. 11A). This pattern of staining coincided almost completely with proteasomes labeled with a polyclonal antibody recognizing the core 20S subunits (FIGS. 11B and C), consistent with the idea that K48-linked polyubiquitin chains generally target proteins for proteasomal degradation. K48-linked polyubiquitin chains, but not proteasomes, were detected at the midbody during mitosis. In contrast, HeLa cells stained with the anti-K63-linked polyubiquitin antibody Apu3.A8 labeled cytoplasmic speckles that varied both in number and size between individual cells (FIG. 11D). No co-localization of K63-linked polyubiquitin chains with proteasomes was detected in those speckles (FIGS. 11E and F). In control experiments, staining by the linkage-specific antibodies could be competed by synthesized polyubiquitin chains only if the target linkage was present (data not shown). These results indicate that K48- and K63-linked polyubiquitin chains can occur in distinct subcellular regions, and that antibodies Apu2.07 and Apu3.A8 are able to detect K48-linked or K63-linked polyubiquitin in indirect immunofluorescence assays.

We claim:

1. An isolated antibody or antigen-binding fragment thereof that specifically binds to K63-linked polyubiquitin, comprising:
the HVR-H1 sequence of SEQ ID NO: 5;
the HVR-H2 sequence of SEQ ID NO: 61, optionally having one substitution selected from the following:
(i) a D at position 1,
(ii) an A at position 3,
(iii) a T at position 3, or
(iv) an L at position 6;
the HVR-H3 sequence of SEQ ID NO: 6;
the HVR-L1 sequence of SEQ ID NO: 3;
the HVR-L2 sequence of SEQ ID NO: 9, wherein:
(a) if HVR-H2 is SEQ ID NO: 61, then HVR-L2 optionally has a substitution of an R at position 4,
(b) if HVR-H2 is SEQ ID NO: 61 substituted with a D at position 1, then HVR-L2 optionally has a substitution of a A, S, or T at position 4 of SEQ ID NO: 9;
(c) if HVR-H2 is SEQ ID NO: 61 substituted with an A at position 3, then HVR-L2 optionally has a substitution of an A, L, or N at position 4 of SEQ ID NO: 9; and
(d) if HVR-H2 is SEQ ID NO: 61 substituted with a T at position 3, then HVR-L2 optionally has a substitution of a T at position 4 of SEQ ID NO: 9; and
the HVR-L3 sequence of SEQ ID NO: 4.

2. An isolated antibody or antigen-binding fragment that binds to the same antigenic determinant on polyubiquitin as the antibody or antigen-binding fragment of claim 1, wherein the antibody or antigen-binding fragment does not specifically bind to K48-linked polyubiquitin or monoubiquitin.

3. An isolated antibody or antigen-binding fragment that competes with the antibody of claim 1 for binding to polyubiquitin, wherein the antibody or antigen-binding fragment does not specifically bind to monoubiquitin.

4. The antibody or antigen-binding fragment of claim 1, wherein the antibody or antigen-binding fragment specifically binds to a K63-linked polyubiquitinated protein.

5. The antibody or antigen-binding fragment of claim 4, wherein the antibody or antigen-binding fragment has at least one property selected from inhibiting degradation of the K63-linked polyubiquitinated protein, modulating at least one polyubiquitin-mediated signaling pathway, inhibiting at least one polyubiquitin-mediated signaling pathway, and stimulating at least one polyubiquitin-mediated signaling pathway.

6. A method of producing the antibody or antigen-binding fragment of claim 1, comprising culturing a host cell comprising a nucleic acid molecule encoding the antibody or antigen-binding fragment under conditions wherein the antibody or antigen-binding fragment is produced.

7. A composition comprising an effective amount of the antibody or antigen-binding fragment of claim 1 and a pharmaceutically acceptable carrier.

8. A method of identifying the presence of K63-linked polyubiquitin or a K63-linked polyubiquitinated protein in a sample, comprising contacting the sample with at least one antibody or antigen-binding fragment of claim 1.

9. A method of determining the presence of a K63-linked polyubiquitin or a K63-linked polyubiquitinated protein in a sample suspected of containing a K63-linked polyubiquitin or K63-linked polyubiquitinated protein, comprising exposing the sample to at least one antibody or antigen-binding fragment of claim 1 and determining the binding of the at least one antibody or antigen-binding fragment to a K63-linked polyubiquitin or K63-linked polyubiquitinated protein in the sample.

10. A method of separating K63-linked polyubiquitinated protein from non-K63-linked polyubiquitinated protein in a sample, comprising contacting the sample with at least one antibody or antigen-binding fragment of claim 1.

11. A method of determining the function and/or activity of K63-linked polyubiquitin in a cell or sample comprising contacting the cell or sample with at least one antibody or antigen-binding fragment of claim 1 and assessing the effect of said contacting step on the cell or sample.

12. The antibody of claim 1, wherein the HVR-H2 sequence is SEQ ID NO: 61 and the HVR-L2 sequence is unsubstituted SEQ ID NO: 9.

13. The antibody of claim 1, wherein the HVR-H2 sequence is SEQ ID NO: 61 and the HVR-L2 sequence is SEQ ID NO: 9 substituted with an R at position 4.

14. The antibody of claim 1, wherein the HVR-H2 sequence is SEQ ID NO: 61 substituted with a D at position 1 and the HVR-L2 sequence is SEQ ID NO: 9.

15. The antibody of claim 1, wherein the HVR-H2 sequence is SEQ ID NO: 61 substituted with a D at position 1 and the HVR-L2 sequence is SEQ ID NO: 9 substituted with an A at position 4.

16. The antibody of claim 1, wherein the HVR-H2 sequence is SEQ ID NO: 61 substituted with a D at position 1 and the HVR-L2 sequence is SEQ ID NO: 9 substituted with an S at position 4.

17. The antibody of claim 1, wherein the HVR-H2 sequence is SEQ ID NO: 61 substituted with a D at position 1 and the HVR-L2 sequence is SEQ ID NO: 9 substituted with an T at position 4.

18. The antibody of claim 1, wherein the HVR-H2 sequence is SEQ ID NO: 61 substituted with an A at position 3 and the HVR-L2 sequence is SEQ ID NO: 9 substituted with an A at position 4.

19. The antibody of claim 1, wherein the HVR-H2 sequence is SEQ ID NO: 61 substituted with an A at position 3 and the HVR-L2 sequence is SEQ ID NO: 9 substituted with an L at position 4.

20. The antibody of claim 1, wherein the HVR-H2 sequence is SEQ ID NO: 61 substituted with an A at position 3 and the HVR-L2 sequence is SEQ ID NO: 9 substituted with an N at position 4.

21. The antibody of claim 1, wherein the HVR-H2 sequence is SEQ ID NO: 61 substituted with a T at position 3 and the HVR-L2 sequence is SEQ ID NO: 9 substituted with an T at position 4.

22. The antibody of claim 1, wherein the HVR-H2 sequence is SEQ ID NO: 61 substituted with an L at position 6 and the HVR-L2 sequence is SEQ ID NO: 9.

23. The antibody of claim 1, which has a Kd for K63-linked polyubiquitin of about 10 nM to about 90 nM.

* * * * *

SEQUENCE LISTING

```
<160> NUMBER OF SEQ ID NOS: 228

<210> SEQ ID NO 1
<211> LENGTH: 45
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: (16)..(21)
<223> OTHER INFORMATION: N is soft-randomized
<220> FEATURE:
```

```
<221> NAME/KEY: Unsure
<222> LOCATION: (16)..(30)
<223> OTHER INFORMATION: N is Unknown base
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(30)
<223> OTHER INFORMATION: n is a, c, g, or t

<400> SEQUENCE: 1
ccgaagcttc tgattnnnnn ngcannnnnn ctctactctg gagtc            45

<210> SEQ ID NO 2
<211> LENGTH: 60
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: (19)..(21)
<223> OTHER INFORMATION: N is soft-randomized
<220> FEATURE:
<221> NAME/KEY: Unsure
<222> LOCATION: (19)..(42)
<223> OTHER INFORMATION: N is Unknown base
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: Unsure
<222> LOCATION: (25)..(27)
<223> OTHER INFORMATION: N is soft-randomized
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: Unsure
<222> LOCATION: (31)..(36)
<223> OTHER INFORMATION: N is soft-randomized
<220> FEATURE:
<221> NAME/KEY: misc_feature
<222> LOCATION: (31)..(36)
<223> OTHER INFORMATION: n is a, c, g, or t
<220> FEATURE:
<221> NAME/KEY: Unsure
<222> LOCATION: (40)..(42)
<223> OTHER INFORMATION: N is soft-randomized
<220> FEATURE:
<221> NAME/KEY: misc_feature
<222> LOCATION: (40)..(42)
<223> OTHER INFORMATION: n is a, c, g, or t

<400> SEQUENCE: 2
ggcctggaat gggttgcann nattnnncct nnnnnnggcn nnacttctta tgccgatagc    60

<210> SEQ ID NO 3
<211> LENGTH: 11
<212> TYPE: PRT
<213> ORGANISM: Artificial sequence
<220> FEATURE:
<223> OTHER INFORMATION: sequence is synthesized

<400> SEQUENCE: 3

Arg Ala Ser Gln Ser Val Ser Ser Ala Val Ala
1               5                   10

<210> SEQ ID NO 4
```

<211> LENGTH: 11
<212> TYPE: PRT
<213> ORGANISM: Artificial sequence
<220> FEATURE:
<223> OTHER INFORMATION: sequence is synthesized

<400> SEQUENCE: 4

Gln Gln Tyr Ser Ser Tyr Ser Ser Leu Phe Thr
1               5                   10

<210> SEQ ID NO 5
<211> LENGTH: 6
<212> TYPE: PRT
<213> ORGANISM: Artificial sequence
<220> FEATURE:
<223> OTHER INFORMATION: sequence is synthesized

<400> SEQUENCE: 5

Val Lys Thr Gly Leu Ile
1               5

<210> SEQ ID NO 6
<211> LENGTH: 9
<212> TYPE: PRT
<213> ORGANISM: Artificial sequence
<220> FEATURE:
<223> OTHER INFORMATION: sequence is synthesized

<400> SEQUENCE: 6

Glu Tyr Tyr Arg Trp Tyr Thr Ala Ile
1               5

<210> SEQ ID NO 7
<211> LENGTH: 8
<212> TYPE: PRT
<213> ORGANISM: Artificial sequence
<220> FEATURE:
<223> OTHER INFORMATION: sequence is synthesized

<400> SEQUENCE: 7

Tyr Ser Ala Ser Ser Leu Tyr Ser
1               5

<210> SEQ ID NO 8
<211> LENGTH: 8
<212> TYPE: PRT
<213> ORGANISM: Artificial sequence
<220> FEATURE:
<223> OTHER INFORMATION: sequence is synthesized

<400> SEQUENCE: 8

Tyr Ser Ala Arg Ser Leu Tyr Ser
1               5

<210> SEQ ID NO 9
<211> LENGTH: 8
<212> TYPE: PRT
<213> ORGANISM: Artificial sequence
<220> FEATURE:
<223> OTHER INFORMATION: sequence is synthesized

<400> SEQUENCE: 9

Tyr Ser Ala Val Ser Leu Tyr Ser
1               5

<210> SEQ ID NO 10
<211> LENGTH: 8

-continued

```
<212> TYPE: PRT
<213> ORGANISM: Artificial sequence
<220> FEATURE:
<223> OTHER INFORMATION: sequence is synthesized

<400> SEQUENCE: 10

Tyr Ser Ala Ser Ser Leu Tyr Ser
1               5

<210> SEQ ID NO 11
<211> LENGTH: 8
<212> TYPE: PRT
<213> ORGANISM: Artificial sequence
<220> FEATURE:
<223> OTHER INFORMATION: sequence is synthesized

<400> SEQUENCE: 11

Tyr Ser Ala Arg Ser Leu Tyr Ser
1               5

<210> SEQ ID NO 12
<211> LENGTH: 8
<212> TYPE: PRT
<213> ORGANISM: Artificial sequence
<220> FEATURE:
<223> OTHER INFORMATION: sequence is synthesized

<400> SEQUENCE: 12

Tyr Ser Ala Arg Ser Leu Tyr Ser
1               5

<210> SEQ ID NO 13
<211> LENGTH: 8
<212> TYPE: PRT
<213> ORGANISM: Artificial sequence
<220> FEATURE:
<223> OTHER INFORMATION: sequence is synthesized

<400> SEQUENCE: 13

Tyr Ser Ala Arg Ser Leu Tyr Ser
1               5

<210> SEQ ID NO 14
<211> LENGTH: 8
<212> TYPE: PRT
<213> ORGANISM: Artificial sequence
<220> FEATURE:
<223> OTHER INFORMATION: sequence is synthesized

<400> SEQUENCE: 14

Tyr Ala Ala Ala Ser Leu Tyr Ser
1               5

<210> SEQ ID NO 15
<211> LENGTH: 8
<212> TYPE: PRT
<213> ORGANISM: Artificial sequence
<220> FEATURE:
<223> OTHER INFORMATION: sequence is synthesized

<400> SEQUENCE: 15

Tyr Ser Ala Val Ser Leu Tyr Ser
1               5

<210> SEQ ID NO 16
<211> LENGTH: 8
<212> TYPE: PRT
```

<213> ORGANISM: Artificial sequence
<220> FEATURE:
<223> OTHER INFORMATION: sequence is synthesized

<400> SEQUENCE: 16

Tyr Ser Ala Ala Ser Leu Tyr Ser
1               5

<210> SEQ ID NO 17
<211> LENGTH: 8
<212> TYPE: PRT
<213> ORGANISM: Artificial sequence
<220> FEATURE:
<223> OTHER INFORMATION: sequence is synthesized

<400> SEQUENCE: 17

Tyr Ser Ala Arg Ser Leu Tyr Ser
1               5

<210> SEQ ID NO 18
<211> LENGTH: 8
<212> TYPE: PRT
<213> ORGANISM: Artificial sequence
<220> FEATURE:
<223> OTHER INFORMATION: sequence is synthesized

<400> SEQUENCE: 18

Tyr Ala Ala Ala Ser Leu Tyr Ser
1               5

<210> SEQ ID NO 19
<211> LENGTH: 8
<212> TYPE: PRT
<213> ORGANISM: Artificial sequence
<220> FEATURE:
<223> OTHER INFORMATION: sequence is synthesized

<400> SEQUENCE: 19

Tyr Ser Ala Val Ser Leu Tyr Ser
1               5

<210> SEQ ID NO 20
<211> LENGTH: 8
<212> TYPE: PRT
<213> ORGANISM: Artificial sequence
<220> FEATURE:
<223> OTHER INFORMATION: sequence is synthesized

<400> SEQUENCE: 20

Tyr Ser Ala Val Ser Leu Tyr Ser
1               5

<210> SEQ ID NO 21
<211> LENGTH: 8
<212> TYPE: PRT
<213> ORGANISM: Artificial sequence
<220> FEATURE:
<223> OTHER INFORMATION: sequence is synthesized

<400> SEQUENCE: 21

Tyr Ser Ala Arg Ser Leu Tyr Ser
1               5

<210> SEQ ID NO 22
<211> LENGTH: 8
<212> TYPE: PRT
<213> ORGANISM: Artificial sequence
<220> FEATURE:
<223> OTHER INFORMATION: sequence is synthesized

<400> SEQUENCE: 22

Tyr Ser Ala Arg Ser Leu Tyr Ser
1               5

<210> SEQ ID NO 23
<211> LENGTH: 8
<212> TYPE: PRT
<213> ORGANISM: Artificial sequence
<220> FEATURE:
<223> OTHER INFORMATION: sequence is synthesized

<400> SEQUENCE: 23

Tyr Ala Ala Ala Ser Leu Tyr Ser
1               5

<210> SEQ ID NO 24
<211> LENGTH: 8
<212> TYPE: PRT
<213> ORGANISM: Artificial sequence
<220> FEATURE:
<223> OTHER INFORMATION: sequence is synthesized

<400> SEQUENCE: 24

Tyr Ala Ala Val Ser Leu Tyr Ser
1               5

<210> SEQ ID NO 25
<211> LENGTH: 8
<212> TYPE: PRT
<213> ORGANISM: Artificial sequence
<220> FEATURE:
<223> OTHER INFORMATION: sequence is synthesized

<400> SEQUENCE: 25

Tyr Ser Ala Thr Ser Leu Tyr Ser
1               5

<210> SEQ ID NO 26
<211> LENGTH: 8
<212> TYPE: PRT
<213> ORGANISM: Artificial sequence
<220> FEATURE:
<223> OTHER INFORMATION: sequence is synthesized

<400> SEQUENCE: 26

Tyr Ser Ala Asn Ser Leu Tyr Ser
1               5

<210> SEQ ID NO 27
<211> LENGTH: 8
<212> TYPE: PRT
<213> ORGANISM: Artificial sequence
<220> FEATURE:
<223> OTHER INFORMATION: sequence is synthesized

<400> SEQUENCE: 27

Tyr Ala Ala Ala Ser Leu Tyr Ser
1               5

<210> SEQ ID NO 28
<211> LENGTH: 8
<212> TYPE: PRT
<213> ORGANISM: Artificial sequence
<220> FEATURE:

<223> OTHER INFORMATION: sequence is synthesized

<400> SEQUENCE: 28

Tyr Ser Ala Val Ser Leu Tyr Ser
1               5

<210> SEQ ID NO 29
<211> LENGTH: 8
<212> TYPE: PRT
<213> ORGANISM: Artificial sequence
<220> FEATURE:
<223> OTHER INFORMATION: sequence is synthesized

<400> SEQUENCE: 29

Tyr Ser Ala Ser Ser Leu Tyr Ser
1               5

<210> SEQ ID NO 30
<211> LENGTH: 8
<212> TYPE: PRT
<213> ORGANISM: Artificial sequence
<220> FEATURE:
<223> OTHER INFORMATION: sequence is synthesized

<400> SEQUENCE: 30

Tyr Ser Ala Val Ser Leu Tyr Ser
1               5

<210> SEQ ID NO 31
<211> LENGTH: 8
<212> TYPE: PRT
<213> ORGANISM: Artificial sequence
<220> FEATURE:
<223> OTHER INFORMATION: sequence is synthesized

<400> SEQUENCE: 31

Tyr Ser Ala Val Ser Leu Tyr Ser
1               5

<210> SEQ ID NO 32
<211> LENGTH: 8
<212> TYPE: PRT
<213> ORGANISM: Artificial sequence
<220> FEATURE:
<223> OTHER INFORMATION: sequence is synthesized

<400> SEQUENCE: 32

Phe Ala Ala Ala Ser Leu Tyr Ser
1               5

<210> SEQ ID NO 33
<211> LENGTH: 8
<212> TYPE: PRT
<213> ORGANISM: Artificial sequence
<220> FEATURE:
<223> OTHER INFORMATION: sequence is synthesized

<400> SEQUENCE: 33

Tyr Ser Ala Arg Ser Leu Tyr Ser
1               5

<210> SEQ ID NO 34
<211> LENGTH: 8
<212> TYPE: PRT
<213> ORGANISM: Artificial sequence
<220> FEATURE:
<223> OTHER INFORMATION: sequence is synthesized

<400> SEQUENCE: 34

Tyr Ser Ala Ser Ser Leu Tyr Ser
1               5

<210> SEQ ID NO 35
<211> LENGTH: 8
<212> TYPE: PRT
<213> ORGANISM: Artificial sequence
<220> FEATURE:
<223> OTHER INFORMATION: sequence is synthesized

<400> SEQUENCE: 35

Tyr Ser Ala Ala Ser Leu Tyr Ser
1               5

<210> SEQ ID NO 36
<211> LENGTH: 8
<212> TYPE: PRT
<213> ORGANISM: Artificial sequence
<220> FEATURE:
<223> OTHER INFORMATION: sequence is synthesized

<400> SEQUENCE: 36

Tyr Ser Ala Ala Ser Leu Tyr Ser
1               5

<210> SEQ ID NO 37
<211> LENGTH: 8
<212> TYPE: PRT
<213> ORGANISM: Artificial sequence
<220> FEATURE:
<223> OTHER INFORMATION: sequence is synthesized

<400> SEQUENCE: 37

Tyr Ala Ala Arg Ser Leu Tyr Ser
1               5

<210> SEQ ID NO 38
<211> LENGTH: 8
<212> TYPE: PRT
<213> ORGANISM: Artificial sequence
<220> FEATURE:
<223> OTHER INFORMATION: sequence is synthesized

<400> SEQUENCE: 38

Tyr Ser Ala Val Ser Leu Tyr Ser
1               5

<210> SEQ ID NO 39
<211> LENGTH: 8
<212> TYPE: PRT
<213> ORGANISM: Artificial sequence
<220> FEATURE:
<223> OTHER INFORMATION: sequence is synthesized

<400> SEQUENCE: 39

Tyr Ala Ala Val Ser Leu Tyr Ser
1               5

<210> SEQ ID NO 40
<211> LENGTH: 8
<212> TYPE: PRT
<213> ORGANISM: Artificial sequence
<220> FEATURE:
<223> OTHER INFORMATION: sequence is synthesized

```
<400> SEQUENCE: 40

Tyr Ser Ala Leu Ser Leu Tyr Ser
1               5

<210> SEQ ID NO 41
<211> LENGTH: 8
<212> TYPE: PRT
<213> ORGANISM: Artificial sequence
<220> FEATURE:
<223> OTHER INFORMATION: sequence is synthesized

<400> SEQUENCE: 41

Tyr Ser Ala Ala Ser Leu Tyr Ser
1               5

<210> SEQ ID NO 42
<211> LENGTH: 8
<212> TYPE: PRT
<213> ORGANISM: Artificial sequence
<220> FEATURE:
<223> OTHER INFORMATION: sequence is synthesized

<400> SEQUENCE: 42

Tyr Ser Ala Ser Ser Leu Tyr Ser
1               5

<210> SEQ ID NO 43
<211> LENGTH: 8
<212> TYPE: PRT
<213> ORGANISM: Artificial sequence
<220> FEATURE:
<223> OTHER INFORMATION: sequence is synthesized

<400> SEQUENCE: 43

Tyr Ser Ala Ser Ser Leu Tyr Ser
1               5

<210> SEQ ID NO 44
<211> LENGTH: 8
<212> TYPE: PRT
<213> ORGANISM: Artificial sequence
<220> FEATURE:
<223> OTHER INFORMATION: sequence is synthesized

<400> SEQUENCE: 44

Tyr Ser Ala Ser Ser Leu Tyr Ser
1               5

<210> SEQ ID NO 45
<211> LENGTH: 8
<212> TYPE: PRT
<213> ORGANISM: Artificial sequence
<220> FEATURE:
<223> OTHER INFORMATION: sequence is synthesized

<400> SEQUENCE: 45

Tyr Ser Ala Ala Ser Leu Tyr Ser
1               5

<210> SEQ ID NO 46
<211> LENGTH: 8
<212> TYPE: PRT
<213> ORGANISM: Artificial sequence
<220> FEATURE:
<223> OTHER INFORMATION: sequence is synthesized

<400> SEQUENCE: 46
```

```
Tyr Ser Ala Thr Ser Leu Tyr Ser
1               5

<210> SEQ ID NO 47
<211> LENGTH: 8
<212> TYPE: PRT
<213> ORGANISM: Artificial sequence
<220> FEATURE:
<223> OTHER INFORMATION: sequence is synthesized

<400> SEQUENCE: 47

Tyr Ser Ala Leu Ser Leu Tyr Ser
1               5

<210> SEQ ID NO 48
<211> LENGTH: 8
<212> TYPE: PRT
<213> ORGANISM: Artificial sequence
<220> FEATURE:
<223> OTHER INFORMATION: sequence is synthesized

<400> SEQUENCE: 48

Tyr Ser Ala Val Ser Leu Tyr Ser
1               5

<210> SEQ ID NO 49
<211> LENGTH: 8
<212> TYPE: PRT
<213> ORGANISM: Artificial sequence
<220> FEATURE:
<223> OTHER INFORMATION: sequence is synthesized

<400> SEQUENCE: 49

Tyr Ala Ala Ala Ser Leu Tyr Ser
1               5

<210> SEQ ID NO 50
<211> LENGTH: 8
<212> TYPE: PRT
<213> ORGANISM: Artificial sequence
<220> FEATURE:
<223> OTHER INFORMATION: sequence is synthesized

<400> SEQUENCE: 50

Tyr Ser Ala Ser Ser Leu Tyr Ser
1               5

<210> SEQ ID NO 51
<211> LENGTH: 8
<212> TYPE: PRT
<213> ORGANISM: Artificial sequence
<220> FEATURE:
<223> OTHER INFORMATION: sequence is synthesized

<400> SEQUENCE: 51

Tyr Ala Ala Ala Ser Leu Tyr Ser
1               5

<210> SEQ ID NO 52
<211> LENGTH: 8
<212> TYPE: PRT
<213> ORGANISM: Artificial sequence
<220> FEATURE:
<223> OTHER INFORMATION: sequence is synthesized

<400> SEQUENCE: 52
```

Tyr Ala Ala Ala Ser Leu Tyr Ser
1               5

<210> SEQ ID NO 53
<211> LENGTH: 8
<212> TYPE: PRT
<213> ORGANISM: Artificial sequence
<220> FEATURE:
<223> OTHER INFORMATION: sequence is synthesized

<400> SEQUENCE: 53

Tyr Ser Ala Ala Ser Leu Tyr Ser
1               5

<210> SEQ ID NO 54
<211> LENGTH: 8
<212> TYPE: PRT
<213> ORGANISM: Artificial sequence
<220> FEATURE:
<223> OTHER INFORMATION: sequence is synthesized

<400> SEQUENCE: 54

Tyr Ala Ala Ala Ser Leu Tyr Ser
1               5

<210> SEQ ID NO 55
<211> LENGTH: 8
<212> TYPE: PRT
<213> ORGANISM: Artificial sequence
<220> FEATURE:
<223> OTHER INFORMATION: sequence is synthesized

<400> SEQUENCE: 55

Tyr Ser Ala Ser Ser Leu Tyr Ser
1               5

<210> SEQ ID NO 56
<211> LENGTH: 8
<212> TYPE: PRT
<213> ORGANISM: Artificial sequence
<220> FEATURE:
<223> OTHER INFORMATION: sequence is synthesized

<400> SEQUENCE: 56

Tyr Ser Ala Val Ser Leu Tyr Ser
1               5

<210> SEQ ID NO 57
<211> LENGTH: 8
<212> TYPE: PRT
<213> ORGANISM: Artificial sequence
<220> FEATURE:
<223> OTHER INFORMATION: sequence is synthesized

<400> SEQUENCE: 57

Tyr Ser Ala Val Ser Leu Tyr Ser
1               5

<210> SEQ ID NO 58
<211> LENGTH: 8
<212> TYPE: PRT
<213> ORGANISM: Artificial sequence
<220> FEATURE:
<223> OTHER INFORMATION: sequence is synthesized

<400> SEQUENCE: 58

Tyr Ser Ala Leu Ser Leu Tyr Ser

```
<210> SEQ ID NO 59
<211> LENGTH: 17
<212> TYPE: PRT
<213> ORGANISM: Artificial sequence
<220> FEATURE:
<223> OTHER INFORMATION: sequence is synthesized

<400> SEQUENCE: 59

Tyr Ile Ser Pro Tyr Tyr Gly Ser Thr Ser Tyr Ala Asp Ser Val Lys
1               5                   10                  15
Gly

<210> SEQ ID NO 60
<211> LENGTH: 17
<212> TYPE: PRT
<213> ORGANISM: Artificial sequence
<220> FEATURE:
<223> OTHER INFORMATION: sequence is synthesized

<400> SEQUENCE: 60

Tyr Ile Thr Pro Tyr Tyr Gly Ser Thr Ser Tyr Ala Asp Ser Val Lys
1               5                   10                  15
Gly

<210> SEQ ID NO 61
<211> LENGTH: 17
<212> TYPE: PRT
<213> ORGANISM: Artificial sequence
<220> FEATURE:
<223> OTHER INFORMATION: sequence is synthesized

<400> SEQUENCE: 61

Tyr Ile Ser Pro Tyr Tyr Gly Ser Thr Ser Tyr Ala Asp Ser Val Lys
1               5                   10                  15
Gly

<210> SEQ ID NO 62
<211> LENGTH: 17
<212> TYPE: PRT
<213> ORGANISM: Artificial sequence
<220> FEATURE:
<223> OTHER INFORMATION: sequence is synthesized

<400> SEQUENCE: 62

Asp Ile Thr Pro Tyr Tyr Gly Ser Thr Ser Tyr Ala Asp Ser Val Lys
1               5                   10                  15
Gly

<210> SEQ ID NO 63
<211> LENGTH: 17
<212> TYPE: PRT
<213> ORGANISM: Artificial sequence
<220> FEATURE:
<223> OTHER INFORMATION: sequence is synthesized

<400> SEQUENCE: 63

Tyr Ile Ala Pro Tyr Tyr Gly Ser Thr Ser Tyr Ala Asp Ser Val Lys
1               5                   10                  15
Gly

<210> SEQ ID NO 64
```

```
<211> LENGTH: 17
<212> TYPE: PRT
<213> ORGANISM: Artificial sequence
<220> FEATURE:
<223> OTHER INFORMATION: sequence is synthesized

<400> SEQUENCE: 64

Tyr Ile Thr Pro Tyr Tyr Gly Ser Thr Ser Tyr Ala Asp Ser Val Lys
1               5                   10                  15
Gly

<210> SEQ ID NO 65
<211> LENGTH: 17
<212> TYPE: PRT
<213> ORGANISM: Artificial sequence
<220> FEATURE:
<223> OTHER INFORMATION: sequence is synthesized

<400> SEQUENCE: 65

Tyr Ile Thr Pro Tyr Tyr Gly Ser Thr Ser Tyr Ala Asp Ser Val Lys
1               5                   10                  15
Gly

<210> SEQ ID NO 66
<211> LENGTH: 17
<212> TYPE: PRT
<213> ORGANISM: Artificial sequence
<220> FEATURE:
<223> OTHER INFORMATION: sequence is synthesized

<400> SEQUENCE: 66

Tyr Ile Phe Pro Tyr His Gly Ser Thr Ser Tyr Ala Asp Ser Val Lys
1               5                   10                  15
Gly

<210> SEQ ID NO 67
<211> LENGTH: 17
<212> TYPE: PRT
<213> ORGANISM: Artificial sequence
<220> FEATURE:
<223> OTHER INFORMATION: sequence is synthesized

<400> SEQUENCE: 67

Asp Ile Ala Pro Tyr Tyr Gly Ser Thr Ser Tyr Ala Asp Ser Val Lys
1               5                   10                  15
Gly

<210> SEQ ID NO 68
<211> LENGTH: 17
<212> TYPE: PRT
<213> ORGANISM: Artificial sequence
<220> FEATURE:
<223> OTHER INFORMATION: sequence is synthesized

<400> SEQUENCE: 68

Tyr Ile Ala Pro Tyr Tyr Gly Ala Thr Ser Tyr Ala Asp Ser Val Lys
1               5                   10                  15
Gly

<210> SEQ ID NO 69
<211> LENGTH: 17
<212> TYPE: PRT
<213> ORGANISM: Artificial sequence
<220> FEATURE:
```

<223> OTHER INFORMATION: sequence is synthesized

<400> SEQUENCE: 69

Tyr Ile Phe Pro Tyr Phe Gly Ser Thr Ser Tyr Ala Asp Ser Val Lys
1               5                   10                  15

Gly

<210> SEQ ID NO 70
<211> LENGTH: 17
<212> TYPE: PRT
<213> ORGANISM: Artificial sequence
<220> FEATURE:
<223> OTHER INFORMATION: sequence is synthesized

<400> SEQUENCE: 70

Tyr Ile Ala Pro Tyr Tyr Gly Ser Thr Ser Tyr Ala Asp Ser Val Lys
1               5                   10                  15

Gly

<210> SEQ ID NO 71
<211> LENGTH: 17
<212> TYPE: PRT
<213> ORGANISM: Artificial sequence
<220> FEATURE:
<223> OTHER INFORMATION: sequence is synthesized

<400> SEQUENCE: 71

Asp Ile Ala Pro Tyr Tyr Gly Ser Thr Ser Tyr Ala Asp Ser Val Lys
1               5                   10                  15

Gly

<210> SEQ ID NO 72
<211> LENGTH: 17
<212> TYPE: PRT
<213> ORGANISM: Artificial sequence
<220> FEATURE:
<223> OTHER INFORMATION: sequence is synthesized

<400> SEQUENCE: 72

Tyr Ile Tyr Pro Tyr Tyr Gly Ser Thr Ser Tyr Ala Asp Ser Val Lys
1               5                   10                  15

Gly

<210> SEQ ID NO 73
<211> LENGTH: 17
<212> TYPE: PRT
<213> ORGANISM: Artificial sequence
<220> FEATURE:
<223> OTHER INFORMATION: sequence is synthesized

<400> SEQUENCE: 73

Tyr Ile Ser Pro Tyr Tyr Gly Ser Thr Ser Tyr Ala Asp Ser Val Lys
1               5                   10                  15

Gly

<210> SEQ ID NO 74
<211> LENGTH: 17
<212> TYPE: PRT
<213> ORGANISM: Artificial sequence
<220> FEATURE:
<223> OTHER INFORMATION: sequence is synthesized

<400> SEQUENCE: 74

Tyr Ile Thr Pro Tyr Tyr Gly Ser Thr Ser Tyr Ala Asp Ser Val Lys
1               5                   10                  15

Gly

<210> SEQ ID NO 75
<211> LENGTH: 17
<212> TYPE: PRT
<213> ORGANISM: Artificial sequence
<220> FEATURE:
<223> OTHER INFORMATION: sequence is synthesized

<400> SEQUENCE: 75

Tyr Ile Thr Pro Tyr Tyr Gly Ser Thr Ser Tyr Ala Asp Ser Val Lys
1               5                   10                  15

Gly

<210> SEQ ID NO 76
<211> LENGTH: 17
<212> TYPE: PRT
<213> ORGANISM: Artificial sequence
<220> FEATURE:
<223> OTHER INFORMATION: sequence is synthesized

<400> SEQUENCE: 76

Tyr Ile Ser Pro Tyr Tyr Gly Trp Thr Ser Tyr Ala Asp Ser Val Lys
1               5                   10                  15

Gly

<210> SEQ ID NO 77
<211> LENGTH: 17
<212> TYPE: PRT
<213> ORGANISM: Artificial sequence
<220> FEATURE:
<223> OTHER INFORMATION: sequence is synthesized

<400> SEQUENCE: 77

Asp Ile Ser Pro Tyr Tyr Gly Ser Thr Ser Tyr Ala Asp Ser Val Lys
1               5                   10                  15

Gly

<210> SEQ ID NO 78
<211> LENGTH: 17
<212> TYPE: PRT
<213> ORGANISM: Artificial sequence
<220> FEATURE:
<223> OTHER INFORMATION: sequence is synthesized

<400> SEQUENCE: 78

Tyr Ile Ala Pro Tyr Tyr Gly Ser Thr Ser Tyr Ala Asp Ser Val Lys
1               5                   10                  15

Gly

<210> SEQ ID NO 79
<211> LENGTH: 17
<212> TYPE: PRT
<213> ORGANISM: Artificial sequence
<220> FEATURE:
<223> OTHER INFORMATION: sequence is synthesized

<400> SEQUENCE: 79

Tyr Ile Val Pro Tyr Tyr Gly Ser Thr Ser Tyr Ala Asp Ser Val Lys
1               5                   10                  15

Gly

<210> SEQ ID NO 80
<211> LENGTH: 17
<212> TYPE: PRT
<213> ORGANISM: Artificial sequence
<220> FEATURE:
<223> OTHER INFORMATION: sequence is synthesized

<400> SEQUENCE: 80

Asp Ile Phe Pro Tyr Tyr Gly Ser Ser Ser Tyr Ala Asp Ser Val Lys
1               5                   10                  15

Gly

<210> SEQ ID NO 81
<211> LENGTH: 17
<212> TYPE: PRT
<213> ORGANISM: Artificial sequence
<220> FEATURE:
<223> OTHER INFORMATION: sequence is synthesized

<400> SEQUENCE: 81

Asp Ile Val Pro Tyr Tyr Gly Ser Thr Ser Tyr Ala Asp Ser Val Lys
1               5                   10                  15

Gly

<210> SEQ ID NO 82
<211> LENGTH: 17
<212> TYPE: PRT
<213> ORGANISM: Artificial sequence
<220> FEATURE:
<223> OTHER INFORMATION: sequence is synthesized

<400> SEQUENCE: 82

Tyr Ile Phe Pro Tyr Tyr Gly Ser Thr Ser Tyr Ala Asp Ser Val Lys
1               5                   10                  15

Gly

<210> SEQ ID NO 83
<211> LENGTH: 17
<212> TYPE: PRT
<213> ORGANISM: Artificial sequence
<220> FEATURE:
<223> OTHER INFORMATION: sequence is synthesized

<400> SEQUENCE: 83

Asp Ile Ser Pro Tyr Tyr Gly Ser Thr Ser Tyr Ala Asp Ser Val Lys
1               5                   10                  15

Gly

<210> SEQ ID NO 84
<211> LENGTH: 17
<212> TYPE: PRT
<213> ORGANISM: Artificial sequence
<220> FEATURE:
<223> OTHER INFORMATION: sequence is synthesized

<400> SEQUENCE: 84

Tyr Ile Ala Pro Tyr Tyr Gly Ser Thr Ser Tyr Ala Asp Ser Val Lys
1               5                   10                  15

Gly

<210> SEQ ID NO 85
<211> LENGTH: 17

```
<212> TYPE: PRT
<213> ORGANISM: Artificial sequence
<220> FEATURE:
<223> OTHER INFORMATION: sequence is synthesized

<400> SEQUENCE: 85

Tyr Ile Ala Pro Tyr Tyr Gly Ser Thr Ser Tyr Ala Asp Ser Val Lys
1               5                   10                  15

Gly

<210> SEQ ID NO 86
<211> LENGTH: 17
<212> TYPE: PRT
<213> ORGANISM: Artificial sequence
<220> FEATURE:
<223> OTHER INFORMATION: sequence is synthesized

<400> SEQUENCE: 86

Trp Ile Ser Pro Tyr Tyr Gly Ser Thr Ser Tyr Ala Asp Ser Val Lys
1               5                   10                  15

Gly

<210> SEQ ID NO 87
<211> LENGTH: 17
<212> TYPE: PRT
<213> ORGANISM: Artificial sequence
<220> FEATURE:
<223> OTHER INFORMATION: sequence is synthesized

<400> SEQUENCE: 87

Tyr Ile Ala Pro Tyr Tyr Gly Ser Thr Ser Tyr Ala Asp Ser Val Lys
1               5                   10                  15

Gly

<210> SEQ ID NO 88
<211> LENGTH: 17
<212> TYPE: PRT
<213> ORGANISM: Artificial sequence
<220> FEATURE:
<223> OTHER INFORMATION: sequence is synthesized

<400> SEQUENCE: 88

Tyr Ile Thr Pro Tyr Tyr Gly Ser Thr Ser Tyr Ala Asp Ser Val Lys
1               5                   10                  15

Gly

<210> SEQ ID NO 89
<211> LENGTH: 17
<212> TYPE: PRT
<213> ORGANISM: Artificial sequence
<220> FEATURE:
<223> OTHER INFORMATION: sequence is synthesized

<400> SEQUENCE: 89

Asp Ile Thr Pro Tyr Phe Gly Phe Thr Ser Tyr Ala Asp Ser Val Lys
1               5                   10                  15

Gly

<210> SEQ ID NO 90
<211> LENGTH: 17
<212> TYPE: PRT
<213> ORGANISM: Artificial sequence
<220> FEATURE:
<223> OTHER INFORMATION: sequence is synthesized
```

<400> SEQUENCE: 90

Tyr Ile Ser Pro Tyr Leu Gly Ser Thr Ser Tyr Ala Asp Ser Val Lys
1               5                   10                  15

Gly

<210> SEQ ID NO 91
<211> LENGTH: 17
<212> TYPE: PRT
<213> ORGANISM: Artificial sequence
<220> FEATURE:
<223> OTHER INFORMATION: sequence is synthesized

<400> SEQUENCE: 91

Tyr Ile Phe Pro Tyr Tyr Gly Gly Thr Ser Tyr Ala Asp Ser Val Lys
1               5                   10                  15

Gly

<210> SEQ ID NO 92
<211> LENGTH: 17
<212> TYPE: PRT
<213> ORGANISM: Artificial sequence
<220> FEATURE:
<223> OTHER INFORMATION: sequence is synthesized

<400> SEQUENCE: 92

Tyr Ile Tyr Pro Tyr Tyr Gly Trp Thr Ser Tyr Ala Asp Ser Val Lys
1               5                   10                  15

Gly

<210> SEQ ID NO 93
<211> LENGTH: 17
<212> TYPE: PRT
<213> ORGANISM: Artificial sequence
<220> FEATURE:
<223> OTHER INFORMATION: sequence is synthesized

<400> SEQUENCE: 93

Asp Ile Ser Pro Tyr Tyr Gly Ser Thr Ser Tyr Ala Asp Ser Val Lys
1               5                   10                  15

Gly

<210> SEQ ID NO 94
<211> LENGTH: 17
<212> TYPE: PRT
<213> ORGANISM: Artificial sequence
<220> FEATURE:
<223> OTHER INFORMATION: sequence is synthesized

<400> SEQUENCE: 94

Asp Ile Thr Pro Tyr Tyr Gly Phe Thr Ser Tyr Ala Asp Ser Val Lys
1               5                   10                  15

Gly

<210> SEQ ID NO 95
<211> LENGTH: 17
<212> TYPE: PRT
<213> ORGANISM: Artificial sequence
<220> FEATURE:
<223> OTHER INFORMATION: sequence is synthesized

<400> SEQUENCE: 95

Tyr Ile Ala Pro Tyr Tyr Gly Ser Thr Ser Tyr Ala Asp Ser Val Lys

```
1               5                  10                 15
Gly

<210> SEQ ID NO 96
<211> LENGTH: 17
<212> TYPE: PRT
<213> ORGANISM: Artificial sequence
<220> FEATURE:
<223> OTHER INFORMATION: sequence is synthesized

<400> SEQUENCE: 96

Asp Ile Ser Pro Tyr Tyr Gly Ser Thr Ser Tyr Ala Asp Ser Val Lys
1               5                  10                 15

Gly

<210> SEQ ID NO 97
<211> LENGTH: 17
<212> TYPE: PRT
<213> ORGANISM: Artificial sequence
<220> FEATURE:
<223> OTHER INFORMATION: sequence is synthesized

<400> SEQUENCE: 97

Asp Ile Ser Pro Tyr Tyr Gly Ser Thr Ser Tyr Ala Asp Ser Val Lys
1               5                  10                 15

Gly

<210> SEQ ID NO 98
<211> LENGTH: 17
<212> TYPE: PRT
<213> ORGANISM: Artificial sequence
<220> FEATURE:
<223> OTHER INFORMATION: sequence is synthesized

<400> SEQUENCE: 98

Tyr Ile Thr Pro Tyr Tyr Gly Ser Thr Ser Tyr Ala Asp Ser Val Lys
1               5                  10                 15

Gly

<210> SEQ ID NO 99
<211> LENGTH: 17
<212> TYPE: PRT
<213> ORGANISM: Artificial sequence
<220> FEATURE:
<223> OTHER INFORMATION: sequence is synthesized

<400> SEQUENCE: 99

Tyr Ile Ala Pro Tyr Tyr Gly Ser Thr Ser Tyr Ala Asp Ser Val Lys
1               5                  10                 15

Gly

<210> SEQ ID NO 100
<211> LENGTH: 17
<212> TYPE: PRT
<213> ORGANISM: Artificial sequence
<220> FEATURE:
<223> OTHER INFORMATION: sequence is synthesized

<400> SEQUENCE: 100

Asp Ile Thr Pro Tyr Tyr Gly Phe Thr Ser Tyr Ala Asp Ser Val Lys
1               5                  10                 15

Gly
```

<210> SEQ ID NO 101
<211> LENGTH: 17
<212> TYPE: PRT
<213> ORGANISM: Artificial sequence
<220> FEATURE:
<223> OTHER INFORMATION: sequence is synthesized

<400> SEQUENCE: 101

Asp Ile Thr Pro Tyr Tyr Gly Ser Thr Ser Tyr Ala Asp Ser Val Lys
1               5                   10                  15
Gly

<210> SEQ ID NO 102
<211> LENGTH: 17
<212> TYPE: PRT
<213> ORGANISM: Artificial sequence
<220> FEATURE:
<223> OTHER INFORMATION: sequence is synthesized

<400> SEQUENCE: 102

Asp Ile Thr Pro Tyr Tyr Gly Ser Thr Ser Tyr Ala Asp Ser Val Lys
1               5                   10                  15
Gly

<210> SEQ ID NO 103
<211> LENGTH: 17
<212> TYPE: PRT
<213> ORGANISM: Artificial sequence
<220> FEATURE:
<223> OTHER INFORMATION: sequence is synthesized

<400> SEQUENCE: 103

Asp Ile Thr Pro Tyr Tyr Gly Ser Thr Ser Tyr Ala Asp Ser Val Lys
1               5                   10                  15
Gly

<210> SEQ ID NO 104
<211> LENGTH: 17
<212> TYPE: PRT
<213> ORGANISM: Artificial sequence
<220> FEATURE:
<223> OTHER INFORMATION: sequence is synthesized

<400> SEQUENCE: 104

Tyr Ile Thr Pro Tyr Tyr Gly Ser Thr Ser Tyr Ala Asp Ser Val Lys
1               5                   10                  15
Gly

<210> SEQ ID NO 105
<211> LENGTH: 17
<212> TYPE: PRT
<213> ORGANISM: Artificial sequence
<220> FEATURE:
<223> OTHER INFORMATION: sequence is synthesized

<400> SEQUENCE: 105

Tyr Ile Ser Pro Tyr Tyr Gly Ser Thr Ser Tyr Ala Asp Ser Val Lys
1               5                   10                  15
Gly

<210> SEQ ID NO 106
<211> LENGTH: 17
<212> TYPE: PRT

```
<213> ORGANISM: Artificial sequence
<220> FEATURE:
<223> OTHER INFORMATION: sequence is synthesized

<400> SEQUENCE: 106

Asp Ile Ser Pro Tyr Tyr Gly Ser Thr Ser Tyr Ala Asp Ser Val Lys
1               5                   10                  15
Gly

<210> SEQ ID NO 107
<211> LENGTH: 17
<212> TYPE: PRT
<213> ORGANISM: Artificial sequence
<220> FEATURE:
<223> OTHER INFORMATION: sequence is synthesized

<400> SEQUENCE: 107

Tyr Ile Thr Pro Tyr Tyr Gly Phe Thr Ser Tyr Ala Asp Ser Val Lys
1               5                   10                  15
Gly

<210> SEQ ID NO 108
<211> LENGTH: 17
<212> TYPE: PRT
<213> ORGANISM: Artificial sequence
<220> FEATURE:
<223> OTHER INFORMATION: sequence is synthesized

<400> SEQUENCE: 108

Tyr Ile Thr Pro Tyr Tyr Gly Ser Thr Ser Tyr Ala Asp Ser Val Lys
1               5                   10                  15
Gly

<210> SEQ ID NO 109
<211> LENGTH: 17
<212> TYPE: PRT
<213> ORGANISM: Artificial sequence
<220> FEATURE:
<223> OTHER INFORMATION: sequence is synthesized

<400> SEQUENCE: 109

Asp Ile Thr Pro Tyr Tyr Gly Phe Thr Ser Tyr Ala Asp Ser Val Lys
1               5                   10                  15
Gly

<210> SEQ ID NO 110
<211> LENGTH: 17
<212> TYPE: PRT
<213> ORGANISM: Artificial sequence
<220> FEATURE:
<223> OTHER INFORMATION: sequence is synthesized

<400> SEQUENCE: 110

Tyr Ile Ala Pro Tyr Tyr Gly Ser Thr Ser Tyr Ala Asp Ser Val Lys
1               5                   10                  15
Gly

<210> SEQ ID NO 111
<211> LENGTH: 8
<212> TYPE: PRT
<213> ORGANISM: Artificial sequence
<220> FEATURE:
<223> OTHER INFORMATION: sequence is synthesized
<220> FEATURE:
```

```
<221> NAME/KEY: Variant
<222> LOCATION: (1)..(1)
<223> OTHER INFORMATION: Xaa is Tyr or Phe
<220> FEATURE:
<221> NAME/KEY: Variant
<222> LOCATION: (2)..(2)
<223> OTHER INFORMATION: Xaa is Ala or Ser
<220> FEATURE:
<221> NAME/KEY: Variant
<222> LOCATION: (4)..(4)
<223> OTHER INFORMATION: Xaa is Ser, Arg, Val, Thr, Ala, Asn, or Leu

<400> SEQUENCE: 111

Xaa Xaa Ala Xaa Ser Leu Tyr Ser
1               5

<210> SEQ ID NO 112
<211> LENGTH: 17
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: (1)..(1)
<223> OTHER INFORMATION: Xaa is Tyr, Asp, or Trp
<220> FEATURE:
<221> NAME/KEY: Variant
<222> LOCATION: (3)..(3)
<223> OTHER INFORMATION: Xaa is Ser, Thr, Ala, Phe, Tyr or Val
<220> FEATURE:
<221> NAME/KEY: Variant
<222> LOCATION: (6)..(6)
<223> OTHER INFORMATION: Xaa is Tyr, Phe, Leu or His
<220> FEATURE:
<221> NAME/KEY: Variant
<222> LOCATION: (8)..(8)
<223> OTHER INFORMATION: Xaa is Ser, Gly, Ala, Phe, or Trp

<400> SEQUENCE: 112

Xaa Ile Xaa Pro Tyr Xaa Gly Xaa Thr Ser Tyr Ala Asp Ser Val Lys
1               5                   10                  15

Gly

<210> SEQ ID NO 113
<211> LENGTH: 30
<212> TYPE: PRT
<213> ORGANISM: Artificial sequence
<220> FEATURE:
<223> OTHER INFORMATION: sequence is synthesized

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 114
<211> LENGTH: 14
<212> TYPE: PRT
<213> ORGANISM: Artificial sequence
<220> FEATURE:
<223> OTHER INFORMATION: sequence is synthesized

<400> SEQUENCE: 114

Trp Val Arg Gln Ala Pro Gly Gln Gly Leu Glu Trp Met Gly
1               5                   10

<210> SEQ ID NO 115
```

```
<211> LENGTH: 32
<212> TYPE: PRT
<213> ORGANISM: Artificial sequence
<220> FEATURE:
<223> OTHER INFORMATION: sequence is synthesized

<400> SEQUENCE: 115

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 116
<211> LENGTH: 11
<212> TYPE: PRT
<213> ORGANISM: Artificial sequence
<220> FEATURE:
<223> OTHER INFORMATION: sequence is synthesized

<400> SEQUENCE: 116

Trp Gly Gln Gly Thr Leu Val Thr Val Ser Ser
1               5                   10

<210> SEQ ID NO 117
<211> LENGTH: 25
<212> TYPE: PRT
<213> ORGANISM: Artificial sequence
<220> FEATURE:
<223> OTHER INFORMATION: sequence is synthesized

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 118
<211> LENGTH: 13
<212> TYPE: PRT
<213> ORGANISM: Artificial sequence
<220> FEATURE:
<223> OTHER INFORMATION: sequence is synthesized

<400> SEQUENCE: 118

Trp Val Arg Gln Ala Pro Gly Gln Gly Leu Glu Trp Met
1               5                   10

<210> SEQ ID NO 119
<211> LENGTH: 32
<212> TYPE: PRT
<213> ORGANISM: Artificial sequence
<220> FEATURE:
<223> OTHER INFORMATION: sequence is synthesized

<400> SEQUENCE: 119

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 120
<211> LENGTH: 11
<212> TYPE: PRT
<213> ORGANISM: Artificial sequence
<220> FEATURE:
<223> OTHER INFORMATION: sequence is synthesized
```

```
<400> SEQUENCE: 120

Trp Gly Gln Gly Thr Leu Val Thr Val Ser Ser
1               5                   10

<210> SEQ ID NO 121
<211> LENGTH: 25
<212> TYPE: PRT
<213> ORGANISM: Artificial sequence
<220> FEATURE:
<223> OTHER INFORMATION: sequence is synthesized

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 122
<211> LENGTH: 13
<212> TYPE: PRT
<213> ORGANISM: Artificial sequence
<220> FEATURE:
<223> OTHER INFORMATION: sequence is synthesized

<400> SEQUENCE: 122

Trp Val Arg Gln Ala Pro Gly Gln Gly Leu Glu Trp Met
1               5                   10

<210> SEQ ID NO 123
<211> LENGTH: 31
<212> TYPE: PRT
<213> ORGANISM: Artificial sequence
<220> FEATURE:
<223> OTHER INFORMATION: sequence is synthesized

<400> SEQUENCE: 123

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 124
<211> LENGTH: 11
<212> TYPE: PRT
<213> ORGANISM: Artificial sequence
<220> FEATURE:
<223> OTHER INFORMATION: sequence is synthesized

<400> SEQUENCE: 124

Trp Gly Gln Gly Thr Leu Val Thr Val Ser Ser
1               5                   10

<210> SEQ ID NO 125
<211> LENGTH: 25
<212> TYPE: PRT
<213> ORGANISM: Artificial sequence
<220> FEATURE:
<223> OTHER INFORMATION: sequence is synthesized

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser
            20                  25
```

<210> SEQ ID NO 126
<211> LENGTH: 13
<212> TYPE: PRT
<213> ORGANISM: Artificial sequence
<220> FEATURE:
<223> OTHER INFORMATION: sequence is synthesized

<400> SEQUENCE: 126

Trp Val Arg Gln Ala Pro Gly Gln Gly Leu Glu Trp Met
1               5                   10

<210> SEQ ID NO 127
<211> LENGTH: 30
<212> TYPE: PRT
<213> ORGANISM: Artificial sequence
<220> FEATURE:
<223> OTHER INFORMATION: sequence is synthesized

<400> SEQUENCE: 127

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 128
<211> LENGTH: 11
<212> TYPE: PRT
<213> ORGANISM: Artificial sequence
<220> FEATURE:
<223> OTHER INFORMATION: sequence is synthesized

<400> SEQUENCE: 128

Trp Gly Gln Gly Thr Leu Val Thr Val Ser Ser
1               5                   10

<210> SEQ ID NO 129
<211> LENGTH: 30
<212> TYPE: PRT
<213> ORGANISM: Artificial sequence
<220> FEATURE:
<223> OTHER INFORMATION: sequence is synthesized

<400> SEQUENCE: 129

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 130
<211> LENGTH: 14
<212> TYPE: PRT
<213> ORGANISM: Artificial sequence
<220> FEATURE:
<223> OTHER INFORMATION: sequence is synthesized

<400> SEQUENCE: 130

Trp Ile Arg Gln Pro Pro Gly Lys Gly Leu Glu Trp Ile Gly
1               5                   10

<210> SEQ ID NO 131
<211> LENGTH: 32
<212> TYPE: PRT
<213> ORGANISM: Artificial sequence
<220> FEATURE:
<223> OTHER INFORMATION: sequence is synthesized

<400> SEQUENCE: 131

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 132
<211> LENGTH: 11
<212> TYPE: PRT
<213> ORGANISM: Artificial sequence
<220> FEATURE:
<223> OTHER INFORMATION: sequence is synthesized

<400> SEQUENCE: 132

Trp Gly Gln Gly Thr Leu Val Thr Val Ser Ser
1               5                   10

<210> SEQ ID NO 133
<211> LENGTH: 25
<212> TYPE: PRT
<213> ORGANISM: Artificial sequence
<220> FEATURE:
<223> OTHER INFORMATION: sequence is synthesized

<400> SEQUENCE: 133

Gln Val Gln Leu Gln Glu Ser Gly Pro Gly Leu Val Lys Pro Ser Gln
1               5                   10                  15
Thr Leu Ser Leu Thr Cys Thr Val Ser
            20                  25

<210> SEQ ID NO 134
<211> LENGTH: 13
<212> TYPE: PRT
<213> ORGANISM: Artificial sequence
<220> FEATURE:
<223> OTHER INFORMATION: sequence is synthesized

<400> SEQUENCE: 134

Trp Ile Arg Gln Pro Pro Gly Lys Gly Leu Glu Trp Ile
1               5                   10

<210> SEQ ID NO 135
<211> LENGTH: 32
<212> TYPE: PRT
<213> ORGANISM: Artificial sequence
<220> FEATURE:
<223> OTHER INFORMATION: sequence is synthesized

<400> SEQUENCE: 135

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 136
<211> LENGTH: 11
<212> TYPE: PRT
<213> ORGANISM: Artificial sequence
<220> FEATURE:
<223> OTHER INFORMATION: sequence is synthesized

<400> SEQUENCE: 136

Trp Gly Gln Gly Thr Leu Val Thr Val Ser Ser
1               5                   10

<210> SEQ ID NO 137
<211> LENGTH: 25
<212> TYPE: PRT
<213> ORGANISM: Artificial sequence
<220> FEATURE:
<223> OTHER INFORMATION: sequence is synthesized

<400> SEQUENCE: 137

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 138
<211> LENGTH: 13
<212> TYPE: PRT
<213> ORGANISM: Artificial sequence
<220> FEATURE:
<223> OTHER INFORMATION: sequence is synthesized

<400> SEQUENCE: 138

Trp Ile Arg Gln Pro Pro Gly Lys Gly Leu Glu Trp Ile
1               5                   10

<210> SEQ ID NO 139
<211> LENGTH: 31
<212> TYPE: PRT
<213> ORGANISM: Artificial sequence
<220> FEATURE:
<223> OTHER INFORMATION: sequence is synthesized

<400> SEQUENCE: 139

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 140
<211> LENGTH: 11
<212> TYPE: PRT
<213> ORGANISM: Artificial sequence
<220> FEATURE:
<223> OTHER INFORMATION: sequence is synthesized

<400> SEQUENCE: 140

Trp Gly Gln Gly Thr Leu Val Thr Val Ser Ser
1               5                   10

<210> SEQ ID NO 141
<211> LENGTH: 25
<212> TYPE: PRT
<213> ORGANISM: Artificial sequence
<220> FEATURE:
<223> OTHER INFORMATION: sequence is synthesized

<400> SEQUENCE: 141

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 142
<211> LENGTH: 13
<212> TYPE: PRT

```
<213> ORGANISM: Artificial sequence
<220> FEATURE:
<223> OTHER INFORMATION: sequence is synthesized

<400> SEQUENCE: 142

Trp Ile Arg Gln Pro Pro Gly Lys Gly Leu Glu Trp Ile
1               5                   10

<210> SEQ ID NO 143
<211> LENGTH: 30
<212> TYPE: PRT
<213> ORGANISM: Artificial sequence
<220> FEATURE:
<223> OTHER INFORMATION: sequence is synthesized

<400> SEQUENCE: 143

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 144
<211> LENGTH: 11
<212> TYPE: PRT
<213> ORGANISM: Artificial sequence
<220> FEATURE:
<223> OTHER INFORMATION: sequence is synthesized

<400> SEQUENCE: 144

Trp Gly Gln Gly Thr Leu Val Thr Val Ser Ser
1               5                   10

<210> SEQ ID NO 145
<211> LENGTH: 30
<212> TYPE: PRT
<213> ORGANISM: Artificial sequence
<220> FEATURE:
<223> OTHER INFORMATION: sequence is synthesized

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 146
<211> LENGTH: 14
<212> TYPE: PRT
<213> ORGANISM: Artificial sequence
<220> FEATURE:
<223> OTHER INFORMATION: sequence is synthesized

<400> SEQUENCE: 146

Trp Val Arg Gln Ala Pro Gly Lys Gly Leu Glu Trp Val Ser
1               5                   10

<210> SEQ ID NO 147
<211> LENGTH: 32
<212> TYPE: PRT
<213> ORGANISM: Artificial sequence
<220> FEATURE:
<223> OTHER INFORMATION: sequence is synthesized

<400> SEQUENCE: 147

Arg Phe Thr Ile Ser Arg Asp Asn Ser Lys Asn Thr Leu Tyr Leu Gln
1               5                   10                  15
```

Met Asn Ser Leu Arg Ala Glu Asp Thr Ala Val Tyr Tyr Cys Ala Arg
            20                  25                  30

<210> SEQ ID NO 148
<211> LENGTH: 11
<212> TYPE: PRT
<213> ORGANISM: Artificial sequence
<220> FEATURE:
<223> OTHER INFORMATION: sequence is synthesized

<400> SEQUENCE: 148

Trp Gly Gln Gly Thr Leu Val Thr Val Ser Ser
1               5                   10

<210> SEQ ID NO 149
<211> LENGTH: 25
<212> TYPE: PRT
<213> ORGANISM: Artificial sequence
<220> FEATURE:
<223> OTHER INFORMATION: sequence is synthesized

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 150
<211> LENGTH: 13
<212> TYPE: PRT
<213> ORGANISM: Artificial sequence
<220> FEATURE:
<223> OTHER INFORMATION: sequence is synthesized

<400> SEQUENCE: 150

Trp Val Arg Gln Ala Pro Gly Lys Gly Leu Glu Trp Val
1               5                   10

<210> SEQ ID NO 151
<211> LENGTH: 32
<212> TYPE: PRT
<213> ORGANISM: Artificial sequence
<220> FEATURE:
<223> OTHER INFORMATION: sequence is synthesized

<400> SEQUENCE: 151

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 152
<211> LENGTH: 11
<212> TYPE: PRT
<213> ORGANISM: Artificial sequence
<220> FEATURE:
<223> OTHER INFORMATION: sequence is synthesized

<400> SEQUENCE: 152

Trp Gly Gln Gly Thr Leu Val Thr Val Ser Ser
1               5                   10

<210> SEQ ID NO 153
<211> LENGTH: 25
<212> TYPE: PRT

```
<213> ORGANISM: Artificial sequence
<220> FEATURE:
<223> OTHER INFORMATION: sequence is synthesized

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 154
<211> LENGTH: 13
<212> TYPE: PRT
<213> ORGANISM: Artificial sequence
<220> FEATURE:
<223> OTHER INFORMATION: sequence is synthesized

<400> SEQUENCE: 154

Trp Val Arg Gln Ala Pro Gly Lys Gly Leu Glu Trp Val
1               5                   10

<210> SEQ ID NO 155
<211> LENGTH: 31
<212> TYPE: PRT
<213> ORGANISM: Artificial sequence
<220> FEATURE:
<223> OTHER INFORMATION: sequence is synthesized

<400> SEQUENCE: 155

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 156
<211> LENGTH: 11
<212> TYPE: PRT
<213> ORGANISM: Artificial sequence
<220> FEATURE:
<223> OTHER INFORMATION: sequence is synthesized

<400> SEQUENCE: 156

Trp Gly Gln Gly Thr Leu Val Thr Val Ser Ser
1               5                   10

<210> SEQ ID NO 157
<211> LENGTH: 25
<212> TYPE: PRT
<213> ORGANISM: Artificial sequence
<220> FEATURE:
<223> OTHER INFORMATION: sequence is synthesized

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 158
<211> LENGTH: 13
<212> TYPE: PRT
<213> ORGANISM: Artificial sequence
<220> FEATURE:
<223> OTHER INFORMATION: sequence is synthesized

<400> SEQUENCE: 158
```

Trp Val Arg Gln Ala Pro Gly Lys Gly Leu Glu Trp Val
1               5                   10

<210> SEQ ID NO 159
<211> LENGTH: 30
<212> TYPE: PRT
<213> ORGANISM: Artificial sequence
<220> FEATURE:
<223> OTHER INFORMATION: sequence is synthesized

<400> SEQUENCE: 159

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 160
<211> LENGTH: 11
<212> TYPE: PRT
<213> ORGANISM: Artificial sequence
<220> FEATURE:
<223> OTHER INFORMATION: sequence is synthesized

<400> SEQUENCE: 160

Trp Gly Gln Gly Thr Leu Val Thr Val Ser Ser
1               5                   10

<210> SEQ ID NO 161
<211> LENGTH: 30
<212> TYPE: PRT
<213> ORGANISM: Artificial sequence
<220> FEATURE:
<223> OTHER INFORMATION: sequence is synthesized

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 162
<211> LENGTH: 14
<212> TYPE: PRT
<213> ORGANISM: Artificial sequence
<220> FEATURE:
<223> OTHER INFORMATION: sequence is synthesized

<400> SEQUENCE: 162

Trp Val Arg Gln Ala Pro Gly Lys Gly Leu Glu Trp Val Ser
1               5                   10

<210> SEQ ID NO 163
<211> LENGTH: 32
<212> TYPE: PRT
<213> ORGANISM: Artificial sequence
<220> FEATURE:
<223> OTHER INFORMATION: sequence is synthesized

<400> SEQUENCE: 163

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

-continued

```
<210> SEQ ID NO 164
<211> LENGTH: 11
<212> TYPE: PRT
<213> ORGANISM: Artificial sequence
<220> FEATURE:
<223> OTHER INFORMATION: sequence is synthesized

<400> SEQUENCE: 164

Trp Gly Gln Gly Thr Leu Val Thr Val Ser Ser
1               5                   10

<210> SEQ ID NO 165
<211> LENGTH: 25
<212> TYPE: PRT
<213> ORGANISM: Artificial sequence
<220> FEATURE:
<223> OTHER INFORMATION: sequence is synthesized

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 166
<211> LENGTH: 13
<212> TYPE: PRT
<213> ORGANISM: Artificial sequence
<220> FEATURE:
<223> OTHER INFORMATION: sequence is synthesized

<400> SEQUENCE: 166

Trp Val Arg Gln Ala Pro Gly Lys Gly Leu Glu Trp Val
1               5                   10

<210> SEQ ID NO 167
<211> LENGTH: 32
<212> TYPE: PRT
<213> ORGANISM: Artificial sequence
<220> FEATURE:
<223> OTHER INFORMATION: sequence is synthesized

<400> SEQUENCE: 167

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 168
<211> LENGTH: 11
<212> TYPE: PRT
<213> ORGANISM: Artificial sequence
<220> FEATURE:
<223> OTHER INFORMATION: sequence is synthesized

<400> SEQUENCE: 168

Trp Gly Gln Gly Thr Leu Val Thr Val Ser Ser
1               5                   10

<210> SEQ ID NO 169
<211> LENGTH: 25
<212> TYPE: PRT
<213> ORGANISM: Artificial sequence
<220> FEATURE:
<223> OTHER INFORMATION: sequence is synthesized

<400> SEQUENCE: 169
```

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 170
<211> LENGTH: 13
<212> TYPE: PRT
<213> ORGANISM: Artificial sequence
<220> FEATURE:
<223> OTHER INFORMATION: sequence is synthesized

<400> SEQUENCE: 170

```
Trp Val Arg Gln Ala Pro Gly Lys Gly Leu Glu Trp Val
1               5                   10
```

<210> SEQ ID NO 171
<211> LENGTH: 31
<212> TYPE: PRT
<213> ORGANISM: Artificial sequence
<220> FEATURE:
<223> OTHER INFORMATION: sequence is synthesized

<400> SEQUENCE: 171

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30
```

<210> SEQ ID NO 172
<211> LENGTH: 11
<212> TYPE: PRT
<213> ORGANISM: Artificial sequence
<220> FEATURE:
<223> OTHER INFORMATION: sequence is synthesized

<400> SEQUENCE: 172

```
Trp Gly Gln Gly Thr Leu Val Thr Val Ser Ser
1               5                   10
```

<210> SEQ ID NO 173
<211> LENGTH: 30
<212> TYPE: PRT
<213> ORGANISM: Artificial sequence
<220> FEATURE:
<223> OTHER INFORMATION: sequence is synthesized

<400> SEQUENCE: 173

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30
```

<210> SEQ ID NO 174
<211> LENGTH: 14
<212> TYPE: PRT
<213> ORGANISM: Artificial sequence
<220> FEATURE:
<223> OTHER INFORMATION: sequence is synthesized

<400> SEQUENCE: 174

```
Trp Val Arg Gln Ala Pro Gly Lys Gly Leu Glu Trp Val Ser
1               5                   10
```

-continued

<210> SEQ ID NO 175
<211> LENGTH: 32
<212> TYPE: PRT
<213> ORGANISM: Artificial sequence
<220> FEATURE:
<223> OTHER INFORMATION: sequence is synthesized

<400> SEQUENCE: 175

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 176
<211> LENGTH: 11
<212> TYPE: PRT
<213> ORGANISM: Artificial sequence
<220> FEATURE:
<223> OTHER INFORMATION: sequence is synthesized

<400> SEQUENCE: 176

Trp Gly Gln Gly Thr Leu Val Thr Val Ser Ser
1               5                   10

<210> SEQ ID NO 177
<211> LENGTH: 25
<212> TYPE: PRT
<213> ORGANISM: Artificial sequence
<220> FEATURE:
<223> OTHER INFORMATION: sequence is synthesized

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 178
<211> LENGTH: 13
<212> TYPE: PRT
<213> ORGANISM: Artificial sequence
<220> FEATURE:
<223> OTHER INFORMATION: sequence is synthesized

<400> SEQUENCE: 178

Trp Val Arg Gln Ala Pro Gly Lys Gly Leu Glu Trp Val
1               5                   10

<210> SEQ ID NO 179
<211> LENGTH: 32
<212> TYPE: PRT
<213> ORGANISM: Artificial sequence
<220> FEATURE:
<223> OTHER INFORMATION: sequence is synthesized

<400> SEQUENCE: 179

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 180
<211> LENGTH: 11
<212> TYPE: PRT
<213> ORGANISM: Artificial sequence
<220> FEATURE:

<223> OTHER INFORMATION: sequence is synthesized

<400> SEQUENCE: 180

Trp Gly Gln Gly Thr Leu Val Thr Val Ser Ser
1               5                   10

<210> SEQ ID NO 181
<211> LENGTH: 25
<212> TYPE: PRT
<213> ORGANISM: Artificial sequence
<220> FEATURE:
<223> OTHER INFORMATION: sequence is synthesized

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 182
<211> LENGTH: 13
<212> TYPE: PRT
<213> ORGANISM: Artificial sequence
<220> FEATURE:
<223> OTHER INFORMATION: sequence is synthesized

<400> SEQUENCE: 182

Trp Val Arg Gln Ala Pro Gly Lys Gly Leu Glu Trp Val
1               5                   10

<210> SEQ ID NO 183
<211> LENGTH: 31
<212> TYPE: PRT
<213> ORGANISM: Artificial sequence
<220> FEATURE:
<223> OTHER INFORMATION: sequence is synthesized

<400> SEQUENCE: 183

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 184
<211> LENGTH: 11
<212> TYPE: PRT
<213> ORGANISM: Artificial sequence
<220> FEATURE:
<223> OTHER INFORMATION: sequence is synthesized

<400> SEQUENCE: 184

Trp Gly Gln Gly Thr Leu Val Thr Val Ser Ser
1               5                   10

<210> SEQ ID NO 185
<211> LENGTH: 25
<212> TYPE: PRT
<213> ORGANISM: Artificial sequence
<220> FEATURE:
<223> OTHER INFORMATION: sequence is synthesized

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser

```
            20                  25

<210> SEQ ID NO 186
<211> LENGTH: 13
<212> TYPE: PRT
<213> ORGANISM: Artificial sequence
<220> FEATURE:
<223> OTHER INFORMATION: sequence is synthesized

<400> SEQUENCE: 186

Trp Val Arg Gln Ala Pro Gly Lys Gly Leu Glu Trp Val
1               5                   10

<210> SEQ ID NO 187
<211> LENGTH: 30
<212> TYPE: PRT
<213> ORGANISM: Artificial sequence
<220> FEATURE:
<223> OTHER INFORMATION: sequence is synthesized

<400> SEQUENCE: 187

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 188
<211> LENGTH: 11
<212> TYPE: PRT
<213> ORGANISM: Artificial sequence
<220> FEATURE:
<223> OTHER INFORMATION: sequence is synthesized

<400> SEQUENCE: 188

Trp Gly Gln Gly Thr Leu Val Thr Val Ser Ser
1               5                   10

<210> SEQ ID NO 189
<211> LENGTH: 23
<212> TYPE: PRT
<213> ORGANISM: Artificial sequence
<220> FEATURE:
<223> OTHER INFORMATION: sequence is synthesized

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 190
<211> LENGTH: 15
<212> TYPE: PRT
<213> ORGANISM: Artificial sequence
<220> FEATURE:
<223> OTHER INFORMATION: sequence is synthesized

<400> SEQUENCE: 190

Trp Tyr Gln Gln Lys Pro Gly Lys Ala Pro Lys Leu Leu Ile Tyr
1               5                   10                  15

<210> SEQ ID NO 191
<211> LENGTH: 32
<212> TYPE: PRT
<213> ORGANISM: Artificial sequence
<220> FEATURE:
```

<223> OTHER INFORMATION: sequence is synthesized

<400> SEQUENCE: 191

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 192
<211> LENGTH: 10
<212> TYPE: PRT
<213> ORGANISM: Artificial sequence
<220> FEATURE:
<223> OTHER INFORMATION: sequence is synthesized

<400> SEQUENCE: 192

Phe Gly Gln Gly Thr Lys Val Glu Ile Lys
1               5                   10

<210> SEQ ID NO 193
<211> LENGTH: 23
<212> TYPE: PRT
<213> ORGANISM: Artificial sequence
<220> FEATURE:
<223> OTHER INFORMATION: sequence is synthesized

<400> SEQUENCE: 193

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 194
<211> LENGTH: 15
<212> TYPE: PRT
<213> ORGANISM: Artificial sequence
<220> FEATURE:
<223> OTHER INFORMATION: sequence is synthesized

<400> SEQUENCE: 194

Trp Tyr Leu Gln Lys Pro Gly Gln Ser Pro Gln Leu Leu Ile Tyr
1               5                   10                  15

<210> SEQ ID NO 195
<211> LENGTH: 32
<212> TYPE: PRT
<213> ORGANISM: Artificial sequence
<220> FEATURE:
<223> OTHER INFORMATION: sequence is synthesized

<400> SEQUENCE: 195

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 196
<211> LENGTH: 10
<212> TYPE: PRT
<213> ORGANISM: Artificial sequence
<220> FEATURE:
<223> OTHER INFORMATION: sequence is synthesized

<400> SEQUENCE: 196

Phe Gly Gln Gly Thr Lys Val Glu Ile Lys

<210> SEQ ID NO 197
<211> LENGTH: 23
<212> TYPE: PRT
<213> ORGANISM: Artificial sequence
<220> FEATURE:
<223> OTHER INFORMATION: sequence is synthesized

<400> SEQUENCE: 197

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 198
<211> LENGTH: 15
<212> TYPE: PRT
<213> ORGANISM: Artificial sequence
<220> FEATURE:
<223> OTHER INFORMATION: sequence is synthesized

<400> SEQUENCE: 198

Trp Tyr Gln Gln Lys Pro Gly Gln Ala Pro Arg Leu Leu Ile Tyr
1               5                   10                  15

<210> SEQ ID NO 199
<211> LENGTH: 32
<212> TYPE: PRT
<213> ORGANISM: Artificial sequence
<220> FEATURE:
<223> OTHER INFORMATION: sequence is synthesized

<400> SEQUENCE: 199

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 200
<211> LENGTH: 10
<212> TYPE: PRT
<213> ORGANISM: Artificial sequence
<220> FEATURE:
<223> OTHER INFORMATION: sequence is synthesized

<400> SEQUENCE: 200

Phe Gly Gln Gly Thr Lys Val Glu Ile Lys
1               5                   10

<210> SEQ ID NO 201
<211> LENGTH: 23
<212> TYPE: PRT
<213> ORGANISM: Artificial sequence
<220> FEATURE:
<223> OTHER INFORMATION: sequence is synthesized

<400> SEQUENCE: 201

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 202
<211> LENGTH: 15

<210> SEQ ID NO 202
<211> LENGTH: (not shown)
<212> TYPE: PRT
<213> ORGANISM: Artificial sequence
<220> FEATURE:
<223> OTHER INFORMATION: sequence is synthesized

<400> SEQUENCE: 202

Trp Tyr Gln Gln Lys Pro Gly Gln Pro Pro Lys Leu Leu Ile Tyr
1               5                   10                  15

<210> SEQ ID NO 203
<211> LENGTH: 32
<212> TYPE: PRT
<213> ORGANISM: Artificial sequence
<220> FEATURE:
<223> OTHER INFORMATION: sequence is synthesized

<400> SEQUENCE: 203

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 204
<211> LENGTH: 10
<212> TYPE: PRT
<213> ORGANISM: Artificial sequence
<220> FEATURE:
<223> OTHER INFORMATION: sequence is synthesized

<400> SEQUENCE: 204

Phe Gly Gln Gly Thr Lys Val Glu Ile Lys
1               5                   10

<210> SEQ ID NO 205
<211> LENGTH: 23
<212> TYPE: PRT
<213> ORGANISM: Artificial sequence
<220> FEATURE:
<223> OTHER INFORMATION: sequence is synthesized

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 206
<211> LENGTH: 15
<212> TYPE: PRT
<213> ORGANISM: Artificial sequence
<220> FEATURE:
<223> OTHER INFORMATION: sequence is synthesized

<400> SEQUENCE: 206

Trp Tyr Gln Gln Lys Pro Gly Lys Ala Pro Lys Leu Leu Ile Tyr
1               5                   10                  15

<210> SEQ ID NO 207
<211> LENGTH: 32
<212> TYPE: PRT
<213> ORGANISM: Artificial sequence
<220> FEATURE:
<223> OTHER INFORMATION: sequence is synthesized

<400> SEQUENCE: 207

Gly Val Pro Ser Arg Phe Ser Gly Ser Arg Ser Gly Thr Asp Phe Thr

```
                1               5                  10                  15
Leu Thr Ile Ser Ser Leu Gln Pro Glu Asp Phe Ala Thr Tyr Tyr Cys
                20                  25                  30
```

<210> SEQ ID NO 208
<211> LENGTH: 10
<212> TYPE: PRT
<213> ORGANISM: Artificial sequence
<220> FEATURE:
<223> OTHER INFORMATION: sequence is synthesized

<400> SEQUENCE: 208

```
Phe Gly Gln Gly Thr Lys Val Glu Ile Lys
1               5                   10
```

<210> SEQ ID NO 209
<211> LENGTH: 25
<212> TYPE: PRT
<213> ORGANISM: Artificial sequence
<220> FEATURE:
<223> OTHER INFORMATION: sequence is synthesized

<400> SEQUENCE: 209

```
Glu Val Gln Leu Val Glu Ser Gly Gly Gly Leu Val Gln Pro Gly Gly
1               5                   10                  15
Ser Leu Arg Leu Ser Cys Ala Ala Ser
                20                  25
```

<210> SEQ ID NO 210
<211> LENGTH: 13
<212> TYPE: PRT
<213> ORGANISM: Artificial sequence
<220> FEATURE:
<223> OTHER INFORMATION: sequence is synthesized

<400> SEQUENCE: 210

```
Trp Val Arg Gln Ala Pro Gly Lys Gly Leu Glu Trp Val
1               5                   10
```

<210> SEQ ID NO 211
<211> LENGTH: 30
<212> TYPE: PRT
<213> ORGANISM: Artificial sequence
<220> FEATURE:
<223> OTHER INFORMATION: sequence is synthesized

<400> SEQUENCE: 211

```
Arg Phe Thr Ile Ser Ala Asp Thr Ser Lys Asn Thr Ala Tyr Leu Gln
1               5                   10                  15
Met Asn Ser Leu Arg Ala Glu Asp Thr Ala Val Tyr Tyr Cys
                20                  25                  30
```

<210> SEQ ID NO 212
<211> LENGTH: 11
<212> TYPE: PRT
<213> ORGANISM: Artificial sequence
<220> FEATURE:
<223> OTHER INFORMATION: sequence is synthesized

<400> SEQUENCE: 212

```
Trp Gly Gln Gly Thr Leu Val Thr Val Ser Ser
1               5                   10
```

<210> SEQ ID NO 213
<211> LENGTH: 23

<212> TYPE: PRT
<213> ORGANISM: Artificial sequence
<220> FEATURE:
<223> OTHER INFORMATION: sequence is synthesized

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 214
<211> LENGTH: 15
<212> TYPE: PRT
<213> ORGANISM: Artificial sequence
<220> FEATURE:
<223> OTHER INFORMATION: sequence is synthesized

<400> SEQUENCE: 214

Trp Tyr Gln Gln Lys Pro Gly Lys Ala Pro Lys Leu Leu Ile Tyr
1               5                   10                  15

<210> SEQ ID NO 215
<211> LENGTH: 32
<212> TYPE: PRT
<213> ORGANISM: Artificial sequence
<220> FEATURE:
<223> OTHER INFORMATION: sequence is synthesized

<400> SEQUENCE: 215

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 216
<211> LENGTH: 10
<212> TYPE: PRT
<213> ORGANISM: Artificial sequence
<220> FEATURE:
<223> OTHER INFORMATION: sequence is synthesized

<400> SEQUENCE: 216

Phe Arg Gln Gly Thr Lys Val Glu Ile Lys
1               5                   10

<210> SEQ ID NO 217
<211> LENGTH: 25
<212> TYPE: PRT
<213> ORGANISM: Artificial sequence
<220> FEATURE:
<223> OTHER INFORMATION: sequence is synthesized

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 218
<211> LENGTH: 13
<212> TYPE: PRT
<213> ORGANISM: Artificial sequence
<220> FEATURE:
<223> OTHER INFORMATION: sequence is synthesized

```
<400> SEQUENCE: 218

Trp Val Arg Gln Ala Pro Gly Lys Gly Leu Glu Trp Val
1               5                   10

<210> SEQ ID NO 219
<211> LENGTH: 30
<212> TYPE: PRT
<213> ORGANISM: Artificial sequence
<220> FEATURE:
<223> OTHER INFORMATION: sequence is synthesized

<400> SEQUENCE: 219

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 220
<211> LENGTH: 11
<212> TYPE: PRT
<213> ORGANISM: Artificial sequence
<220> FEATURE:
<223> OTHER INFORMATION: sequence is synthesized

<400> SEQUENCE: 220

Trp Gly Gln Gly Thr Leu Val Thr Val Ser Ser
1               5                   10

<210> SEQ ID NO 221
<211> LENGTH: 16
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: (1)..(1)
<223> OTHER INFORMATION: Xaa is Tyr, Asp, or Trp
<220> FEATURE:
<221> NAME/KEY: Variant
<222> LOCATION: (3)..(3)
<223> OTHER INFORMATION: Xaa is Ser, Thr, Ala, Phe, Tyr, or Val
<220> FEATURE:
<221> NAME/KEY: Variant
<222> LOCATION: (6)..(6)
<223> OTHER INFORMATION: Xaa is Tyr, Phe, Leu, or His
<220> FEATURE:
<221> NAME/KEY: Variant
<222> LOCATION: (8)..(8)
<223> OTHER INFORMATION: Xaa is Ser, Gly, Ala, Phe, or Trp

<400> SEQUENCE: 221

Xaa Ile Xaa Pro Tyr Xaa Gly Xaa Thr Ser Tyr Ala Asp Ser Val Lys
1               5                   10                  15

<210> SEQ ID NO 222
<211> LENGTH: 8
<212> TYPE: PRT
<213> ORGANISM: Artificial sequence
<220> FEATURE:
<223> OTHER INFORMATION: sequence is synthesized
<220> FEATURE:
<221> NAME/KEY: Variant
<222> LOCATION: (1)..(1)
<223> OTHER INFORMATION: Xaa is Tyr or Phe
<220> FEATURE:
<221> NAME/KEY: Variant
<222> LOCATION: (2)..(2)
<223> OTHER INFORMATION: Xaa is Ala or Ser
<220> FEATURE:
```

```
<221> NAME/KEY: Variant
<222> LOCATION: (4)..(4)
<223> OTHER INFORMATION: Xaa is Ser, Arg, Val, Thr, Ala, Asn, or Leu

<400> SEQUENCE: 222

Xaa Xaa Ala Xaa Ser Leu Tyr Ser
1               5

<210> SEQ ID NO 223
<211> LENGTH: 76
<212> TYPE: PRT
<213> ORGANISM: Homo sapiens

<400> SEQUENCE: 223

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 224
<211> LENGTH: 107
<212> TYPE: PRT
<213> ORGANISM: Artificial sequence
<220> FEATURE:
<223> OTHER INFORMATION: sequence is synthesized

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 225
<211> LENGTH: 110
<212> TYPE: PRT
<213> ORGANISM: Artificial sequence
<220> FEATURE:
<223> OTHER INFORMATION: sequence is synthesized

<400> SEQUENCE: 225

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Val Ser Ser
            20                  25                  30
```

-continued

Ala Val Ala Trp Tyr Gln Gln Lys Pro Gly Glu Ala Pro Lys Leu Leu
        35                  40                  45

Ile Tyr Ser Ala Ser Ser Leu Tyr Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Tyr Ser Ser Tyr Ser
                 85                  90                  95

Ser Leu Phe Thr Phe Gly Gln Gly Thr Lys Val Glu Ile Lys
                100                 105                 110

<210> SEQ ID NO 226
<211> LENGTH: 123
<212> TYPE: PRT
<213> ORGANISM: Artificial sequence
<220> FEATURE:
<223> OTHER INFORMATION: sequence is synthesized

<400> SEQUENCE: 226

Glu Ile Ser Glu Val Gln Leu Val Glu Ser Gly Gly Leu Val Gln
 1               5                  10                  15

Pro Gly Gly Ser Leu Arg Leu Ser Cys Ala Ala Ser Gly Phe Asn Val
                 20                  25                  30

Lys Thr Gly Leu Ile His Trp Val Arg Gln Ala Pro Gly Lys Gly Leu
             35                  40                  45

Glu Trp Val Ala Tyr Ile Ser Pro Tyr Tyr Gly Ser Thr Ser Tyr Ala
 50                  55                  60

Asp Ser Val Lys Gly Arg Phe Thr Ile Ser Ala Asp Thr Ser Lys Asn
 65                  70                  75                  80

Thr Ala Tyr Leu Gln Met Asn Ser Leu Arg Ala Glu Asp Thr Ala Val
                 85                  90                  95

Tyr Tyr Cys Ala Arg Glu Tyr Tyr Arg Trp Tyr Thr Ala Ile Asp Tyr
                100                 105                 110

Trp Gly Gln Gly Thr Leu Val Thr Val Ser Ser
            115                 120

<210> SEQ ID NO 227
<211> LENGTH: 123
<212> TYPE: PRT
<213> ORGANISM: Artificial sequence
<220> FEATURE:
<223> OTHER INFORMATION: sequence is synthesized

<400> SEQUENCE: 227

Glu Ile Ser Glu Val Gln Leu Val Glu Ser Gly Gly Leu Val Gln
 1               5                  10                  15

Pro Gly Gly Ser Leu Arg Leu Ser Cys Ala Ala Ser Gly Phe Asn Val
                 20                  25                  30

Lys Thr Gly Leu Ile His Trp Val Arg Gln Ala Pro Gly Lys Gly Leu
             35                  40                  45

Glu Trp Val Ala Tyr Ile Thr Pro Tyr Tyr Gly Ser Thr Ser Tyr Ala
 50                  55                  60

Asp Ser Val Lys Gly Arg Phe Thr Ile Ser Ala Asp Thr Ser Lys Asn
 65                  70                  75                  80

Thr Ala Tyr Leu Gln Met Asn Ser Leu Arg Ala Glu Asp Thr Ala Val
                 85                  90                  95

Tyr Tyr Cys Ala Arg Glu Tyr Tyr Arg Trp Tyr Thr Ala Ile Asp Tyr
                100                 105                 110

```
Trp Gly Gln Gly Thr Leu Val Thr Val Ser Ser
        115                 120

<210> SEQ ID NO 228
<211> LENGTH: 120
<212> TYPE: PRT
<213> ORGANISM: Artificial sequence
<220> FEATURE:
<223> OTHER INFORMATION: sequence is synthesized

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Val Lys Thr Gly
            20                  25                  30

Leu Ile His Trp Val Arg Gln Ala Pro Gly Lys Gly Leu Glu Trp Val
        35                  40                  45

Ala Tyr Ile Thr Pro Tyr Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Tyr Tyr Arg Trp Tyr Thr Ala Ile Asp Tyr Trp Gly Gln
            100                 105                 110

Gly Thr Leu Val Thr Val Ser Ser
        115                 120
```